US010246507B2

(12) United States Patent
Lee et al.

(10) Patent No.: US 10,246,507 B2
(45) Date of Patent: Apr. 2, 2019

(54) POLYPEPTIDE, ANTI-VEGF ANTIBODY, AND ANTI-C-MET/ANTI-VEGF BISPECIFIC ANTIBODIES COMPRISING THE SAME

(71) Applicant: Samsung Electronics Co., Ltd., Suwon-si, Gyeonggi-do (KR)

(72) Inventors: Seung Hyun Lee, Suwon-si (KR); Soo Yeon Jung, Seongnam-si (KR); Bo Gyou Kim, Seoul (KR); Seung Ja Oh, Seoul (KR); Ji Min Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 31 days.

(21) Appl. No.: 14/869,636

(22) Filed: Sep. 29, 2015

(65) Prior Publication Data
US 2016/0090427 A1 Mar. 31, 2016

(30) Foreign Application Priority Data

Sep. 29, 2014 (KR) ........................ 10-2014-0130561

(51) Int. Cl.
| *A61K 39/395* | (2006.01) |
| *C07K 16/22* | (2006.01) |
| *C07K 16/28* | (2006.01) |
| *C07K 16/30* | (2006.01) |

(52) U.S. Cl.
CPC .......... *C07K 16/22* (2013.01); *C07K 16/2863* (2013.01); *A61K 39/3955* (2013.01); *A61K 39/39558* (2013.01); *C07K 2317/24* (2013.01); *C07K 2317/31* (2013.01); *C07K 2317/622* (2013.01); *C07K 2317/73* (2013.01); *C07K 2317/76* (2013.01); *C07K 2317/92* (2013.01); *C07K 2319/74* (2013.01)

(58) Field of Classification Search
None
See application file for complete search history.

(56) References Cited

U.S. PATENT DOCUMENTS

| 7,601,351 | B1 | 10/2009 | Rosen et al. | |
| 7,906,117 | B2 * | 3/2011 | Smith | C07K 16/248 |
| | | | | 424/133.1 |
| 8,193,321 | B2 | 6/2012 | Bostrom et al. | |
| 8,216,571 | B2 | 7/2012 | Ramachandra et al. | |
| 8,268,314 | B2 | 9/2012 | Baehner et al. | |
| 8,349,322 | B2 | 1/2013 | Borras et al. | |
| 8,481,687 | B2 * | 7/2013 | Vincent | C07K 16/32 |
| | | | | 530/350 |
| 8,512,699 | B2 | 8/2013 | Fuh et al. | |
| 8,562,985 | B2 | 10/2013 | Michaud et al. | |
| 8,563,696 | B2 | 10/2013 | Cheong et al. | |
| 8,834,882 | B2 * | 9/2014 | Silence | C07K 16/2875 |
| | | | | 424/156.1 |
| 9,017,686 | B2 | 4/2015 | Bostrom et al. | |
| 9,101,610 | B2 * | 8/2015 | Cheong | C07K 16/2863 |
| 2003/0175274 | A1 | 9/2003 | Rosen et al. | |
| 2004/0166544 | A1 | 8/2004 | Morton et al. | |
| 2013/0089556 | A1 * | 4/2013 | Cheong | C07K 16/2863 |
| | | | | 424/138.1 |

FOREIGN PATENT DOCUMENTS

| KR | 2011-0047698 A | 5/2011 |
| KR | 2011-0081812 A | 7/2011 |
| KR | 2012-0130658 A | 12/2012 |

OTHER PUBLICATIONS

Sela-Culang et al. Frontiers in Immunology, vol. 4, Article 302, Oct. 2013, doi: 10.3389/fimmu.2013.00302.*
Holliger et al., Nature Biotechnology, 23(9):1126-1136, 2005.*
Dimerization of ScFv/Fab. 2 pages [online]. Creative Biolabs, undated [retrieved on Feb. 18, 2018]. Retrieved from the Internet: <URL:www.Creative-Biolabs.com/dimerization-of-scfv-and-fab-fragments.html>.*

* cited by examiner

*Primary Examiner* — Marianne P Allen
(74) *Attorney, Agent, or Firm* — Leydig, Voit & Mayer, Ltd.

(57) ABSTRACT

A polypeptide, an anti-VEGF antibody and an anti-c-Met/anti-VEGF bispecific antibody, which includes the polypeptide, a pharmaceutical composition including the antibody, and a method of treating cancer using the antibody.

12 Claims, 7 Drawing Sheets

Specification includes a Sequence Listing.

POLYPEPTIDE, ANTI-VEGF ANTIBODY, AND ANTI-C-MET/ANTI-VEGF BISPECIFIC ANTIBODIES COMPRISING THE SAME

CROSS-REFERENCE TO RELATED APPLICATIONS

This application claims the benefit of Korean Patent Application No. 10-2014-0130561 filed on Sep. 29, 2014 in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 201,669 byte ASCII (Text) file named "721497_ST25-Revised.TXT" created Mar. 9, 2017 Sep. 28, 2015.

BACKGROUND OF THE INVENTION

1. Field

Provided is an anti-VEGF antibody, an anti-c-Met/anti-VEGF bispecific antibody, a pharmaceutical composition including the antibodies, and a method of treating cancer using the antibodies.

2. Description of the Related Art c-Met, which is a receptor tyrosine kinase (RTK) present at the surface of cells, binds to its ligand, hepatocyte growth Factor (HGF), and stimulates intracellular signal transduction, to promote cell growth. C-Met is overexpressed in cancer cells and induces the proliferation of cancer cells, the penetration of the cancer cells, and angiogenesis. In many cases, the overexpression of c-Met protein is closely related to poor prognosis of cancer.

Vascular endothelial cell growth factor (VEGF) is present in both normal and cancer cells, but it is secreted from cancer cells and binds to the VEGF receptor (VEGFR), to induce angiogenesis. Cancer cells can be supplied with necessary nutrients from blood vessels newly formed by the angiogenesis.

Therefore, a simultaneous inhibition of both c-Met and VEGF is expected to lead to more effective inhibition of cancer cell growth. For these reasons, it is necessary to develop a dual inhibitor which can inhibit c-Met and VEGF simultaneously. This invention provides such an inhibitor.

BRIEF SUMMARY OF THE INVENTION

One embodiment provides an anti-VEGF antibody or an antigen-binding fragment thereof comprising or consisting essentially of at least one heavy chain complementarity determining region selected from the group consisting of CDR-H1 including the amino acid sequence of SEQ ID NO: 109, 110, 111, 112, or 113, CDR-H2 including the amino acid sequence of SEQ ID NO: 114, 115, 116, 117, 118, 119, 120, or 121, and CDR-H3 including the amino acid sequence of SEQ ID NO: 122, 123, 124, 125, 126, 127, 128, or 129; at least one light chain complementarity determining region selected from the group consisting of CDR-L1 including the amino acid sequence of SEQ ID NO: 130, 131, 132, 133, 134, 135, 136, or 137, CDR-L2 including the amino acid sequence of SEQ ID NO: 138, 139, 140, 141, 142, 143, 144, or 145, and CDR-L3 including the amino acid sequence of SEQ ID NO: 146, 147, 148, 149, 150 or 151; or a combination of the at least one heavy chain complementarity determining region and the at least one light chain complementarity determining region.

Another embodiment provides an anti-c-Met/anti-VEGF bispecific antibody including an anti-c-Met antibody or an antigen-binding fragment thereof, and an anti-VEGF antibody or an antigen-binding fragment thereof.

Another embodiment provides a pharmaceutical composition including the anti-VEGF antibody and/or the anti-c-Met/anti-VEGF bispecific antibody. The pharmaceutical composition may be used for preventing and/or treating a cancer.

Another embodiment provides a method of preventing and/or treating a cancer in a subject, including administrating the anti-VEGF antibody and/or the anti-c-Met/anti-VEGF bispecific antibody to the subject.

Additional compositions and methods are described in the following sections.

DETAILED DESCRIPTION OF THE INVENTION

Figure 1:
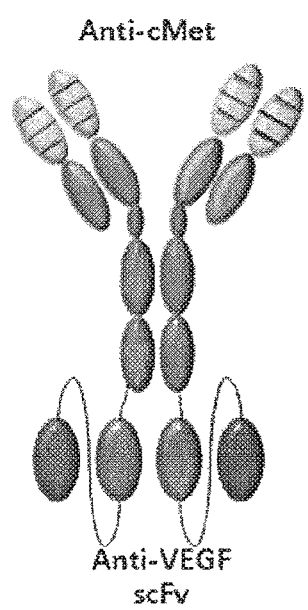
FIG. 1 is a schematic of an anti-c-Met/anti-VEGF bispecific antibody.

One embodiment provides a polypeptide comprising a novel amino acid sequence. The polypeptide may function as a CDR of an anti-VEGF antibody. In particular, the polypeptide may comprise or consisting essentially of one amino acid sequence or a combination of two or more amino acid sequences selected from the group consisting of SEQ ID NO: 109 to SEQ ID NO: 151. The functions of the polypeptide comprising or consisting essentially of the amino acid sequence selected from SEQ ID NO: 109 to SEQ ID NO: 151 as a CDR of an anti-VEGF antibody are summarized in Tables 1 and 2, as follows:

TABLE 1

| CDR-H1 | CDR-H2 | CDR-H3 |
|---|---|---|
| GYAMS (SEQ ID NO: 109) | SIYSSSGSKYYADSVKG (SEQ ID NO: 114) | ASSTCTRTWCSYDDAMDV (SEQ ID NO: 122) |

TABLE 1-continued

| CDR-H1 | CDR-H2 | CDR-H3 |
|---|---|---|
| DYAMS (SEQ ID NO: 110) | SIYPGSGSKYYADSVKG (SEQ ID NO: 115) | DAWFRGHNVFDY (SEQ ID NO: 123) |
| NYDMS (SEQ ID NO: 111) | GIYPNGGSKYYADSVKG (SEQ ID NO: 116) | ALRQCQRYWCSYADGMDV (SEQ ID NO: 124) |
| DYYMS (SEQ ID NO: 112) | AIYSGGGSIYYADSVKG (SEQ ID NO: 117) | DVQWNKAPRFDY (SEQ ID NO: 125) |
| SYSMS (SEQ ID NO: 113) | GISHGGGNKYYADSVKG (SEQ ID NO: 118) | DLRANNDTGFDY (SEQ ID NO: 126) |
| NYDMS (SEQ ID NO: 111) | LISHGGGNIYYADSVKG (SEQ ID NO: 119) | VPVMCTNHWCSYANGMDV (SEQ ID NO: 127) |
| GYAMS (SEQ ID NO: 109) | GISHDGGNTYYADSVKG (SEQ ID NO: 120) | DRRKGPSTEFDY (SEQ ID NO: 128) |
| DYAMS (SEQ ID NO: 110) | WIYPGDSSIYYADSVKG (SEQ ID NO: 121) | LLSIDQAQLHYYYDAMDV (SEQ ID NO: 129) |

TABLE 2

| CDR-L1 | CDR-L2 | CDR-L3 |
|---|---|---|
| TGSSSNIGNNAVT (SEQ ID NO: 130) | DDSHRPS (SEQ ID NO: 138) | GTWDYSLSGYV (SEQ ID NO: 146) |
| TGSSSNIGSNNVT (SEQ ID NO: 131) | SDSHRPS (SEQ ID NO: 139) | GSWDYSLSAYV (SEQ ID NO: 147) |
| TGSSSNIGSNYVS (SEQ ID NO: 132) | ADSQRPS (SEQ ID NO: 140) | GTWDYSLSGYV (SEQ ID NO: 146) |
| SGSSSNIGSNDVS (SEQ ID NO: 133) | ADSNRPS (SEQ ID NO: 141) | GSWDYSLSGYV (SEQ ID NO: 148) |
| TGSSSNIGSNAVT (SEQ ID NO: 134) | DDNHRPS (SEQ ID NO: 142) | GAWDYSLNAYV (SEQ ID NO: 149) |
| SASSSNIGSNAVY (SEQ ID NO: 135) | SDNQRPS (SEQ ID NO: 143) | GSWDYSLSAYV (SEQ ID NO: 147) |
| TGSSSNIGSNSVS (SEQ ID NO: 136) | DDNNRPS (SEQ ID NO: 144) | GAWDYSLSAYV (SEQ ID NO: 150) |
| TGSSSNIGNYYVY (SEQ ID NO: 137) | ANSHRPS (SEQ ID NO: 145) | GSWDDSLSAYV (SEQ ID NO: 151) |

In an embodiment, the polypeptide may be used as part of a heavy chain variable region or a light chain variable region of an anti-VEGF antibody in combination of two or more polypeptides.

For example, the polypeptide that is capable of functioning as a heavy chain variable region of an anti-VEGF antibody may comprise or consist essentially of an amino acid sequence selected from the group consisting of SEQ ID NOs: 109 to 113, which can function as CDR-H1; an amino acid sequence selected from the group consisting of SEQ ID NOs: 114 to 121, which can function as CDR-H2; and an amino acid sequence selected from the group consisting of SEQ ID NOs: 122 to 129, which can function as CDR-H3. For example, the polypeptide may comprise or consisting essentially of an amino acid sequence selected from the group consisting of SEQ ID NOs: 152 to 159.

In another example, the polypeptide that is capable of functioning as a light chain variable region of an anti-VEGF antibody may comprise or consist essentially of an amino acid sequence selected from the group consisting of SEQ ID NOs: 130 to 137, which can function as CDR-L1; an amino acid sequence selected from the group consisting of SEQ ID NOs: 138 to 145, which can function as CDR-L21 and an amino acid sequence selected from the group consisting of SEQ ID NOs: 146 to 151, which can function as CDR-L3. For example, the polypeptide may comprise or consisting essentially of an amino acid sequence selected from the group consisting of SEQ ID NOs: 160 to 167.

In another embodiment, the polypeptide may comprise a combination of (1) a polypeptide comprising or consisting essentially of an amino acid sequence selected from the group consisting of SEQ ID NOs: 109 to 113, which can function as CDR-H1, an amino acid sequence selected from the group consisting of SEQ ID NOs: 114 to 121, which can function as CDR-H2, and an amino acid sequence selected from the group consisting of SEQ ID NOs: 122 to 129, which can function as CDR-H3; and (2) a polypeptide comprising or consisting essentially of an amino acid sequence selected from the group consisting of SEQ ID NOs: 130 to 137, which can function as CDR-L1; an amino acid sequence selected from the group consisting of SEQ ID NOs: 138 to 145, which can function as CDR-L2 and an amino acid sequence selected from the group consisting of SEQ ID NOs: 146 to 151, which can function as CDR-L3. For example, the polypeptide may comprise a combination of a polypeptide comprising or consisting essentially of an amino acid sequence selected from the group consisting of SEQ ID NOs: 152 to 159; and a polypeptide comprising or consisting essentially of an amino acid sequence selected from the group consisting of SEQ ID NOs: 160 to 167;

TABLE 3

| Heavy chain variable region | Light chain variable region |
|---|---|
| EVQLLESGGGLVQPGGSLRLSCAASGFTFSGYAMSWVRQAPGKGLEWVSSIYSSSGSKYYADSVKGRFTISRDNSKNTLYLQMNSLRAEDTAVYYCARASSTCTRTWCSYDDAMDVWGQGTLVTVSS (SEQ ID NO: 152) | QSVLTQPPSASGTPGQRVTISCTGSSSNIGNNAVTWYQQLPGTAPKLLIYDDSHRPSGVPDRFSGSKSGTSASLAISGLRSEDEADYYCGTWDYSLSGYVFGGGTKLTVLG (SEQ ID NO: 160) |
| EVQLLESGGGLVQTGGSLRLSCAASGFTFSDYAMSWVRQAPGKGLEWVSSIYPGSGSKYYADSVKGRFAISRDNSKNTLYLQMNSLRAEDTAVYYCARDAWFRGHNVFDYWGQGTLVTVSS (SEQ ID NO: 153) | QSVLTQPPSASGTPGQRVTISCTGSSSNIGSNNVTWYQQLPGTAPKLLIYSDSHRPSGVPDRFSGSKSGTSASLAISGLQSEDEADYYCGSWDYSLSAYVFGGGTKLTVLG (SEQ ID NO: 161) |

TABLE 3-continued

| Heavy chain variable region | Light chain variable region |
|---|---|
| EVQLLESGGGLVQPGGSLRLSCAASGFTFS<u>NYDM</u><br><u>S</u>WVRQAPGKGLEWVS<u>GIYPNGGSKYYADSVKGRF</u><br>TISRDNSKNTLYLQMNSLRAEDTAVYYCAR<u>ALRQ</u><br><u>CQRYWCSYADGMDV</u>WGQGTLVTVSS<br>(SEQ ID NO: 154) | QSVLTQPPSASGTPGQRVTISC<u>TGSSSNIGSNYVS</u><br>WYQQLPGTAPKLLIY<u>ADSQRP</u>SGVPDRFSGSKSGT<br>SASLAISGLRSEDEADYYC<u>GTWDYSLSGYVL</u>GGGT<br>KLTVLG<br>(SEQ ID NO: 162) |
| EVQLLESGGGLVQPGGSLRLSCAASGFTFS<u>DYYM</u><br><u>S</u>WVRQAPGKGLEWVS<u>AIYSGGGSIYYADSVKGRF</u><br>TISRDNSKNTLYLQMNSLRAEDTAVYYCAR<u>DVQW</u><br><u>NKAPRFDY</u>WGQGTLVTVSS<br>(SEQ ID NO: 155) | QSVLTQPPSASGAPGQRVTISC<u>SGSSSNIGSNDVS</u><br>WYQQLPGTAPKLLIY<u>ADSNRP</u>SGVPDRFSGSKSGT<br>SASLAISGLRSEDEADYYC<u>GSWDYSLSGYV</u>FGGGT<br>KLTVLG<br>(SEQ ID NO: 163) |
| EVQLLESGGGLVQPGGSLRLSCAASGFTFS<u>SYSM</u><br><u>S</u>WVRQAPGKGLEWVS<u>GISHGGGNKYYADSVKGRF</u><br>TISRDNSKNTLYLQMNSLRAEDTAVYYCAR<u>DLRA</u><br><u>NNDTGFDY</u>WGQGTLVTVSS<br>(SEQ ID NO: 156) | QSVLTQPPSSSGTPGQRVTISC<u>TGSSSNIGSNAVT</u><br>WYQQLPGTAPKLLIY<u>DDNHRP</u>SGVPDRFSGSKSGT<br>SASLAISGLRSEDEADYYC<u>GAWDYSLNAYV</u>FGGGT<br>KLTVLG<br>(SEQ ID NO: 164) |
| EVQLLESGGGLVQPGGSLRLSCAASGFTFS<u>NYDM</u><br><u>S</u>WVRQAPGKGLEWVS<u>LISHGGGNIYYADSVKGRF</u><br>TISRDNSKNTLYLQMNSLRAEDTAVYYCAR<u>VPVM</u><br><u>CTNHWCSYANGMDV</u>WGQGTLVTVSS<br>(SEQ ID NO: 157) | QSVLTQPPSASGTPGQRVIISC<u>SASSSNIGSNAVY</u><br>WYQQLPGTAPKLLIY<u>SDNQRP</u>SGVPDRFSGSKSGT<br>SASLAISGLRSEDEADYYC<u>GSWDYSLSAYV</u>FGGGT<br>KLTVLG<br>(SEQ ID NO: 165) |
| EVQLLESGGGLVQPGGSLRLSCAASGFTFS<u>GYAM</u><br><u>S</u>WVRQAPGKGLEWVS<u>GISHDGGNTYYADSVKGRF</u><br>TISRDNSKNTLYLQMNSLRAEDTAVYYCAR<u>DRRK</u><br><u>GPSTEFDY</u>WGQGTLVTVSS<br>(SEQ ID NO: 158) | QSVLTQPPSLSGTPGQRVTISC<u>TGSSSNIGSNSVS</u><br>WYQQLPGTAPKLLIY<u>DDNNRP</u>SGVPDRFSGSKSGT<br>SASLAISGLRSEDEADYYC<u>GAWDYSLSAYV</u>FGGGT<br>KLTVLG<br>(SEQ ID NO: 166) |
| EVQLLESGGGLVQTGGSLRLSCAASGFTFS<u>DYAM</u><br><u>S</u>WVRQAPGKGLEWVS<u>WIYPGDSSIYYADSVKGRF</u><br>TISRDNSKNTLYLQMNSLRAEDTAVYYCAR<u>LLSI</u><br><u>DQAQLHYYYDAMDV</u>WGQGTLVTVSS<br>(SEQ ID NO: 159) | QSVLTQPPSPSGTPGQRVTISC<u>TGSSSNIGNYYVS</u><br>WYQQLPGTAPKLLIY<u>ANSHRP</u>SGVPDRFSGSKSGT<br>SASLAISGLRSEDEADYYC<u>GSWDDSLSAYV</u>FGGGT<br>KLTVLG<br>(SEQ ID NO: 167) |

In another embodiment, the polypeptide may comprise or consist essentially of an amino acid sequence selected from the group consisting of one selected from SEQ ID NOs: 168 to 175:

(E1; 253a.a.)
SEQ ID NO: 168
EVQLLESGGGLVQPGGSLRLSCAASGFTFS<u>GYAM</u><u>S</u>WVRQAPGKGLEWVS<u>SIYSSSGSKYYADSVKGRF</u>TISRDNSKNTLYLQMNSLRAEDTAVYYCAR<u>ASSTCTRTWCSYDDAMDV</u>WGQGTLVTVSSGGGGSGGGGSGGGGSQSVLTQPPSASGTPGQRVTISC<u>TGSSSNIGNNAVT</u>WYQQLPGTAPKWY<u>DDSHRP</u>SGVPDRFSGSKSGTSASLAISGLRSEDEADYYC<u>GTWDYSLSGYV</u>FGGGTKLTVLG (E2; (247 a.a.)
SEQ ID NO: 169
EVQLLESGGGLVQTGGSLRLSCAASGFTFS<u>DYAM</u><u>S</u>WVRQAPGKGLEWVS<u>SIYPGSGSKYYADSVKGRF</u>AISRDNSKNTLYLQMNSLRAEDTAVYYCAR<u>DAWFRGHNVFDY</u>WGQGTLVTVSSGGGGSGGGGSGGGGSQSVLTQPPSASGTPGQRVTISC<u>TGSSSNIGSNNVT</u>WYQQLPGTAPKLLIY<u>SDSHRP</u>SGVPDRFSGSKSGTSASLAISGLQSEDEADYYC<u>GSWDYSLSAYV</u>FGGGTKLTVLG (E3; 253 a.a.)
SEQ ID NO: 170
EVQLLESGGGLVQPGGSLRLSCAASGFTFS<u>NYDM</u><u>S</u>WVRQAPGKGLEWVS<u>GIYPNGGSKYYADSVKGRF</u>TISRDNSKNTLYLQMNSLRAEDTAVYYCAR<u>ALRQCQRYWCSYADGMDV</u>WGQGTLVTVSSGGGGSGGGGSGGGGSQSVLTQPPSASGTPGQRVTISC<u>TGSSSNIGSNYVS</u>WYQQLPGTAPKLLIY<u>ADSQRP</u>SGVPDRFSGSKSGTSASLAISGLRSEDEADYYC<u>GTWDYSLSGYVL</u>GGGTKLTVLG (E5; 247 a.a.)
SEQ ID NO: 171
EVQLLESGGGLVQPGGSLRLSCAASGFTFS<u>DYYM</u><u>S</u>WVRQAPGKGLEWVS<u>AIYSGGGSIYYADSVKGRF</u>TISRDNSKNTLYLQMNSLRAEDTAVYYCAR<u>DVQWNKAPRFDY</u>WGQGTLVTVSSGGGGSGGGGSGGGGSQSVLTQPPSASGAPGQRVTISC<u>SGSSSNIGSNDVS</u>WYQQLPGTAPKLLIY<u>ADSNRP</u>SGVPDRFSGSKSGTSASLAISGLRSEDEADYYC<u>GSWDYSLSGYV</u>FGGGTKLTVLG (E7; 247 a.a.)
SEQ ID NO: 172
EVQLLESGGGLVQPGGSLRLSCAASGFTFS<u>SYSM</u><u>S</u>WVRQAPGKGLEWVS<u>GISHGGGNKYYADSVKGRF</u>TISRDNSKNTLYLQMNSLRAEDTAVYYCAR<u>DLRANNDTGFDY</u>WGQGTLVTVSSGGGGSGGGGSGGGGTQSVLTQPPSSSGTPGQRVTISC<u>TGSSSNIGSNAVT</u>WYQQLPGTAPKLLIY<u>DDNHRP</u>SGVPDRFSGSKSGTSASLAISGLRSEDEADYYC<u>GAWDYSLNAYV</u>FGGGTKLTVLG

-continued (E10; 253 a.a.)
SEQ ID NO: 173
EVQLLESGGGLVQPGGSLRLSCAASGFTFS<u>NYDMS</u>WVRQAPGKGLEWVS <u>LISHGGGNIYYADSVKG</u>RFTISRDNSKNTLYLQMNSLRAEDTAVYYCAR <u>VPVMCTNHWCSYANGMDV</u>WGQGTLVTVSSGGGGSGGGGSGGGGSQSVLT QPPSASGTPGQRVIISC<u>SASSSNIGSNAVY</u>WYQQLPGTAPKLLIY<u>SDNQ</u>

<u>RPS</u>GVPDRFSGSKSGTSASLAISGLRSEDEADYYC<u>GSWDYSLSAYV</u>FGG

GTKLTVLG (E11; 247 a.a.)
SEQ ID NO: 174
EVQLLESGGGLVQPGGSLRLSCAASGFTFS<u>GYAMS</u>WVRQAPGKGLEWVS

<u>GISHDGGNTYYADSVKG</u>RFTISRDNSKNTLYLQMNSLRAEDTAVYYCAR

<u>DRRKGPSTEFDYW</u>GQGTLVTVSSGGGGSGGGGSGGGGSQSVLTQPPSLS

GTPGQRVTISC<u>TGSSSNIGSNSVS</u>WYQQLPGTAPKLLIY<u>DDNNRPS</u>GVP

DRFSGSKSGTSASLAISGLRSEDEADYYC<u>GAWDYSLSAYV</u>FGGGTKLTV

LG (E12; 253 a.a.)
SEQ ID NO: 175
EVQLLESGGGLVQTGGSLRLSCAASGFTFS<u>DYAMS</u>WVRQAPGKGLEWVS

<u>WIYPGDSSIYYADSVKG</u>RFTISRDNSKNTLYLQMNSLRAEDTAVYYCAR

<u>LLSIDQAQLHYYYDAMDV</u>WGQGTLVTVSSGGGGSGGGGSGGGGSQSVLT

QPPSPSGTPGQRVTISC<u>TGSSSNIGNYYVY</u>WYQQLPGTAPKLLIY<u>ANSH</u>

<u>RPS</u>GVPDRFSGSKSGTSASLAISGLRSEDEADYYC<u>GSWDDSLSAYV</u>FGG

GTKLTVLG (in SEQ ID NOs: 168 to 175, CDR-H1, CDR-H2, CDR-H3, CDR-L1, CDR-L2, and CDR-L3 are underlined in order from the N-terminus)

The polypeptide may be non-naturally occurring. For example, the polypeptide may be synthetic or recombinant.

The polypeptide may function as an antigen-binding fragment, for example an scFv fragment, of an anti-VEGF antibody.

The polypeptide may act as a precursor or a component of a VEGF antagonist, such as an anti-VEGF antibody, an antigen-binding fragment thereof, or an anti-VEGF antibody analog (e.g., a peptibody, nanobody, etc.).

Therefore, another embodiment provides a VEGF antagonist including the polypeptide. The antagonist may be any agent (e.g., a compound, a protein, a peptide, etc.) capable of inhibiting the VEGF activity, and may be one or more selected from the group consisting of an anti-VEGF antibody, an antigen-binding fragment thereof, an anti-VEGF antibody analogue (e.g., a peptibody, nanobody, etc.), and the like.

The term "antagonist" may include any molecule capable of completely or partially preventing, inhibiting, or neutralizing one or more biological activities of a target (e.g., VEGF). For instance, an antibody as an antagonist may refer to an antibody capable of inhibiting or lowering biological activities of an antigen (e.g., VEGF) to which the antibody binds. The antagonist may bind to a receptor for a ligand (target) to decrease receptor phosphorylation, or incapacitating or killing a cell that is activated by the ligand. In addition, the antagonist may substantially decrease an interaction between a receptor and its ligand, by completely blocking the receptor-ligand interaction, binding to the receptor competitively with its ligand, or modifying or down-regulating three-dimensional structure of the receptor.

The term "peptibody (peptide+antibody)" may refer to a fusion protein wherein a peptide is fused with the whole or a part of a constant region of an antibody, such as Fc region, and the peptide acts as an antigen-binding region (e.g., a CDR or variable region of a heavy chain and/or light chain), thereby having a structure and functions similar to an antibody.

The term "nanobody," which is also known as a single-domain antibody, may refer to an antibody fragment, including a single variable domain in a monomeric form, that selectively binds to a specific antigen, similar to an antibody in a complete form. The nanobody usually has a molecular weight of about 12 kDa to about 15 kDa, which is much smaller than the general molecular weight (about 150 kDa to about 160 kDa) of an antibody in a complete form (including two heavy chains and two light chains), and in some cases, smaller than a molecular weight of a Fab fragment or a scFv fragment.

In a particular embodiment, the polypeptide may act as a precursor or a component of an anti-VEGF antibody.

Another embodiment provides an anti-VEGF antibody or an antigen-binding fragment thereof including the polypeptide. The antigen-binding fragment may be selected from the group consisting of scFv, (scFv)2, scFv-Fc, Fab, Fab' and F(ab')2.

In particular, the anti-VEGF antibody or an antigen-binding fragment thereof may comprise or consist essentially of:

at least one heavy chain complementarity determining region selected from the group consisting of a CDR-H1 comprising or consisting essentially of an amino acid sequence selected from SEQ ID NOs: 109 to 113, a CDR-H2 comprising or consisting essentially of an amino acid sequence selected from SEQ ID NOs: 114 to 121, and a CDR-H3 comprising or consisting essentially of an amino acid sequence selected from SEQ ID NOs: 122 to 129, or a heavy chain variable region comprising the at least one heavy chain complementarity determining region;

at least one light chain complementarity determining region selected from the group consisting of a CDR-L1 comprising or consisting essentially of an amino acid sequence selected from SEQ ID NOs: 130 to 137, a CDR-L2 comprising or consisting essentially of an amino acid sequence selected from SEQ ID NOs: 138 to 145, and a CDR-L3 comprising or consisting essentially of an amino acid sequence selected from SEQ ID NOs: 146 to 151, and a heavy light variable region comprising the at least one light chain complementarity determining region;

a combination of the at least one heavy chain complementarity determining region and the at least one light chain complementarity determining region; or a combination of the heavy chain variable region and the light chain variable region.

For example, the anti-VEGF antibody or an antigen-binding fragment thereof may comprise or consist essentially of a heavy chain variable region comprising or consisting essentially of an amino acid sequence of SEQ ID NOs: 152 to 159, a light chain variable region comprising or consisting essentially of an amino acid sequence of SEQ ID NOs: 160 to 167, or a combination thereof.

In a particular embodiment, the anti-VEGF antibody or an antigen-binding fragment thereof may be an anti-VEGF scFv comprising or consisting essentially of a heavy chain variable region comprising or consisting essentially of an amino acid sequence of SEQ ID NOs: 152 to 159 and a light chain variable region comprising or consisting essentially of an amino acid sequence of SEQ ID NOs: 160 to 167.

In a particular embodiment, the anti-VEGF antibody or an antigen-binding fragment thereof may be an anti-VEGF scFv comprising or consisting essentially of an amino acid sequence selected from SEQ ID NOs: 168 to 175.

In an antigen-binding fragment of the anti-VEGF antibody, for example, an anti-VEGF scFv, the heavy chain variable region and the light chain variable region may be linked with or without a linker (e.g., a peptide linker). The peptide linker may be those having 1 to 100 amino acids, particularly 2 to 50 amino acids, and any kinds of amino acids may be included provided they have no effect on the function of the antigen-binding fragment of the anti-VEGF antibody. The peptide linker may include, for example, Gly, Asn and/or Ser residues, and/or include neutral amino acids such as Thr and/or Ala. Amino acid sequences suitable for the peptide linker may be those known in the relevant art. Meanwhile, a length of the peptide linker may be variously determined within such a limit that the functions of the antigen-binding fragment of the anti-VEGF antibody will not be affected. For instance, the peptide linker may be formed by including a total of about 1 to about 100, about 2 to about 50, or about 5 to about 25 amino acids, each of which may be independently selected from the group consisting of Gly, Asn, Ser, Thr, and Ala. In one embodiment, the peptide linker may be represented as $(GGGGS)_n$ (n is an integer of about 1 to about 10, particularly an integer of about 2 to about 5).

As used herein, the term "antibody" may refer to not only a complete form of an immunoglobulin (e.g., a full-length IgA, IgD, IgE, IgG (IgG1, IgG2, IgG3, or IgG4), IgM, etc.) but also an antigen-binding fragment of an antibody which possesses the antigen-binding affinity of the antibody. The "complementarity-determining region (CDR)" may refer to a region within a variable region, which gives the binding specificity to an antigen. The antigen-binding fragment as described above may be an antibody fragment including at least one complementarity-determining region, for example, one or more selected from the group consisting of scFv, (scFv)2, scFv-Fc, Fab, Fab', and F(ab')2.

In the anti-VEGF antibody or an antigen-binding fragment thereof, the frameworks, light chain constant region and a heavy chain constant region, (i.e., the light chain and the heavy chain portions excluding the CDRs and the variable regions), may be from any subtype of immunoglobulin (e.g., IgA, IgD, IgE, IgG (IgG1, IgG2, IgG3, IgG4), IgM, and the like).

Based on the ability of specifically binding to VEGF and inhibiting the activity thereof, the anti-VEGF antibody or an antigen-binding fragment thereof may be used in preventing and/or treating a VEGF-associated disease. Therefore, one embodiment provides a pharmaceutical composition for preventing and/or treating a VEGF-associated disease (e.g., a disease associated with abnormal activation and/or overproduction (overexpression) of VEGF), comprising the anti-VEGF antibody or an antigen-binding fragment thereof. Another embodiment provides a method of preventing and/or treating a VEGF-associated disease (e.g., a disease associated with abnormal activation and/or overproduction (overexpression) of VEGF) in a subject, comprising administering the anti-VEGF antibody or an antigen-binding fragment thereof to the subject, who is in need of prevention and/or treatment of the VEGF-associated disease. In the composition and the method, the anti-VEGF antibody or an antigen-binding fragment thereof may be used in a pharmaceutically effective amount to treat and/or prevent the diseases. The VEGF-associated disease (e.g., a disease associated with abnormal activation and/or overproduction (overexpression) of VEGF) may be a cancer, details of which are described below.

Based on the ability of specifically binding to VEGF, the anti-VEGF antibody or an antigen-binding fragment thereof may be used in detecting VEGF or identifying activation and/or overproduction (i.e. overexpression) of VEGF.

One embodiment provides a composition for detecting the presence of VEGF including the anti-VEGF antibody or an antigen-binding fragment thereof. Another embodiment provides a method of detecting VEGF including treating a biological sample with the anti-VEGF antibody or an antigen-binding fragment thereof; and detecting an antigen-antibody reaction (binding). In the method of detecting, when an antigen-antibody reaction is detected, it can be determined that VEGF is present in the biological sample and when an antigen-antibody reaction is not detected, it can be determined that VEGF is absent (not present) in the biological sample. In another embodiment, the degree of expression of VEGF and/or the level of VEGF may be determined according to the level of the antigen-antibody reaction (e.g., the amount of antigen-antibody complex formed by the antigen-antibody reaction, the intensity of any conventional signal obtained by the antigen-antibody reaction, and the like, which can be routinely measured by any conventional means). The biological sample may be selected from the group consisting of a cell, a tissue, body fluid (e.g., blood, serum, etc.), and the like obtained from a mammal including primates such as a human, a monkey, and the like, or a rodent such as a mouse, a rat, and the like. The biological sample may be separated from a living body. The detection of VEGF may refer to determination of presence or absence of VEGF, expression of VEGF, or the level of VEGF.

Another embodiment provides a pharmaceutical composition for diagnosing abnormal activation (e.g., abnormal activation or over-activation) and/or overproduction of VEGF or a disease associated with activation (e.g., abnormal activation or over-activation) and/or overproduction of VEGF comprising the anti-VEGF antibody or an antigen-binding fragment thereof. Another embodiment provides a method of diagnosing (or determining) activation (e.g., abnormal activation or over-activation) and/or overproduction of VEGF or a disease associated with activation and/or overproduction of VEGF, wherein the method comprises treating a biological sample obtained from a patient with the anti-VEGF antibody or an antigen-binding fragment thereof, and measuring a level of an antigen-antibody reaction. In this method, when the level of the antigen-antibody reaction in the biological sample is higher than that of a normal sample, the patient from which the biological sample is obtained may be determined as having activation (e.g., abnormal activation or over-activation) and/or overproduction of VEGF or a disease associated with activation and/or overproduction of VEGF. Therefore, the method may further include treating a normal sample with the anti-VEGF antibody or an antigen-binding fragment thereof, and measuring a level of an antigen-antibody reaction. In another embodiment, provided is a use of the anti-VEGF antibody or an antigen-binding fragment thereof for diagnosing (or determining) activation (e.g., abnormal activation or over-activation) and/or overproduction of VEGF or a disease associated with activation and/or overproduction of VEGF.

The biological sample may be at least one selected from the group consisting of a cell, a tissue, body fluid (e.g., blood, serum, lymph, etc.) and the like, obtained from a patient to be diagnosed. The biological sample may be separated from a living body. The normal sample may be at least one selected from the group consisting of a cell, a tissue, body fluid (e.g., blood, serum, lymph, etc.) and the like, obtained from a patient having no condition of activation and/or overproduction of VEGF or a disease associated with activation and/or overproduction of VEGF. The normal sample may be separated from a living body. The patient may be selected from a mammal, including primates such as a human, a monkey, and the like, and rodents such as a mouse, a rat, and the like.

The step of measuring a level of an antigen-antibody reaction may be performed by any general method known to the relevant art, such as general enzymatic reactions, fluorescent reactions, luminescent reactions, and/or detection of radiation. For example, the step may be performed by a method selected from, but not limited to, the group consisting of immunochromatography, immunohistochemistry (IHC), enzyme linked immunosorbent assay (ELISA), radioimmunoassay (RIA), enzyme immunoassay (EIA), fluorescence immunoassay (FIA), luminescence immunoassay (LIA), western blotting, microarray, flow cytometry, surface plasmon resonance (SPR), and the like.

The polypeptides capable of functioning as CDRs or a heavy chain variable region and a light chain variable region of an anti-VEGF antibody may be used in preparing various multispecific (e.g., bispecific) antibodies recognizing VEGF and other antigen(s), as well as a monospecific anti-VEGF antibody.

Another embodiment provides an anti-c-Met/anti-VEGF bispecific antibody comprising an anti-c-Met antibody or an antigen-binding fragment thereof and an anti-VEGF antibody or an antigen-binding fragment thereof. The antigen-binding fragment thereof may be selected from the group consisting of scFv, (scFv)2, scFvFc, Fab, Fab', and F(ab')2 of an antibody.

The "c-Met protein" refers to a receptor tyrosine kinase binding to hepatocyte growth factor. The c-Met protein may be derived (obtained) from any species, for example, those derived (obtained) from primates such as human c-Met (e.g., NP_000236.2) and monkey c-Met (e.g., *Macaca mulatta*, NP_001162100.1), or those derived (obtained) from rodents such as mouse c-Met (e.g., NP_032617.2) and rat c-Met (e.g., NP 113705.1). The proteins include, for example, a polypeptide encoded by the nucleotide sequence deposited under GenBank Accession Number NM_000245.2, or a protein encoded by the polypeptide sequence deposited under GenBank Accession Number NM_000236.2, or extracellular domains thereof. The receptor tyrosine kinase c-Met is involved in several mechanisms including cancer incidence, cancer metastasis, cancer cell migration, cancer cell penetration, angiogenesis, etc.

A vascular endothelial growth factor (VEGF) is a signal protein produced by cells that stimulates vasculogenesis and angiogenesis. VEGF's normal function is to create new blood vessels during embryonic development, new blood vessels after injury, muscle following exercise, and new vessels (collateral circulation) to bypass blocked vessels. When VEGF is overexpressed, it can contribute to disease. In particular, it is secreted from a cancer cell and binds to its receptor, VEGF Receptor (VEGFR), to induce angiogenesis, whereby the cancer cell is supplied with nutrients necessary for cell proliferation from the produced novel blood vessel. Overexpression of VEGF can cause various disease such as cancer and/or vascular disease in the retina of the eye, and participate in not only carcinogenesis but also poor prognosis of cancer such as invasion or metastasis of cancer. Therefore, VEGF may serve as a target for anticancer therapy.

The VEGF may be obtained from mammals including primates such as human, monkey, etc., rodents such as mouse, rat, etc., and the like. For example, the VEGF protein may be a polypeptide encoded by a nucleotide sequence (mRNA) selected from the group consisting of GenBank Accession Numbers NM_001025366.2 (VEGF-A), NM_001025367.2 (VEGF-A), NM_001025368.2, NM_001025369.2, NM_001025370.2, NM_001033756.2, NM_001171622.1, NM_001171623.1, NM_001171624.1, NM_001171625.1, NM_001171626.1, NM_001171627.1, NM_001171628.1, NM_001171629.1, NM_001171630.1, NM_001204384.1, NM_001204385.1, NM_003376.5, etc., but not be limited thereto.

In one embodiment, the anti-c-Met/anti-VEGF bispecific antibody may include an anti-c-Met antibody or an antigen binding fragment thereof, and an anti-VEGF antibody or an antigen binding fragment thereof which is linked to the C terminus or N terminus of the c-Met antibody or antigen binding fragment thereof. For example, the anti-c-Met/anti-VEGF bispecific antibody may include an anti-c-Met antibody or an antigen binding fragment thereof, and an anti-VEGF antibody or an antigen binding fragment thereof which is linked to the C terminus of a heavy chain of the c-Met antibody (e.g., in a IgG form).

In the anti-c-Met/anti-VEGF bispecific antibody, in order to fully perform the anti-c-Met antibody's activity to mediate intracellular migration and degradation of c-Met proteins, it may be advantageous that the anti-c-Met antibody has its own intact (full length) antibody structure. In addition, in case of the anti-VEGF antibody, its specific recognition and binding to VEGF is important, and thus it will be fine (sufficient) that just an antigen-binding fragment recognizing VEGF is included in the bispecific antibody. Therefore, the anti-c-Met/anti-VEGF bispecific antibody may comprise a complete form (e.g., comprising full length heavy chain and full length light chain) of an anti-c-Met antibody (e.g., full length antibody in IgG form) and an antigen-binding fragment (e.g., scFv, (scFv)2, scFv-Fc, Fab, Fab', or F(ab')2) of the anti-VEGF antibody linked to the C terminus of the anti-c-Met antibody (heavy chain).

In an embodiment, the an anti-c-Met/anti-VEGF bispecific antibody may be an antibody, which comprises a first polypeptide comprising a heavy chain of an anti-c-Met antibody in IgG form and an antigen-binding fragment (e.g., scFv fragment) of an anti-VEGF antibody linked to the c-terminus of the heavy chain of the in IgG form, and a second polypeptide comprising a light chain of the anti-c-Met antibody in IgG form (see FIG. 1).

In the anti-c-Met/anti-VEGF bispecific antibody, the anti-c-Met antibody or the antigen binding fragment thereof, and the anti-VEGF antibody or the antigen binding fragment thereof, may be linked via a peptide linker, or they may be linked directly and without a linker. Furthermore, a heavy chain portion and a light chain portion within the antigen binding fragment, for example, a heavy chain variable region and a light chain variable region within the scFv fragment, may be linked via a peptide linker or directly without a linker. The peptide linker which links the anti-c-Met antibody or the antigen binding fragment thereof and the anti-VEGF antibody or the antigen binding fragment thereof, and the peptide linker which links the heavy chain portion and the light chain portion within the antigen binding fragment, may be identical or different. The peptide linker may be include about 1 to about 100 amino acid residues, particularly about 2 to about 50, and any kinds of amino acids may be included without any restrictions. The peptide linker may include for example, Gly, Asn and/or Ser residues, and also include neutral amino acids such as Thr and/or Ala. Amino acid sequences suitable for the peptide linker may be those known in the pertinent art. Meanwhile, a length of the peptide linker may be variously determined within such a limit that the functions of the bispecific antibody will not be affected. For instance, the peptide linker may be formed by including a total of about 1 to about 100, about 2 to about 50, or about 5 to about 25 of one or more selected from the group consisting of Gly, Asn, Ser, Thr, and Ala. In one embodiment, the peptide linker may be represented as $(GGGGS)_n$ (n is an integer of about 1 to about 10, particularly an integer of about 2 to about 5).

In an embodiment, an anti-VEGF antibody or an antigen-binding fragment thereof comprised in an anti-c-Met/anti-VEGF bispecific antibody may comprise or consist essentially of:

at least one heavy chain complementarity determining region selected from the group consisting of a CDR-H1 comprising or consisting essentially of an amino acid sequence selected from SEQ ID NOs: 109 to 113, a CDR-H2 comprising or consisting essentially of an amino acid sequence selected from SEQ ID NOs: 114 to 121, and a CDR-H3 comprising or consisting essentially of an amino acid sequence selected from SEQ ID NOs: 122 to 129, or a heavy chain variable region comprising the at least one heavy chain complementarity determining region;

at least one light chain complementarity determining region selected from the group consisting of a CDR-L1 comprising or consisting essentially of an amino acid sequence selected from SEQ ID NOs: 130 to 137, a CDR-L2 comprising or consisting essentially of an amino acid sequence selected from SEQ ID NOs: 138 to 145, and a CDR-L3 comprising or consisting essentially of an amino acid sequence selected from SEQ ID NOs: 146 to 151, and a heavy light variable region comprising the at least one light chain complementarity determining region;

a combination of the at least one heavy chain complementarity determining region and the at least one light chain complementarity determining region; or a combination of the heavy chain variable region and the light chain variable region.

The "antigen binding fragment" refers to a fragment of a full immunoglobulin structure, which includes a portion capable of binding to an antigen. For example, it may be scFv, $(scFv)_2$, scFv-Fc, Fab, Fab', or $F(ab')_2$, but not be limited thereto. In the present invention, the antigen binding fragment may be an antibody fragment including at least one complementarity determining region, for example, selected from the group consisting of scFv, (scFv)2, scFv-Fc, Fab, Fab' and F(ab')2.

Of the antigen binding fragments, Fab is a structure having variable regions of a light chain and a heavy chain, a constant region of the light chain, and the first constant region ($C_{H1}$) of the heavy chain, and it has one antigen binding site.

Fab' is different from Fab in that it has a hinge region including one or more cysteine residues at the C-terminal of heavy chain $C_{H1}$ domain. An $F(ab')_2$ antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof. The peptide linker may be the same as described in the above, and for example, comprise a total of about 1 to about 100, about 2 to about 50, or about 5 to about 25 of amino acids.

The antigen binding fragments may be obtained using proteases (for example, a whole antibody is digested with papain to obtain Fab fragments, and is digested with pepsin to obtain $F(ab')_2$ fragments), and may be prepared by a genetic recombinant technique.

In an embodiment, the anti-c-Met/anti-VEGF bispecific antibody may comprise an anti-c-Met antibody, and scFv, $(scFv)_2$, Fab, Fab' or $F(ab')_2$, for example, scFv, of an anti-VEGF antibody linked to the C terminus of the anti-c-Met antibody.

For instance, the anti-VEGF antibody or an antigen-binding fragment thereof may comprise a heavy chain variable region comprising or consisting essentially of an amino acid sequence selected from SEQ ID NOs: 152 to 159, a light chain variable region comprising or consisting essentially of an amino acid sequence selected from SEQ ID NOs: 160 to 167, or a combination thereof.

In an embodiment, the anti-VEGF antibody or an antigen-binding fragment thereof may be an anti-VEGF scFv comprising or consisting essentially of an amino acid sequence selected from SEQ ID NOs: 168 to 175.

In an embodiment, the anti-c-Met/anti-VEGF bispecific antibody may comprise:

(1) an anti-c-Met antibody, and (2) a heavy chain variable region of an anti-VEGF antibody comprising or consisting essentially of an amino acid sequence selected from SEQ ID NOs: 152 to 159, a light chain variable region of an anti-VEGF antibody comprising or consisting essentially of an amino acid sequence selected from SEQ ID NOs: 160 to 167, or a combination thereof, which is linked to the C-terminus of the anti-c-Met antibody.

In another embodiment, the anti-c-Met/anti-VEGF bispecific antibody may comprise:

(1) an anti-c-Met antibody, and (2) an anti-VEGF scFv comprising or consisting essentially of an amino acid sequence selected from SEQ ID NOs: 168 to 175, which is linked to the C-terminus of the anti-c-Met antibody.

The anti-c-Met antibody may be any one recognizing a specific region of c-Met, e.g., a specific region in the SEMA domain, as an epitope. It may be any antibody or antigen-binding fragment that acts on c-Met to induce intracellular internalization and degradation of c-Met.

c-Met, a receptor for hepatocyte growth factor (HGF), may be divided into three portions: extracellular, transmembrane, and intracellular. The extracellular portion is composed of an α-subunit and a (3-subunit which are linked to each other through a disulfide bond, and contains a SEMA domain responsible for binding HGF, a PSI domain (plexin-semaphorin-integrin homology domain) and an IPT domain (immunoglobulin-like fold shared by plexins and transcriptional factors domain). The SEMA domain of c-Met protein may have the amino acid sequence of SEQ ID NO: 79, and is an extracellular domain that functions to bind HGF. A specific region of the SEMA domain, that is, a region including the amino acid sequence of SEQ ID NO: 71, which corresponds to a range from amino acid residues 106 to 124 of the amino acid sequence of the SEMA domain (SEQ ID NO: 79) of c-Met protein, is a loop region between the second and the third propellers within the epitopes of the SEMA domain. The region acts as an epitope for the specific anti-c-Met antibody of the present invention.

The term "epitope" as used herein, refers to an antigenic determinant, a part of an antigen recognized by an antibody.

In one embodiment, the anti-c-Met antibody may specifically bind to an epitope which has about 5 or more contiguous (consecutive or non-consecutive) amino acid residues within the SEMA domain (SEQ ID NO: 79) of c-Met protein, for instance, about 5 to about 19 contiguous amino acid residues within the amino acid sequence of SEQ ID NO: 71. For example, the epitope may be a polypeptide having about 5 to about 19 contiguous amino acids selected from among partial combinations of the amino acid sequence of SEQ ID NO: 71, wherein the polypeptide essentially includes the amino sequence of SEQ ID NO: 73 (EEPSQ) serving as an essential element for the epitope. For example, the epitope may be a polypeptide including, consisting essentially of, or consisting of the amino acid sequence of SEQ ID NO: 71, SEQ ID NO: 72, or SEQ ID NO: 73.

The epitope including the amino acid sequence of SEQ ID NO: 72 corresponds to the outermost part of the loop between the second and third propellers within the SEMA domain of a c-Met protein. The epitope including the amino acid sequence of SEQ ID NO: 73 is a site to which the antibody or antigen-binding fragment according to one embodiment most specifically binds.

In one embodiment, the anti-c-Met antibody or an antigen-binding fragment thereof may comprise or consist essentially of:

at least one heavy chain complementarity determining region (CDR) selected from the group consisting of (a) a CDR-H1 including the amino acid sequence of SEQ ID NO: 4; (b) a CDR-H2 including the amino acid sequence of SEQ ID NO: 5, SEQ ID NO: 2, or an amino acid sequence having about 8-19 consecutive amino acids within SEQ ID NO: 2 including amino acid residues from the $3^{rd}$ to $10^{th}$ positions of SEQ ID NO: 2; and (c) a CDR-H3 including the amino acid sequence of SEQ ID NO: 6, SEQ ID NO: 85, or an amino acid sequence having about 6-13 consecutive amino acids within SEQ ID NO: 85 including amino acid residues from the $1^{st}$ to $6^{th}$ positions of SEQ ID NO: 85, or a heavy chain variable region including the at least one heavy chain complementarity determining region;

at least one light chain complementarity determining region (CDR) selected from the group consisting of (a) a CDR-L1 including the amino acid sequence of SEQ ID NO: 7, (b) a CDR-L2 including the amino acid sequence of SEQ ID NO: 8, and (c) a CDR-L3 including the amino acid sequence of SEQ ID NO: 9, SEQ ID NO: 15, SEQ ID NO: 86, or an amino acid sequence having 9-17 consecutive amino acids within SEQ ID NO: 89 including amino acid residues from the $1^{st}$ to $9^{th}$ positions of SEQ ID NO: 89, or a light chain variable region including the at least one light chain complementarity determining region;

a combination of the at least one heavy chain complementarity determining region and at least one light chain complementarity determining region; or a combination of the heavy chain variable region and the light chain variable region.

Herein, the amino acid sequences of SEQ ID NOS: 4 to 9 are respectively represented by following Formulas I to VI, below:

Formula I (SEQ ID NO: 4)
$Xaa_1$-$Xaa_2$-Tyr-Tyr-Met-Ser, wherein $Xaa_1$ is absent or Pro or Ser, and $Xaa_2$ is Glu or Asp, Formula II (SEQ ID NO: 5)
Arg-Asn-$Xaa_3$-$Xaa_4$-Asn-Gly-$Xaa_5$-Thr, wherein $Xaa_3$ is Asn or Lys, $Xaa_4$ is Ala or Val, and $Xaa_5$ is Asn or Thr, Formula III (SEQ ID NO: 6)
Asp-Asn-Trp-Leu-$Xaa_6$-Tyr, wherein $Xaa_6$ is Ser or Thr, Formula IV (SEQ ID NO: 7)
Lys-Ser-Ser-$Xaa_7$-Ser-Leu-Leu-Ala-$Xaa_8$-Gly-Asn-$Xaa_9$-$Xaa_{10}$-Asn-Tyr-Leu-Ala wherein $Xaa_7$ is His, Arg, Gln, or Lys, $Xaa_8$ is Ser or Trp, $Xaa_9$ is His or Gln, and $Xaa_{10}$ is Lys or Asn, Formula V (SEQ ID NO: 8)
Trp-$Xaa_{11}$-Ser-$Xaa_{12}$-Arg-Val-$Xaa_{13}$ wherein $Xaa_{11}$ is Ala or Gly, $Xaa_{12}$ is Thr or Lys, and $Xaa_{13}$ is Ser or Pro, and Formula VI (SEQ ID NO: 9)
$Xaa_{14}$-Gln-Ser-Tyr-Ser-$Xaa_{15}$-Pro-$Xaa_{16}$-Thr wherein $Xaa_{14}$ is Gly, Ala, or Gln, $Xaa_{15}$ is Arg, His, Ser, Ala, Gly, or Lys, and $Xaa_{16}$ is Leu, Tyr, Phe, or Met.

In one embodiment, the CDR-H1 may include an amino acid sequence selected from the group consisting of SEQ ID NOS: 1, 22, 23, and 24. The CDR-H2 may include an amino acid sequence selected from the group consisting of SEQ ID NOS: 2, 25, and 26. The CDR-H3 may include an amino acid sequence selected from the group consisting of SEQ ID NOS: 3, 27, 28, and 85.

The CDR-L1 may include an amino acid sequence selected from the group consisting of SEQ ID NOS: 10, 29, 30, 31, 32, 33, and 106. The CDR-L2 may include an amino acid sequence selected from the group consisting of SEQ ID NOS: 11, 34, 35, and 36. The CDR-L3 may include an amino acid sequence selected from the group consisting of SEQ ID NOS: 12, 13, 14, 15, 16, 37, 86, and 89.

In another embodiment, the antibody or antigen-binding fragment may include a heavy chain variable region comprising a polypeptide (CDR-H1) including an amino acid sequence selected from the group consisting of SEQ ID NOS: 1, 22, 23, and 24, a polypeptide (CDR-H2) including an amino acid sequence selected from the group consisting of SEQ ID NOS: 2, 25, and 26, and a polypeptide (CDR-H3) including an amino acid sequence selected from the group consisting of SEQ ID NOS: 3, 27, 28, and 85; and a light chain variable region comprising a polypeptide (CDR-L1) including an amino acid sequence selected from the group consisting of SEQ ID NOS: 10, 29, 30, 31, 32, 33 and 106, a polypeptide (CDR-L2) including an amino acid sequence selected from the group consisting of SEQ ID NOS: 11, 34, 35, and 36, and a polypeptide (CDR-L3) including an amino acid sequence selected from the group consisting of SEQ ID NOS 12, 13, 14, 15, 16, 37, 86, and 89.

Animal-derived antibodies produced by immunizing non-immune animals with a desired antigen generally invoke immunogenicity when injected to humans for the purpose of medical treatment, and thus chimeric antibodies have been developed to inhibit such immunogenicity. Chimeric antibodies are prepared by replacing constant regions of animal-derived antibodies that cause an anti-isotype response with constant regions of human antibodies by genetic engineering. Chimeric antibodies are considerably improved in an anti-isotype response compared to animal-derived antibodies, but animal-derived amino acids still have variable regions, so that chimeric antibodies have side effects with respect to a potential anti-idiotype response. Humanized antibodies have been developed to reduce such side effects. Humanized antibodies are produced by grafting complementarity determining regions (CDR) which serve an important role in antigen binding in variable regions of chimeric antibodies into a human antibody framework.

The most important thing in CDR grafting to produce humanized antibodies is choosing the optimized human antibodies for accepting CDRs of animal-derived antibodies. Antibody databases, analysis of a crystal structure, and technology for molecule modeling are used. However, even when the CDRs of animal-derived antibodies are grafted to the most optimized human antibody framework, amino acids positioned in a framework of the animal-derived CDRs affecting antigen binding are present. Therefore, in many cases, antigen binding affinity is not maintained, and thus application of additional antibody engineering technology for recovering the antigen binding affinity is necessary.

The anti c-Met antibodies may be mouse-derived antibodies, mouse-human chimeric antibodies, humanized antibodies, or human antibodies. The antibodies or antigen-binding fragments thereof may be isolated from a living body or non-naturally occurring. The antibodies or antigen-binding fragments thereof may be synthetic or recombinant. The antibodies or antigen-binding fragments thereof may be monoclonal.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to full-length heavy chain, and fragments thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain and fragments thereof, including a variable region $V_L$ that includes amino acid sequences sufficient to provide specificity to antigens, and a constant region $C_L$.

The term "complementarity determining region (CDR)" refers to an amino acid sequence found in a hyper variable region of a heavy chain or a light chain of immunoglobulin.

The heavy and light chains may respectively include three CDRs (CDRH1, CDRH2, and CDRH3; and CDRL1, CDRL2, and CDRL3). The CDR may provide contact residues that play an important role in the binding of antibodies to antigens or epitopes. The terms "specifically binding" and "specifically recognized" are well known to one of ordinary skill in the art, and indicate that an antibody and an antigen specifically interact with each other to lead to an immunological activity.

The term "hinge region," as used herein, refers to a region between CH1 and CH2 domains within the heavy chain of an antibody which functions to provide flexibility for the antigen-binding site.

When an animal antibody undergoes a chimerization process, the IgG1 hinge of animal origin is replaced with a human IgG1 hinge or IgG2 hinge while the disulfide bridges between two heavy chains are reduced from three to two in number. In addition, an animal-derived IgG1 hinge is shorter than a human IgG1 hinge. Accordingly, the rigidity of the hinge is changed. Thus, a modification of the hinge region may bring about an improvement in the antigen binding efficiency of the humanized antibody. The modification of the hinge region through amino acid deletion, addition, or substitution is well-known to those skilled in the art.

In one embodiment, the anti-c-Met antibody or an antigen-binding fragment thereof may be modified by the deletion, insertion, addition, or substitution of at least one amino acid residue on the amino acid sequence of the hinge region so that it exhibit enhanced antigen-binding efficiency. For example, the antibody may include a hinge region including the amino acid sequence of SEQ ID NO: 100(U7-HC6), 101(U6-HC7), 102(U3-HC9), 103(U6-HC8), or 104(U8-HC5), or a hinge region including the amino acid sequence of SEQ ID NO: 105 (non-modified human hinge). In particular, the hinge region has the amino acid sequence of SEQ ID NO: 100 or 101.

In one embodiment, the anti-c-Met antibody or antigen-binding fragment may include a variable region of the heavy chain including the amino acid sequence of SEQ ID NO: 17, 74, 87, 90, 91, 92, 93, or 94, a variable region of the light chain including the amino acid sequence of SEQ ID NO: 190, 18, 19, 20, 21, 75, 88, 95, 96, 97, 98, 99, or 107, or a combination thereof.

In one embodiment, the anti-c-Met antibody may be a monoclonal antibody. The monoclonal antibody may be produced by the hybridoma cell line deposited with Accession No. KCLRF-BP-00220, which binds specifically to the extracellular region of c-Met protein (refer to Korean Patent Publication No. 2011-0047698, which is hereby incorporated by reference). The anti-c-Met antibody may include all the antibodies defined in Korean Patent Publication No. 2011-0047698.

In the anti-c-Met antibody, the rest portion of the light chain and the heavy chain portion except CDRs, a light chain variable region, and a heavy chain variable region as defined above, for example a light chain constant region and a heavy chain constant region, may be those from any subtype of immunoglobulin (e.g., IgA, IgD, IgE, IgG (IgG1, IgG2, IgG3, IgG4), IgM, and the like).

By way of further example, the anti-c-Met antibody or the antibody fragment may include: a heavy chain including the amino acid sequence selected from the group consisting of the amino acid sequence of SEQ ID NO: 62 (wherein the amino acid sequence from amino acid residues from the $1^{st}$ to $17^{th}$ positions is a signal peptide), or the amino acid sequence from the $18^{th}$ to $462^{nd}$ positions of SEQ ID NO: 62, the amino acid sequence of SEQ ID NO: 64 (wherein the amino acid sequence from the 1$^{st}$ to 17$^{th}$ positions is a signal peptide), the amino acid sequence from the 18$^{th}$ to 461$^{st}$ positions of SEQ ID NO: 64, the amino acid sequence of SEQ ID NO: 66 (wherein the amino acid sequence from the 1$^{st}$ to 17$^{th}$ positions is a signal peptide), and the amino acid sequence from the 18$^{th}$ to 460$^{th}$ positions of SEQ ID NO: 66; and a light chain including the amino acid sequence selected from the group consisting of the amino acid sequence of SEQ ID NO: 68 (wherein the amino acid sequence from the 1$^{st}$ to 20$^{th}$ positions is a signal peptide), the amino acid sequence from the 21$^{st}$ to 240$^{th}$ positions of SEQ ID NO: 68, the amino acid sequence of SEQ ID NO: 70 (wherein the amino acid sequence from the 1$^{st}$ to 20$^{th}$ positions is a signal peptide), the amino acid sequence from the 21$^{st}$ to 240$^{th}$ positions of SEQ ID NO: 70, and the amino acid sequence of SEQ ID NO: 108.

For example, the anti-c-Met antibody may be selected from the group consisting of:

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 68 or the amino acid sequence from the 21$^{st}$ to 240$^{th}$ positions of SEQ ID NO: 68;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 70 or the amino acid sequence from the 21$^{4}$ to 240$^{th}$ positions of SEQ ID NO: 70;

an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 70 or the amino acid sequence from the 21$^{st}$ to 240$^{th}$ positions of SEQ ID NO: 70;

an antibody including a heavy chain including the amino acid sequence of SEQ ID NO: 62 or the amino acid sequence from the 18$^{th}$ to 462$^{nd}$ positions of SEQ ID NO: 62 and a light chain including the amino acid sequence of SEQ ID NO: 108;

an antibody including a heavy chain including the amino acid sequence of SEQ ID NO: 64 or the amino acid sequence from the 18$^{th}$ to 461$^{st}$ positions of SEQ ID NO: 64 and a light chain including the amino acid sequence of SEQ ID NO: 108; and an antibody including a heavy chain including the amino acid sequence of SEQ ID NO: 66 or the amino acid sequence from the 18$^{th}$ to 460$^{th}$ positions of SEQ ID NO: 66 and a light chain including the amino acid sequence of SEQ ID NO: 108.

According to an embodiment, the anti-c-Met antibody may include a heavy chain including the amino acid sequence from the 18$^{th}$ to 460$^{th}$ positions of SEQ ID NO: 66 and a light chain including the sequence from the 21$^{st}$ to 240$^{th}$ positions of SEQ ID NO: 68, or a heavy chain including the amino acid sequence from the 18$^{th}$ to 460$^{th}$ positions of SEQ ID NO: 66 and a light chain including the sequence of SEQ ID NO: 108.

The polypeptide of SEQ ID NO: 70 is a light chain including human kappa (κ) constant region, and the polypeptide with the amino acid sequence of SEQ ID NO: 68 is a polypeptide obtained by replacing histidine at position 62 (corresponding to position 36 of SEQ ID NO: 68 according to kabat numbering) of the polypeptide with the amino acid sequence of SEQ ID NO: 70 with tyrosine. The production yield of the antibodies may be increased by the replacement. The polypeptide with the amino acid sequence of SEQ ID NO: 108 is a polypeptide obtained by replacing serine at position 32 of SEQ ID NO: 108 (corresponding to position 52 of SEQ ID NO: 68, which corresponds to position 27e according to kabat numbering in the amino acid sequence from amino acid residues 21 to 240 of SEQ ID NO: 68; positioned within CDR-L1) with tryptophan. By such replacement, antibodies and antibody fragments including such sequences exhibits increased activities, such as c-Met biding affinity, c-Met degradation activity, Akt phosphorylation inhibition, and the like.

The anti-c-Met/anti-VEGF bispecific antibody can exhibit a synergistic effect while maintaining affinity and activity to each antigen (c-Met or VEGF). The anti-c-Met/anti-VEGF bispecific antibody can not only inhibit the activity of c-Met and VEGF by the internalization and degradation activity of anti-c-Met antibody but also fundamentally block them by reducing the total amounts of c-Met and VEGF by the degradation thereof. Accordingly, the anti-c-Met/anti-VEGF bispecific antibody can obtain efficient effects even when applied to patients who have developed resistance against pre-existing anti-VEGF antibodies. In addition, the anti-c-Met/anti-VEGF bispecific antibody has an advantage that the binding affinity to c-Met and VEGF can be more stably maintained for longer time in vivo and/or ex vivo.

Another embodiment provides a pharmaceutical composition comprising the anti-VEGF antibody or an antigen-binding fragment thereof as an active ingredient, and optionally a pharmaceutically acceptable carrier. Another embodiment provides a pharmaceutical composition including the anti-c-Met/anti-VEGF bispecific antibody as an active ingredient, and optionally a pharmaceutically acceptable carrier.

Another embodiment provides a method of prevention and/or treatment a cancer, including administering the anti-VEGF antibody or an antigen-binding fragment thereof to a patient in need of the prevention and/or treatment of the cancer. The anti-VEGF antibody or an antigen-binding fragment thereof may be administered in a pharmaceutical effective amount for prevention and/or treatment a cancer. Another embodiment provides a method of prevention and/or treatment a cancer, including administering the anti-c-Met/anti-VEGF bispecific antibody to a patient in need of the prevention and/or treatment of the cancer. The anti-c-Met/anti-VEGF bispecific antibody may be administered in a pharmaceutical effective amount for prevention and/or treatment a cancer. The method of prevention and/or treatment a cancer may further comprises a step of identifying the patient in need of the prevention and/or treatment of the cancer, prior to the step of administering.

The cancer may be any cancer associated with overexpression and/or abnormal activation of c-Met and/or VEGF. The cancer may be any cancer in which VEGF and/or c-Met possibly plays an important role for cancer cell proliferation, invasion, metastasis, and/or resistant to VEGF therapy. The cancer may be a solid cancer or hematological cancer and for instance, may be, but not limited to, one or more selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and the like. In a specific embodiment, the cancer may be stomach (gastric) cancer, but not be limited thereto. In particular, the cancer may be cancer having resistance against pre-existing anticancer drugs, for example, antagonists against VEGF and/or antagonists against c-Met. The an anti-c-Met/anti-VEGF bispecific antibody cab exhibit more effective prevention and/or treatment effects of cancer by simultaneously recognizing and inhibiting c-Met and VEGF, which commonly participate in a carcinogenic mechanism, such as cancer cell proliferation, cancer cell migration, cancer cell invasion, cancer cell metastasis, angiogenesis, apoptosis, and the like. Therefore, the curable cancers may include both primary cancers and metastatic cancers. Thus, the pharmaceutical composition or method may be for preventing and/or treating cancer metastasis and/or cancer invasion.

In the pharmaceutical composition or method, the anti-VEGF antibody or an antigen-binding fragment thereof or the anti-c-Met/anti-VEGF bispecific antibody may be formulated or administered along with at least one additive selected from the group consisting of a pharmaceutically acceptable carriers, diluents, and excipients.

The pharmaceutically acceptable carrier to be included in the composition may be those commonly used for the formulation of antibodies, which may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. The pharmaceutical composition may further include one or more selected from the group consisting of a lubricant, a wetting agent, a sweetener, a flavor enhancer, an emulsifying agent, a suspension agent, and preservative.

The pharmaceutical composition of the anti-VEGF antibody or an antigen-binding fragment thereof or the anti-c-Met/anti-VEGF bispecific antibody may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the compositions may be administered using an optional device that enables an active substance to be delivered to target cells.

A suitable dosage of the pharmaceutical composition, the anti-VEGF antibody or an antigen-binding fragment thereof, or the anti-c-Met/anti-VEGF bispecific antibody may be prescribed in a variety of ways, depending on factors such as formulation methods, administration methods, age of patients, body weight, gender, pathologic conditions, diets, administration time, administration route, excretion speed, and reaction sensitivity. A desirable dosage of the pharmaceutical composition or the anti-c-Met/anti-VEGF bispecific antibody may be in the range of about 0.001 to 100 mg/kg for an adult. For example, the suitable dosage of the pharmaceutical composition, the anti-VEGF antibody or an antigen-binding fragment thereof, or the anti-c-Met/anti-VEGF bispecific antibody may be about 0.001 to about 1000 mg/kg, about 0.01 to about 100 mg/kg, or 0.1 to 50 mg/kg, per a day, but not be limited thereto. The term "pharmaceutically effective amount" used herein refers to an amount of the active ingredient (i.e., the anti-VEGF antibody or an antigen-binding fragment thereof, or the anti-c-Met/anti-VEGF bispecific antibody) exhibiting effects in preventing or treating cancer, and may be properly determined in a variety of ways, depending on factors such as formulation methods, administration methods, age of patients, body weight, gender, pathologic conditions, diets, administration time, administration route, excretion speed, and reaction sensitivity.

The pharmaceutical composition, the anti-VEGF antibody or an antigen-binding fragment thereof, or the anti-c-Met/anti-VEGF bispecific antibody may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

In addition, the pharmaceutical composition, the anti-VEGF antibody or an antigen-binding fragment thereof, or the anti-c-Met/anti-VEGF bispecific antibody may be administered as an individual drug, or together with other drugs, and may be administered sequentially in any order or simultaneously with pre-existing drugs.

Since the pharmaceutical composition includes an antibody or an antigen binding fragment thereof, it may be formulated as an immunoliposome. The liposome containing an antibody may be prepared using a well-known method in the pertinent art. The immunoliposome is a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide exchange reaction. A chemical drug such as doxorubicin may be additionally included in the liposome.

The subject to which the pharmaceutical composition, the anti-VEGF antibody or an antigen-binding fragment thereof, or the anti-c-Met/anti-VEGF bispecific antibody is administered or the patient to which the prevention and/treatment method is applied may be mammals, for example, primates such as humans and monkeys, or rodents such as rats and mice, a cell or a tissue obtained (separated) from mammals, or a culture thereof, but are not be limited thereto. In an embodiment, the subject or the patient may be a cancer patient, for example, a cancer patient having resistance against pre-existing anticancer drugs, for example, antagonists against the target cell membrane proteins (e.g., VEGF), a cell or a tissue obtained (separated) therefrom, or a culture thereof, but are not be limited thereto.

Another embodiment provides a polynucleotide encoding a polypeptide including one amino acid sequence or a combination of two or more amino acid sequences selected from the group consisting of SEQ ID NOs: 109 to 151. In an embodiment, the polynucleotide may encode a polypeptide including an amino acid sequence selected from SEQ ID NOs: 152 to 159, a polypeptide including an amino acid sequence selected from SEQ ID NOs: 160 to 167, or a combination thereof. In another embodiment, the polynucleotide may encode a polypeptide including an amino acid sequence selected from SEQ ID NOs: 168 to 175. For example, the polynucleotide may comprise a nucleotide sequence selected from SEQ ID NOs: 176 to 183. Another embodiment provides a recombinant vector including the polynucleotide. Another embodiment provides a recombinant cell transfected with the recombinant vector.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pcDNA series (Invitrogen), pCI (Promega), Mammalian expression vector (Sigma), pCMV-Tag epitope tagging mammalian vector (Stratagene), pSC101, pGV1106, pACYC177, ColEL pKT230, pME290, pBR322, pUC8/9, pUC6, pBD9, pHC79, pU61, pLAFR1, pHV14, pGEX series, pET series, pUC19, and the like), a phage (for example, λgt4λB, λ-Charon, λΔz1, M13, and the like), or a virus (for example, SV40, and the like), but not be limited thereto.

In the recombinant vector, the polynucleotides may be operatively linked to a promoter. The term "operatively linked" used herein refers to a functional linkage between a nucleotide expression regulating sequence (for example, a promoter sequence) and other nucleotide sequences. Thus, the regulating sequence may regulate the transcription and/or translation of the other nucleotide sequences by being operatively linked.

The recombinant vector may be constructed for cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL$^λ$ promoter, CMV promoter, trp promoter, lac promoter, tac promoter, T7 promoter, and the like), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter, and the like) or a promoter derived from mammalian viruses (for example, an adenovirus late promoter, a vaccinia virus 7.5K promoter, a SV40 promoter, a cytomegalovirus promoter, a tk promoter of HSV, and the like). A transcription termination sequence in an expression vector for a eukaryotic host cell may be, in general, a polyadenylation sequence.

The recombinant cell may be those obtained by transfecting the recombinant vector into a suitable host cell. Any host cells known in the pertinent art to enable stable and continuous cloning or expression of the recombinant vector may be used as the hose cell. Suitable prokaryotic host cells may be one or more selected from *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis*, or *Bacillus thuringiensis*, intestinal bacteria and strains such as *Salmonella typhymurum, Serratia marcescens*, and various *Pseudomonas* species. Suitable eukaryotic host cells to be transformed may be one or more selected from yeasts, such as *Saccharomyces cerevisiae*, insect cells, plant cells, and animal cells, for example, Sp2/0, Chinese hamster ovary (CHO) K1, CHO DG44, GS deficient CHO cell, DHFR deficient CHO cell, PER.C6, W138, BHK, COS-7, HEK-293, HeLa, HepG2, Huh7, 3T3, RIN, and MDCK cell lines, but not be limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

Another embodiment provides a method of preparing the anti-VEGF antibody or the anti-c-Met/anti-VEGF bispecific antibody, the antigen-binding fragment thereof, or the polypeptide, including expressing the polynucleotide encoding the antibody, the antigen-binding fragment, or the polypeptide (for example, in a recombinant vector) in a cell. The step of expressing the polynucleotide may be conducted by culturing the cell comprising the polynucleotide (for example, in a recombinant vector) under a condition allowing the expression of the polynucleotide. The method may further comprise isolating and/or purifying the anti-VEGF antibody or anti-c-Met/anti-VEGF bispecific antibody, the antigen-binding fragment thereof, or the polypeptide from the cell culture, after the step of expressing or culturing.

EXAMPLES

Hereafter, the present invention will be described in detail by examples.

The following examples are intended merely to illustrate the invention and are not construed to restrict the invention.

Reference Example 1: Construction of Anti-c-Met Antibody

1.1. Production of "AbF46", a Mouse Antibody to c-Met

1.1.1. Immunization of Mouse

To obtain immunized mice necessary for the development of a hybridoma cell line, each of five BALB/c mice (Japan SLC, Inc.), 4 to 6 weeks old, was intraperitoneally injected with a mixture of 100 μg of human c-Met/Fc fusion protein (R&D Systems) and one volume of complete Freund's adjuvant. Two weeks after the injection, a second intraperitoneal injection was conducted on the same mice with a mixture of 50 μg of human c-Met/Fc protein and one volume of incomplete Freund's adjuvant. One week after the second immunization, the immune response was finally boosted. Three days later, blood was taken from the tails of the mice and the sera were 1/1000 diluted in PBS and used to examine a titer of antibody to c-Met by ELISA. Mice found to have a sufficient antibody titer were selected for use in the cell fusion process.

1.1.2. Cell Fusion and Production of Hybridoma

Three days before cell fusion, BALB/c mice (Japan SLC, Inc.) were immunized with an intraperitoneal injection of a mixture of 50 μg of human c-Met/Fc fusion protein and one volume of PBS. The immunized mice were anesthetized before excising the spleen from the left half of the body. The spleen was meshed to separate splenocytes which were then suspended in a culture medium (DMEM, GIBCO, Invitrogen). The cell suspension was centrifuged to recover the cell layer. The splenocytes thus obtained ($1 \times 10^8$ cells) were mixed with myeloma cells (Sp2/0) ($1 \times 10^8$ cells), followed by spinning to give a cell pellet. The cell pellet was slowly suspended, treated with 45% polyethylene glycol (PEG) (1 mL) in DMEM for 1 min at 37° C., and supplemented with 1 mL of DMEM. To the cells was added 10 mL of DMEM over 10 min, after which incubation was conducted in a water bath at 37° C. for 5 min. Then the cell volume was adjusted to 50 mL before centrifugation. The cell pellet thus formed was resuspended at a density of $1 \sim 2 \times 10^5$ cells/mL in a selection medium (HAT medium) and 0.1 mL of the cell suspension was allocated to each well of 96-well plates which were then incubated at 37° C. in a $CO_2$ incubator to establish a hybridoma cell population.

1.1.3. Selection of Hybridoma Cells Producing Monoclonal Antibodies to c-Met Protein From the hybridoma cell population established in Reference Example 1.1.2, hybridoma cells which showed a specific response to c-Met protein were screened by ELISA using human c-Met/Fc fusion protein and human Fc protein as antigens.

Human c-Met/Fc fusion protein was seeded in an amount of 50 μL (2 μg/mL)/well to microtiter plates and allowed to adhere to the surface of each well. The antibody that remained unbound was removed by washing. For use in selecting the antibodies that do not bind c-Met but recognize Fc, human Fc protein was attached to the plate surface in the same manner.

The hybridoma cell culture obtained in Reference Example 1.1.2 was added in an amount of 50 μL to each well of the plates and incubated for 1 hour. The cells remaining unreacted were washed out with a sufficient amount of Tris-buffered saline and Tween 20 (TBST). Goat anti-mouse IgG-horseradish peroxidase (HRP) was added to the plates and incubated for 1 hour at room temperature. The plates were washed with a sufficient amount of TBST, followed by reacting the peroxidase with a substrate (OPD). Absorbance at 450 nm was measured on an ELISA reader.

Hybridoma cell lines which secrete antibodies that specifically and strongly bind to human c-Met but not human Fc were selected repeatedly. From the hybridoma cell lines obtained by repeated selection, a single clone producing a monoclonal antibody was finally separated by limiting dilution. The single clone of the hybridoma cell line producing the monoclonal antibody was deposited with the Korean Cell Line Research Foundation, an international depository authority located at Yungun-Dong, Jongno-Gu, Seoul, Korea, on Oct. 6, 2009, with Accession No. KCLRF-BP-00220 according to the Budapest Treaty (refer to Korean Patent Laid-Open Publication No. 2011-0047698).

1.1.4. Production and Purification of Monoclonal Antibody

The hybridoma cell line obtained in Reference Example 1.1.3 was cultured in a serum-free medium, and the monoclonal antibody (AbF46) was produced and purified from the cell culture.

First, the hybridoma cells cultured in 50 mL of a medium (DMEM) supplemented with 10% (v/v) FBS were centrifuged and the cell pellet was washed twice or more with 20 mL of PBS to remove the FBS there from. Then, the cells were resuspended in 50 mL of DMEM and incubated for 3 days at 37° C. in a $CO_2$ incubator.

After the cells were removed by centrifugation, the supernatant was stored at 4° C. before use or immediately used for the separation and purification of the antibody. An AKTA system (GE Healthcare) equipped with an affinity column (Protein G agarose column; Pharmacia, USA) was used to purify the antibody from 50 to 300 mL of the supernatant, followed by concentration with an filter (Amicon). The antibody in PBS was stored before use in the following examples.

1.2. Construction of chAbF46, a Chimeric Antibody to c-Met

A mouse antibody is apt to elicit immunogenicity in humans. To solve this problem, chAbF46, a chimeric antibody, was constructed from the mouse antibody AbF46 produced in Experimental Example 1.1.4 by replacing the constant region, but not the variable region responsible for antibody specificity, with an amino sequence of the human IgG1 antibody.

In this regard, a gene was designed to include the nucleotide sequence of "EcoRI-signal sequence-VH-NheI-CH-TGA-XhoI" (SEQ ID NO: 38) for a heavy chain and the nucleotide sequence of "EcoRI-signal sequence-VL-BsiWI-CL-TGA-XhoI" (SEQ ID NO: 39) for a light chain and synthesized. Then, a DNA fragment having the heavy chain nucleotide sequence (SEQ ID NO: 38) and a DNA fragment having the light chain nucleotide sequence (SEQ ID NO: 39) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen), and a pcDNA™ 3.3-TOPO TA Cloning Kit (Cat no. 8300-01), respectively.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

Afterwards, the cells were incubated in DMEM supplemented with 10% (v/v) FBS for 5 hours at 37° C. under a 5% $CO_2$ condition and then in FBS-free DMEM for 48 hours at 37° C. under a 5% $CO_2$ condition.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a chimeric antibody AbF46 (hereinafter referred to as "chAbF46").

1.3. Construction of Humanized Antibody huAbF46 from Chimeric Antibody chAbF46

1.3.1. Heavy Chain Humanization

To design two domains H1-heavy and H3-heavy, human germline genes which share the highest identity/homology with the VH gene of the mouse antibody AbF46 purified in Reference Example 1.2 were analyzed. An Ig BLAST (www.ncbi.nlm.nih.gov/igblast/) result revealed that VH3-71 has an identity/identity/homology of 83% at the amino acid level. CDR-H1, CDR-H2, and CDR-H3 of the mouse antibody AbF46 were defined according to Kabat numbering. A design was made to introduce the CDR of the mouse antibody AbF46 into the framework of VH3-71. Back mutations to the amino acid sequence of the mouse AbF46 were conducted at positions 30 (S→T), 48 (V→L), 73 (D→N), and 78 (T→L). Then, H1 was further mutated at positions 83 (R→K) and 84 (A→T) to finally establish H1-heavy (SEQ ID NO: 40) and H3-heavy (SEQ ID NO: 41).

For use in designing H4-heavy, human antibody frameworks were analyzed by a BLAST search. The result revealed that the VH3 subtype, known to be most stable, is very similar in framework and sequence to the mouse antibody AbF46. CDR-H1, CDR-H2, and CDR-H3 of the mouse antibody AbF46 were defined according to Kabat numbering and introduced into the VH3 subtype to construct H4-heavy (SEQ ID NO: 42).

1.3.2. Light Chain Humanization

To design two domains H1-light (SEQ ID NO: 43) and H2-light (SEQ ID NO: 44), human germline genes which share the highest identity/homology with the VH gene of the mouse antibody AbF46 were analyzed. An Ig BLAST search result revealed that VK4-1 has a identity/homology of 75% at the amino acid level. CDR-L1, CDR-L2, and CDR-L3 of the mouse antibody AbF46 were defined according to Kabat numbering. A design was made to introduce the CDR of the mouse antibody AbF46 into the framework of VK4-1. Back mutations to the amino acid sequence of the mouse AbF46 were conducted at positions 36 (Y→H), 46 (L→M), and 49 (Y→I). Only one back mutation was conducted at position 49 (Y→I) on H2-light.

To design H3-light (SEQ ID NO: 45), human germline genes which share the highest identity/homology with the VL gene of the mouse antibody AbF46 were analyzed by a search for BLAST. As a result, VK2-40 was selected. VL and VK2-40 of the mouse antibody AbF46 were found to have a identity/homology of 61% at an amino acid level. CDR-L1, CDR-L2, and CDR-L3 of the mouse antibody were defined according to Kabat numbering and introduced into the framework of VK4-1. Back mutations were conducted at positions 36 (Y→H), 46 (L→M), and 49 (Y→I) on H3-light.

For use in designing H4-light (SEQ ID NO: 46), human antibody frameworks were analyzed. A Blast search revealed that the Vk1 subtype, known to be the most stable, is very similar in framework and sequence to the mouse antibody AbF46. CDR-L1, CDR-L2, and CDR-L3 of the mouse antibody AbF46 were defined according to Kabat numbering and introduced into the Vkl subtype. Back mutations were conducted at positions 36 (Y→H), 46 (L→M), and 49 (Y→I) on H4-light.

Thereafter, DNA fragments having the heavy chain nucleotide sequences (H1-heavy: SEQ ID NO: 47, H3-heavy: SEQ ID NO: 48, H4-heavy: SEQ ID NO: 49) and DNA fragments having the light chain nucleotide sequences (H1-light: SEQ ID NO: 50, H2-light: SEQ ID NO: 51, H3-light: SEQ ID NO: 52, H4-light: SEQ ID NO: 53) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing a humanized antibody.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5×10^5$ cells/ml, and after 24 hours, when the cell number reached to $1×10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify a humanized antibody AbF46 (hereinafter referred to as "huAbF46"). The humanized antibody huAbF46 used in the following examples included a combination of H4-heavy (SEQ ID NO: 42) and H4-light (SEQ ID NO: 46).

1.4. Construction of scFV Library of huAbF46 Antibody

For use in constructing an scFv of the huAbF46 antibody from the heavy and light chain variable regions of the huAbF46 antibody, a gene was designed to have the structure of "VH-linker-VL" for each of the heavy and the light chain variable region, with the linker including the amino acid sequence "GLGGLGGGGSGGGGSGGSSGVGS" (SEQ ID NO: 54). A polynucleotide sequence (SEQ ID NO: 55) encoding the designed scFv of huAbF46 was synthesized in Bioneer and an expression vector for the polynucleotide had the nucleotide sequence of SEQ ID NO: 56.

After expression, the product was found to exhibit specificity to c-Met.

1.5. Construction of Library Genes for Affinity Maturation 1.5.1. Selection of target CDRs and Synthesis of Primers The affinity maturation of huAbF46 was achieved. First, six complementary determining regions (CDRs) were defined according to Kabat numbering. The CDRs are given in Table 4, below.

TABLE 4

| CDR | Amino Acid Sequence |
|---|---|
| CDR-H1 | DYYMS (SEQ ID NO: 1) |
| CDR-H2 | FIRNKANGYTTEYSASVKG (SEQ ID NO: 2) |
| CDR-H3 | DNWFAY (SEQ ID NO: 3) |
| CDR-L1 | KSSQSLLASGNQNNYLA (SEQ ID NO: 10) |
| CDR-L2 | WASTRVS (SEQ ID NO: 11) |
| CDR-L3 | QQSYSAPLT (SEQ ID NO: 12) |

For use in the introduction of random sequences into the CDRs of the antibody, primers were designed as follows. Conventionally, N codons were utilized to introduce bases at the same ratio (25% A, 25% G, 25% C, 25% T) into desired sites of mutation. In this experiment, the introduction of random bases into the CDRs of huAbF46 was conducted in such a manner that, of the three nucleotides per codon in the wild-type polynucleotide encoding each CDR, the first and second nucleotides conserved over 85% of the entire sequence while the other three nucleotides were introduced at the same percentage (each 5%) and that the same possibility was imparted to the third nucleotide (33% G, 33% C, 33% T).

1.5.2. Construction of a Library of huAbF46 Antibodies and Affinity for c-Met

The construction of antibody gene libraries through the introduction of random sequences was carried out using the primers synthesized in the same manner as in Reference Example 1.5.1. Two PCR products were obtained using a polynucleotide covering the scFV of huAbF46 as a template, and were subjected to overlap extension PCR to give scFv library genes for huAbF46 antibodies in which only desired CDRs were mutated. Libraries targeting each of the six CDRs prepared from the scFV library genes were constructed.

The affinity for c-Met of each library was compared to that of the wildtype. Most libraries were lower in affinity for c-Met, compared to the wild-type. The affinity for c-Met was retained in some mutants.

1.6. Selection of Antibody with Improved Affinity from Libraries

After maturation of the affinity of the constructed libraries for c-Met, the nucleotide sequence of scFv from each clone was analyzed. The nucleotide sequences thus obtained are summarized in Table 5 and were converted into IgG forms. Four antibodies which were respectively produced from clones L3-1, L3-2, L3-3, and L3-5 were used in the subsequent experiments.

TABLE 5

| Clone | Library constructed | CDR Sequence |
|---|---|---|
| H11-4 | CDR-H1 | PEYYMS (SEQ ID NO: 22) |
| YC151 | CDR-H1 | PDYYMS (SEQ ID NO: 23) |
| YC193 | CDR-H1 | SDYYMS (SEQ ID NO: 24) |
| YC244 | CDR-H2 | RNNANGNT (SEQ ID NO: 25) |
| YC321 | CDR-H2 | RNKVNGYT (SEQ ID NO: 26) |
| YC354 | CDR-H3 | DNWLSY (SEQ ID NO: 27) |
| YC374 | CDR-H3 | DNWLTY (SEQ ID NO: 28) |
| L1-1 | CDR-L1 | KSSHSLLASGNQNNYLA (SEQ ID NO: 29) |
| L1-3 | CDR-L1 | KSSRSLLSSGNHKNYLA (SEQ ID NO: 30) |
| L1-4 | CDR-L1 | KSSKSLLASGNQNNYLA (SEQ ID NO: 31) |
| L1-12 | CDR-L1 | KSSRSLLASGNQNNYLA (SEQ ID NO: 32) |
| L1-22 | CDR-L1 | KSSHSLLASGNQNNYLA (SEQ ID NO: 33) |
| L2-9 | CDR-L2 | WASKRVS (SEQ ID NO: 34) |
| L2-12 | CDR-L2 | WGSTRVS (SEQ ID NO: 35) |
| L2-16 | CDR-L2 | WGSTRVP (SEQ ID NO: 36) |
| L3-1 | CDR-L3 | QQSYSRPYT (SEQ ID NO: 13) |
| L3-2 | CDR-L3 | GQSYSRPLT (SEQ ID NO: 14) |
| L3-3 | CDR-L3 | AQSYSHPFS (SEQ ID NO: 15) |
| L3-5 | CDR-L3 | QQSYSRPFT (SEQ ID NO: 16) |
| L3-32 | CDR-L3 | QQSYSKPFT (SEQ ID NO: 37) |

1.7. Conversion of Selected Antibodies into IgG

Respective polynucleotides encoding heavy chains of the four selected antibodies were designed to have the structure of "EcoRI-signal sequence-VH-NheI-CH-XhoI" (SEQ ID NO: 38). The heavy chains of huAbF46 antibodies were used as they were because their amino acids were not changed during affinity maturation. In the case of the hinge region, however, the U6-HC7 hinge (SEQ ID NO: 57) was employed instead of the hinge of human IgG1. Genes were also designed to have the structure of "EcoRI-signal sequence-VL-BsiWI-CL-XhoI" for the light chain. Polypeptides encoding light chain variable regions of the four antibodies which were selected after the affinity maturation were synthesized in Bioneer. Then, a DNA fragment having the heavy chain nucleotide sequence (SEQ ID NO: 38) and DNA fragments having the light chain nucleotide sequences (DNA fragment including L3-1-derived CDR-L3: SEQ ID NO: 58, DNA fragment including L3-2-derived CDR-L3: SEQ ID NO: 59, DNA fragment including L3-3-derived CDR-L3: SEQ ID NO: 60, and DNA fragment including L3-5-derived CDR-L3: SEQ ID NO: 61) were digested with EcoRI (NEB, R0101S) and XhoI (NEB, R0146S) before cloning into a pOptiVEC™-TOPO TA Cloning Kit enclosed in an OptiCHO™ Antibody Express Kit (Cat no. 12762-019, Invitrogen) and a pcDNA™ 3.3-TOPO TA Cloning Kit (Cat no. 8300-01), respectively, so as to construct recombinant vectors for expressing affinity-matured antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with an IgG elution buffer (Thermo Scientific, 21004). The buffer was exchanged with PBS to purify four affinity-matured antibodies (hereinafter referred to as "huAbF46-H4-A1 (L3-1 origin), huAbF46-H4-A2 (L3-2 origin), huAbF46-H4-A3 (L3-3 origin), and huAbF46-H4-A5 (L3-5 origin)," respectively).

1.8. Construction of Constant Region- and/or Hinge Region-Substituted huAbF46-H4-A1

Among the four antibodies selected in Reference Example 1.7, huAbF46-H4-A1 was found to be the highest in affinity for c-Met and the lowest in Akt phosphorylation and c-Met degradation degree. In the antibody, the hinge region, or the constant region and the hinge region, were substituted.

The antibody huAbF46-H4-A1 (U6-HC7) was composed of a heavy chain including the heavy chain variable region of huAbF46-H4-A1, U6-HC7 hinge, and the constant region of human IgG1 constant region, and a light chain including the light chain variable region of huAbF46-H4-A1 and human kappa constant region. The antibody huAbF46-H4-A1 (IgG2 hinge) was composed of a heavy chain including a heavy chain variable region, a human IgG2 hinge region, and a human IgG1 constant region, and a light chain including the light chain variable region of huAbF46-H4-A1 and a human kappa constant region. The antibody huAbF46-H4-A1 (IgG2 Fc) was composed of the heavy chain variable region of huAbF46-H4-A1, a human IgG2 hinge region, and a human IgG2 constant region, and a light chain including the light variable region of huAbF46-H4-A1 and a human kappa constant region. The histidine residue at position 36 on the human kappa constant region of the light chain was changed to tyrosine in all of the three antibodies to increase antibody production.

For use in constructing the three antibodies, a polynucleotide (SEQ ID NO: 63) encoding a polypeptide (SEQ ID NO: 62) composed of the heavy chain variable region of huAbF46-H4-A1, a U6-HC7 hinge region, and a human IgG1 constant region, a polynucleotide (SEQ ID NO: 65) encoding a polypeptide (SEQ ID NO: 64) composed of the heavy chain variable region of huAbF46-H4-A1, a human IgG2 hinge region, and a human IgG1 region, a polynucleotide (SEQ ID NO: 67) encoding a polypeptide (SEQ ID NO: 66) composed of the heavy chain variable region of huAbF46-H4-A1, a human IgG2 region, and a human IgG2 constant region, and a polynucleotide (SEQ ID NO: 69) encoding a polypeptide (SEQ ID NO: 68) composed of the light chain variable region of huAbF46-H4-A1, with a tyrosine residue instead of histidine at position 36, and a human kappa constant region were synthesized in Bioneer. Then, the DNA fragments having heavy chain nucleotide sequences were inserted into a pOptiVEC™-TOPO TA Cloning Kit enclosed in an OptiCHO™ Antibody Express Kit (Cat no. 12762-019, Invitrogen) while DNA fragments having light chain nucleotide sequences were inserted into a pcDNA™ 3.3-TOPO TA Cloning Kit (Cat no. 8300-01) so as to construct vectors for expressing the antibodies.

Each of the constructed vectors was amplified using Qiagen Maxiprep kit (Cat no. 12662), and a transient expression was performed using Freestyle™ MAX 293 Expression System (Invitrogen). 293 F cells were used for the expression and cultured in FreeStyle™ 293 Expression Medium in a suspension culture manner. At one day before the transient expression, the cells were provided in the concentration of $5 \times 10^5$ cells/ml, and after 24 hours, when the cell number reached to $1 \times 10^6$ cells/ml, the transient expression was performed. A transfection was performed by a liposomal reagent method using Freestyle™ MAX reagent (Invitrogen), wherein in a 15 ml tube, the DNA was provided in the mixture ratio of 1:1 (heavy chain DNA:light chain DNA) and mixed with 2 ml of OptiPro™ SFM (Invitrogen) (A), and in another 15 ml tube, 100 μl (microliter) of Freestyle™ MAX reagent and 2 ml of OptiPro™ SFM were mixed (B), followed by mixing (A) and (B) and incubating for 15 minutes. The obtained mixture was slowly mixed with the cells provided one day before the transient expression. After completing the transfection, the cells were incubated in 130 rpm incubator for 5 days under the conditions of 37° C., 80% humidity, and 8% $CO_2$.

After centrifugation, the supernatant was applied to AKTA prime (GE Healthcare) to purify the antibody. In this regard, 100 mL of the supernatant was loaded at a flow rate of 5 mL/min to AKTA Prime equipped with a Protein A column (GE healthcare, 17-0405-03), followed by elution with IgG elution buffer (Thermo Scientific, 21004). The buffer was exchanged with PBS to finally purify three antibodies (huAbF46-H4-A1 (U6-HC7), huAbF46-H4-A1 (IgG2 hinge), and huAbF46-H4-A1 (IgG2 Fc)). Among the three antibodies, huAbF46-H4-A1 (IgG2 Fc) was selected for the following examples, and name as L3-1Y-IgG2.

Example 1: Preparation of an Anti-VEGF scFv

An anti-VEGF scFv (see Table 9) binding to VEGF was prepared by inserting a peptide linker of (GGGGS)$_3$ between a heavy chain variable region (see Table 8) and a light chain variable region (see Table 8). In particular, the DNA sequence encoding the anti-VEGF scFv (see Table 9) was synthesized using an automatic gene synthesis (Bioneer Inc.).

The amino acid sequences of the heavy chain variable region and the light chain variable region of the prepared anti-VEGF scFv, and coding nucleotide sequences thereof are summarized in Tables 6-9 (wherein the sequences underlined indicate CDRs, i.e., CDR-H1, CDR-H2, and CDR-H3, or CDR-L1, CDR-L2, and CDR-L3, in sequence):

TABLE 6

| scFv | CDR-H1 | CDR-H2 | CDR-H3 |
|---|---|---|---|
| E1 | GYAMS (SEQ ID NO: 109) | SIYSSSGSKYYADSVKG (SEQ ID NO: 114) | ASSTCTRTWCSYDDAMDV (SEQ ID NO: 122) |
| E2 | DYAMS (SEQ ID NO: 110) | SIYPGSGSKYYADSVKG (SEQ ID NO: 115) | DAWFRGHNVFDY (SEQ ID NO: 123) |
| E3 | NYDMS (SEQ ID NO: 111) | GIYPNGGSKYYADSVKG (SEQ ID NO: 116) | ALRQCQRYWCSYADGMDV (SEQ ID NO: 124) |
| E5 | DYYMS (SEQ ID NO: 112) | AIYSGGGSIYYADSVKG (SEQ ID NO: 117) | DVQWNKAPRFDY (SEQ ID NO: 125) |
| E7 | SYSMS (SEQ ID NO: 113) | GISHGGGNKYYADSVKG (SEQ ID NO: 118) | DLRANNDTGFDY (SEQ ID NO: 126) |
| E10 | NYDMS (SEQ ID NO: 111) | LISHGGGNIYYADSVKG (SEQ ID NO: 119) | VPVMCTNHWCSYANGMDV (SEQ ID NO: 127) |

TABLE 6-continued

| scFv | CDR-H1 | CDR-H2 | CDR-H3 |
|---|---|---|---|
| E11 | GYAMS (SEQ ID NO: 109) | GISHDGGNTYYADSVKG (SEQ ID NO: 120) | DRRKGPSTEFDY (SEQ ID NO: 128) |
| E12 | DYAMS (SEQ ID NO: 110) | WIYPGDSSIYYADSVKG (SEQ ID NO: 121) | LLSIDQAQLHYYYDAMDV (SEQ ID NO: 129) |

TABLE 7

| scFv | CDR-L1 | CDR-L2 | CDR-L3 |
|---|---|---|---|
| E1 | TGSSSNIGNNAVT (SEQ ID NO: 130) | DDSHRPS (SEQ ID NO: 138) | GTWDYSLSGYV (SEQ ID NO: 146) |
| E2 | TGSSSNIGSNNVT (SEQ ID NO: 131) | SDSHRPS (SEQ ID: NO: 139) | GSWDYSLSAYV (SEQ ID NO: 147) |
| E3 | TGSSSNIGSNYVS (SEQ ID NO: 132) | ADSQRPS (SEQ ID NO: 140) | GTWDYSLSGYV (SEQ ID NO: 146) |
| E5 | SGSSSNIGSNDVS (SEQ ID NO: 133) | ADSNRPS (SEQ ID NO: 141) | GSWDYSLSGYV (SEQ ID NO: 148) |
| E7 | TGSSSNIGSNAVT (SEQ ID NO: 134) | DDNHRPS (SEQ ID: NO: 142) | GAWDYSLNAYV (SEQ ID NO: 149) |
| E10 | SASSSNIGSNAVY (SEQ ID NO: 135) | SDNQRPS (SEQ ID: NO: 143) | GSWDYSLSAYV (SEQ ID NO: 147) |
| E11 | TGSSSNIGSNSVS (SEQ ID NO: 136) | DDNNRPS (SEQ ID: NO: 144) | GAWDYSLSAYV (SEQ ID NO: 150) |
| E12 | TGSSSNIGNYYVY (SEQ ID NO: 137) | ANSHRPS (SEQ ID: NO: 145) | GSWDDSLSAYV (SEQ ID NO: 151) |

TABLE 8

| scFv | Heavy chain variable region | Light chain variable region |
|---|---|---|
| E1 | EVQLLESGGGLVQPGGSLRLSCAASGFTFS<u>GYAMS</u>WVRQAPGKGLEWVS<u>SIYSSSGSKYYADSVKG</u>RFTISRDNSKNTLYLQMNSLRAEDTAVYYCAR<u>ASSTCTRTWCSYDDAMDV</u>WGQGTLVTVSS (SEQ ID NO: 152) | QSVLTQPPSASGTPGQRVTISC<u>TGSSSNIGNNAVT</u>WYQQLPGTAPKLLIY<u>DDSHRPS</u>GVPDRFSGSKSGTSASLAISGLRSEDEADYYC<u>GTWDYSLSGYV</u>FGGGTKLTVLG (SEQ ID NO: 160) |
| E2 | EVQLLESGGGLVQTGGSLRLSCAASGFTFS<u>DYAMS</u>WVRQAPGKGLEWVS<u>SIYPGSGSKYYADSVKG</u>RFAISRDNSKNTLYLQMNSLRAEDTAVYYCAR<u>DAWFRGHNVFDY</u>WGQGTLVTVSS (SEQ ID NO: 153) | QSVLTQPPSASGTPGQRVTISC<u>TGSSSNIGSNNVT</u>WYQQLPGTAPKLLIY<u>SDSHRPS</u>GVPDRFSGSKSGTSASLAISGLQSEDEADYYC<u>GSWDYSLSAYV</u>FGGGTKLTVLG (SEQ ID NO: 161) |
| E3 | EVQLLESGGGLVQPGGSLRLSCAASGFTFS<u>NYDMS</u>WVRQAPGKGLEWVS<u>GIYPNGGSKYYADSVKG</u>RFTISRDNSKNTLYLQMNSLRAEDTAVYYCAR<u>ALRQCQRYWCSYADGMDV</u>WGQGTLVTVSS (SEQ ID NO: 154) | QSVLTQPPSASGTPGQRVTISC<u>TGSSSNIGSNYVS</u>WYQQLPGTAPKLLIY<u>ADSQRPS</u>GVPDRFSGSKSGTSASLAISGLRSEDEADYYC<u>GTWDYSLSGYV</u>LGGGTKLTVLG (SEQ ID NO: 162) |
| E5 | EVQLLESGGGLVQPGGSLRLSCAASGFTFS<u>DYYMS</u>WVRQAPGKGLEWVS<u>AIYSGGGSIYYADSVKG</u>RFTISRDNSKNTLYLQMNSLRAED | QSVLTQPPSASGAPGQRVTISC<u>SGSSSNIGSNDVS</u>WYQQLPGTAPKLLIY<u>ADSNRPS</u>GVPSGSKSGTSASLAISGLRSEDEADYYC<u>GSWDYSL</u> |

TABLE 8-continued

| scFv | Heavy chain variable region | Light chain variable region |
|---|---|---|
| | RFDTAVYYCAR<u>DVQWNKAPRFDY</u>WGQGTLV TVSS (SEQ ID NO: 155) | <u>SGYV</u>FGGGTKLTVLG (SEQ ID NO: 163) |
| E7 | EVQLLESGGGLVQPGGSLRLSCAASGFTFS <u>SYSMS</u>WVRQAPGKGLEWVS<u>GISHGGGNKYY ADSVK</u>GRFTISRDNSKNTLYLQMNSLRAED TAVYYCAR<u>DLRANNDTGFDY</u>WGQGTLVTVS S (SEQ ID NO: 156) | QSVLTQPPSSSGTPGQRVTISC<u>TGSSSNIGS NAVT</u>WYQQLPGTAPKLLIY<u>DDNHRPS</u>GVPDR FSGSKSGTSASLAISGLRSEDEADYYC<u>GAWD YSLNAYV</u>FGGGTKLTVLG (SEQ ID NO: 164) |
| E10 | EVQLLESGGGLVQPGGSLRLSCAASGFTFS <u>NYDMS</u>WVRQAPGKGLEWVS<u>LISHGGGNIYY ADSVK</u>GRFTISRDNSKNTLYLQMNSLRAER TAVYYCAR<u>VPVMCTNHWCSYANGMDV</u>WG QGTLVTVSS (SEQ ID NO: 157) | QSVLTQPPSASGTPGQRVIISC<u>SASSSNIGS NAVY</u>WYQQLPGTAPKLLIY<u>SDNQRPS</u>GVPDS GSKSGTSASLAISGLRSEDEADYYC<u>GSWDYS LSAYV</u>FGGGTKLTVLG (SEQ ID NO: 165) |
| E11 | EVQLLESGGGLVQPGGSLRLSCAASGFTFS <u>GYAMS</u>WVRQAPGKGLEWVS<u>GISHDGGNTYY ADSVK</u>GRFTISRDNSKNTLYLQMNSLRAED TAVYYCAR<u>DRRKGPSTEFDY</u>WGQGTLVTVS S (SEQ ID NO: 158) | QSVLTQPPSLSGTPGQRVTISC<u>TGSSSNIGS NSVS</u>WYQQLPGTAPKLLIY<u>DDNNRPS</u>GVPDR FSGSKSGTSASLAISGLRSEDEADYYC<u>GAWD YSLSAYV</u>FGGGTKLTVLG (SEQ ID NO: 166) |
| E12 | EVQLLESGGGLVQTGGSLRLSCAASGFTFS <u>DYAMS</u>WVRQAPGKGLEWVS<u>WIYPGDSSIYY ADSVK</u>GRFTISRDNSKNTLYLQMNSLRAED RFDTAVYYCAR<u>LLSIDQAQLHYYYDAMDV</u>W GQGTLVTVSS (SEQ ID NO: 159) | QSVLTQPPSPSGTPGQRVTISC<u>TGSSSNIGN YVVY</u>WYQQLPGTAPKLLIY<u>ANSHRPS</u>GVPSG SKSGTSASLAISGLRSEDEADYYC<u>GSWDDSL SAYV</u>FGGGTKLTVLG (SEQ ID NO: 167) |

TABLE 9

| scFv | Amino acid sequence of scFv | Coding nucleotide sequence of scFv |
|---|---|---|
| E1 | EVQLLESGGGLVQPGGSLRLSCAASGF TFS<u>GYAMS</u>WVRQAPGKGLEWVS<u>SIYSS SGSKYY</u>ADSVKGRFTISRDNSKNTLYL QMNSLRAEDTAVYYCAR<u>ASSTCTRTWC SYDDAMDV</u>WGQGTLVTVSSGGGGSGGG GSGGGGSQSVLTQPPSASGTPGQRVTI SC<u>TGSSSNIGNNAVT</u>WYQQLPGTAPKL LIY<u>DDSHRPS</u>GVPDRFSGSKSGTSASL AISGLRSEDEADYYC<u>GTWDYSLSGYVF</u> GGGTKLTVLG (SEQ ID NO: 168) | GAGGTGCAGCTGTTGGAGTCTGGGGGAGGCTTGG TACAGCCTGGGGGGTCCCTGAGACTCTCCTGTGC AGCCTCTGGATTCACCTTTAGCGGTTATGCTATG AGCTGGGTCCGCCAGGCTCCAGGGAAGGGGCTGG AGTGGGTCTCATCGATCTATTCTAGTAGTGGTAG TAAATATTACGCTGATTCTGTAAAAGGTCGGTTC ACCATCTCCAGAGACAATTCCAAGAACACGCTGT ATCTGCAAATGAACAGCTGAGAGCCGAGGACAC GGCCGTGTATTACTGTGCGAGAGCTAGTAGTACG TGTACGCGGACGTGGTGTTCTTATGATGATGCTA TGGACGTCTGGGGCCAGGGTACACTGGTCACCGT GAGCTCAGGTGGAGGCGGTTCAGGCGGAGGTGGA TCCGGCGGTGGCGGATCGCAGTCTGTGCTGACTC AGCCACCCTCAGCGTCTGGGACCCCCGGGCAGAG GGTCACCATCTCTTGTACTGGCTCTTCATCTAAT ATTGGCAATAATGCTGTCACCTGGTACCAGCAGC TCCCAGGAACGGCCCCCAAACTCCTCATCTATGA TGATAGTCATCGGCCAAGCGGGGTCCCTGACCGA TTCTCTGGCTCCAAGTCTGGCACCTCAGCCTCCC TGGCCATCAGTGGGCTCCGGTCCGAGGATGAGGC TGATTATTACTGTGGTACTTGGGATTATAGCCTG AGTGGTTATGTCTTCGGCGGAGGCACCAAGCTGA CGGTCCTAGGC (SEQ ID NO: 176) |
| E2 | EVQLLESGGGLVQTGGSLRLSCAASGF TFS<u>DYAMS</u>WVRQAPGKGLEWVS<u>SIYPG SGSKYY</u>ADSVKGRFAISRDNSKNTLYL QMNSLRAEDTAVYYCAR<u>DAWFRGHNVF DY</u>WGQGTLVTVSSGGGGSGGGGSGGGG SQSVLTQPPSASGTPGQRVTISC<u>TGSS SNIGSNNVT</u>WYQQLPGTAPKLLIY<u>SDS HRPS</u>GVPDRFSGSKSGTSASLAISGLQ SEDEADYYC<u>GSWDYSLSAYV</u>FGGGTKL TVLG (SEQ ID NO: 169) | GAGGTGCAGCTGTTGGAGTCTGGGGGAGGCTTGG TACAGACTGGGGGGTCCCTGAGACTCTCCTGTGC AGCCTCTGGATTCACCTTTAGCGATTATGCTATG AGCTGGGTCCGCCAGGCTCCAGGGAAGGGGCTGG AGTGGGTCTCATCGATCTATCCTGGTAGTGGTAG TAAATATTACGCTGATTCTGTAAAAGGTCGGTTC GCCATCTCCAGAGACAATTCCAAGAACACGCTGT ATCTGCAAATGAACAGCTGAGAGCCGAGGACAC GGCCGTGTATTACTGTGCGAGAGATGCTTGGTTT CGGGGTCATAATGTTTTCGACTACTGGGGCCAGG GTACACTGGTCACCGTGAGCTCAGGTGGAGGCGG TTCAGGCGGAGGTGGATCCGGCGGTGGCGGATCG CAGTCTGTGCTGACTCAGCCACCCTCAGCGTCTG |

TABLE 9-continued

| scFv | Amino acid sequence of scFv | Coding nucleotide sequence of scFv |
|---|---|---|
| | | GGACCCCCGGGCAGAGGGTCACCATCTCTTGTAC TGGCTCTTCATCTAATATTGGCAGTAATAATGTC ACCTGGTACCAGCAGCTCCCAGGAACGGCCCCCA AACTCCTCATCTATTCTGATAGTCATCGGCCAAG CGGGGTCCCTGACCGATTCTCTGGCTCCAAGTCT GGCACCTCAGCCTCCCTGGCCATCAGTGGGCTCC AGTCCGAGGATGAGGCTGATTATTACTGTGGTTC TTGGGATTATAGCCTGAGTGCTTATGTCTTCGGC GGAGGCACCAAGCTGACGGTCCTAGGC (SEQ ID NO: 177) |
| E3 | EVQLLESGGGLVQPGGSLRLSCAASGF TFS<u>NYDMS</u>WVRQAPGKGLEWVS<u>GIYPN GGSKYYADSVKG</u>RFTISRDNSKNTLYL QMNSLRAEDTAVYYCAR<u>ALRQCQRYWC SYADGMDV</u>WGQGTLVTVSSGGGGSGGG GSGGGGSQSVLTQPPSASGTPGQRVTI SC<u>TGSSSNIGSNYVS</u>WYQQLPGTAPKL LIY<u>ADSQRPS</u>GVPDRFSGSKSGTSASL AISGLRSEDEADYYC<u>GTWDYSLSGYVL</u> GGGTKLTVLG (SEQ ID NO: 170) | GAGGTGCAGCTGTTGGAGTCTGGGGGAGGCTTGG TACAGCCTGGGGGGTCCCTGAGACTCTCCTGTGC AGCCTCCGGATTCACCTTTAGCAATTATGATATG AGCTGGGTCCGCCAGGCTCCAGGGAAGGGGCTGG AGTGGGTCTCAGGGATCTATCCTAATGGTGGTAG TAAATATTACGCTGATTCTGTAAAAGGTCGGTTC ACCATCTCCAGAGACAATTCCAAGAACACGCTGT ATCTGCAAATGAACAGCCTGAGAGCCGAGGACAC GGCCGTGTATTACTGTGCGAGAGCTCTTCGTCAG TGTCAGCGTTATTGGTGTTCTTATGCTGATGGTA TGGACGTCTGGGGCCAGGGTACACTGGTCACCGT GAGCTCAGGTGGAGGCGGTTCAGGCGGAGGTGGA TCCGGCGGTGGCGGATCGCAGTCTGTGCTGACTC AGCCACCCTCAGCGTCTGGGACCCCCGGGCAGAG GGTCACCATCTCTTGTACTGGCTCTTCATCTAAT ATTGGCAGTAATTATGTCTCCTGGTACCAGCAGC TCCCAGGAACGGCCCCCAAACTCCTCATCTATGC TGATAGTCAGCGGCCAAGCGGGGTCCCTGACCGA TTCTCTGGCTCCAAGTCTGGCACCTCAGCCTCCC TGGCCATCAGTGGGCTCCGGTCCGAGGACGAGGC TGATTATTACTGTGGTACTTGGGATTATAGCCTG AGTGGTTATGTCTTAGGCGGAGGCACCAAGCTGA CGGTCCTAGGC (SEQ ID NO: 178) |
| E5 | EVQLLESGGGLVQPGGSLRLSCAASGF TFS<u>DYYMS</u>WVRQAPGKGLEWVS<u>AIYSG GGSIYYADSVKG</u>RFTISRDNSKNTLYL QMNSLRAEDTAVYYCAR<u>DVQWNKAPRF DY</u>WGQGTLVTVSSGGGGSGGGGSGGGG SQSVLTQPPSASGAPGQRVTISC<u>SGSS SNIGSNDVS</u>WYQQLPGTAPKLLIY<u>ADS NRPS</u>GVPDRFSGSKSGTSASLAISGLR SEDEADYYC<u>GSWDYSLSGYV</u>FGGGTKL TVLG (SEQ ID NO: 171) | GAGGTGCAGCTGTTGGAGTCTGGGGGAGGCTTGG TACAGCCTGGGGGGTCCCTGAGACTCTCCTGTGC AGCCTCTGGATTCACCTTTAGCGATTATTATATG AGCTGGGTCCGCCAGGCTCCAGGGAAGGGGCTGG AGTGGGTCTCAGCGATCTATTCTGGTGGTGGTAG TATATATTACGCTGATTCTGTAAAAGGTCGGTTC ACCATCTCCAGAGACAATTCCAAGAACACGCTGT ATCTGCAAATGAACAGCCTGAGAGCCGAGGACAC GGCCGTGTATTACTGTGCGAGAGATGTTCAGTGG AATAAGGCTCCTCGTTTCGACTACTGGGGCCAGG GTACACTGGTCACCGTGAGCTCAGGTGGAGGCGG TTCAGGCGGAGGTGGATCCGGCGGTGGCGGATCG CAGTCTGTGCTGACTCAGCCACCCTCAGCGTCTG GGGCCCCCGGGCAGAGGGTCACCATCTCTTGTAG TGGCTCTTCATCTAATATTGGCAGTAATGATGTC TCCTGGTACCAGCAGCTCCCAGGAACGGCCCCCA AGCTCCTCATCTATGCTGATAGTAATCGGCCAAG CGGGGTCCCTGACCGATTCTCTGGCTCCAAGTCT GGCACCTCAGCCTCCCTGGCCATCAGTGGGCTCC GGTCCGAGGATGAGGCTGATTATTACTGTGGTTC TTGGGATTATAGCCTGAGTGGTTATGTCTTCGGC GGAGGTACCAAGCTGACGGTCCTAGGC (SEQ ID NO: 179) |
| E7 | EVQLLESGGGLVQPGGSLRLSCAASGF TFS<u>SYSMS</u>WVRQAPGKGLEWVS<u>GISHG GGNKYYADSVKG</u>RFTISRDNSKNTLYL QMNSLRAEDTAVYYCAR<u>DLRANNDTGF DY</u>WGQGTLVTVSSGGGGSGGGGSGGGG TQSVLTQPPSSSGTPGQRVTISC<u>TGSS SNIGSNAVT</u>WYQQLPGTAPKLLIY<u>DDN HRPS</u>GVPDRFSGSKSGTSASLAISGLR SEDEADYYC<u>GAWDYSLNAYV</u>FGGGTKL TVLG (SEQ ID NO: 172) | GAGGTGCAGCTGTTGGAGTCTGGGGGAGGCTTGG TACAGCCTGGGGGGTCCCTGAGACTCTCCTGTGC AGCCTCTGGATTCACCTTTAGCAGTTATTCTATG AGCTGGGTCCGCCAGGCTCCAGGGAAGGGGCTGG AGTGGGTCTCAGGGATCTCTCATGGTGGTGGTAA TAAATATTACGCTGATTCTGTAAAAGGTCGGTTC ACCATCTCCAGAGACAATTCCAAGAACACGCTGT ATCTGCAAATGAACAGCCTGAGAGCCGAGGACAC GGCCGTGTATTACTGTGCGAGAGATCTTAGGGCG AATAATGATACGGGTTTCGACTACTGGGGCCAGG GTACACTGGTCACCGTGAGCTCAGGTGGAGGCGG TTCAGGCGGAGGTGGATCCGGCGGTGGCGGAACG CAGTCTGTGCTGACTCAGCCACCCTCATCGTCTG GGACCCCCGGGCAGAGGGTCACCATCTCTTGTAC |

TABLE 9-continued

| scFv | Amino acid sequence of scFv | Coding nucleotide sequence of scFv |
|---|---|---|
| | | TGGCTCTTCATCTAATATTGGCAGTAATGCTGTC ACCTGGTACCAGCAGCTCCCAGGAACGGCCCCCA AACTCCTCATCTATGATGATAATCATCGGCCAAG CGGGGTCCCTGACCGATTCTCTGGCTCCAAGTCT GGCACCTCAGCCTCCCTGGCCATCAGTGGGCTCC GGTCCGAGGATGAGGCTGATTATTACTGTGGTGC TTGGGATTATAGCCTGAATGCTTATGTCTTCGGC GGAGGCACCAAGCTGACGGTCCTAGGC (SEQ ID NO: 180) |
| E10 | EVQLLESGGGLVQPGGSLRLSCAASGF TFSNYDMSWVRQAPGKGLEWVSLISHG GGNIYYADSVKGRFTISRDNSKNTLYL QMNSLRAEDTAVYYCARVPVMCTNHWC SYANGMDVWGQGTLVTVSSGGGGSGGG GSGGGGSQSVLTQPPSASGTPGQRVII SCSASSSNIGSNAVYWYQQLPGTAPKL LIYSDNQRPSGVPDRFSGSKSGTSASL AISGLRSEDEADYYCGSWDYSLSAYVF GGGTKLTVLG (SEQ ID NO: 173) | GAGGTGCAGCTGTTGGAGTCTGGGGGAGGCTTGG TACAGCCTGGGGGGTCCCTGAGACTCTCCTGTGC AGCCTCTGGATTCACCTTTAGCAATTATGATATG AGCTGGGTCCGCCAGGCTCCAGGGAAGGGGCTGG AGTGGGTCTCATTGATCTCTCATGGTGGTGGTAA TATATATTACGCTGATTCTGTAAAAGGTCGGTTC ACCATCTCCAGGGACAATTCCAAGAACACGCTGT ATCTGCAAATGAACAGCCTGAGAGCCGAGGACAC GGCCGTGTATTACTGTGCGAGAGTTCCTGTTATG TGTACTAATCATTGGTGTTCTTATGCTAATGGTA TGGACGTCTGGGGCCAGGGTACACTGGTCACCGT GAGCTCAGGTGGAGGCGGTTCAGGCGGAGGTGGA TCCGGCGGTGGCGGATCGCAGTCTGTGCTGACTC AGCCACCCTCAGCGTCTGGGACCCCCGGGCAGAG GGTCATCATCTCCTGTAGTGCCTCTTCATCTAAT ATTGGCAGTAATGCTGTCTACTGGTACCAGCAGC TCCCAGGAACGGCCCCCAAACTCCTCATCTATTC TGATAATCAGCGGCCAAGCGGGGTCCCTGACCGA TTCTCTGGCTCCAAGTCTGGCACCTCAGCCTCCC TGGCCATCAGTGGGCTCCGGTCCGAGGATGAGGC TGATTATTACTGTGGTGTTCTTGGGATTATAGCCTG AGTGCTTATGTCTTCGGCGGAGGCACCAAGCTGA CGGTCCTAGGC (SEQ ID NO: 181) |
| E11 | EVQLLESGGGLVQPGGSLRLSCAASGF TFSGYAMSWVRQAPGKGLEWVSGISHD GGNTYYADSVKGRFTISRDNSKNTLYL QMNSLRAEDTAVYYCARDRRKGPSTEF DYWGQGTLVTVSSGGGGSGGGGSGGGG SQSVLTQPPSLSGTPGQRVTISCTGSS SNIGSNSVSWYQQLPGTAPKLLIYDDN NRPSGVPDRFSGSKSGTSASLAISGLR SEDEADYYCGAWDYSLSAYVFGGGTKL TVLG (SEQ ID NO: 174) | GAGGTGCAGCTGTTGGAGTCTGGGGGAGGCTTGG TACAGCCTGGGGGGTCCCTGAGACTCTCCTGTGC AGCCTCTGGATTCACCTTTAGCGGTTATGCTATG AGCTGGGTCCGCCAGGCTCCAGGGAAGGGGCTGG AGTGGGTCTCAGGGATCTCTCATGATGGTGGTAA TACATATTACGCGGATTCTGTAAAAGGTCGGTTC ACCATCTCCAGAGACAATTCCAAGAACACGCTGT ATCTGCAAATGAACAGCCTGAGAGCCGAGGACAC GGCCGTGTATTACTGTGCGAGAGATCGTAGGAAG GGTCCTTCGACTGAGTTCGACTACTGGGGCCAGG GTACACTGGTCACCGTGAGCTCAGGTGGAGGCGG TTCAGGCGGAGGTGGATCCGGCGGTGGCGGATCG CAGTCTGTGCTGACTCAGCCACCCTCAGCGTCTG GGACCCCCGGGCAGAGGGTCACCATCTCTTGTAC TGGCTCTTCATCTAATATTGGCAGTAATTCTGTC TCCTGGTACCAGCAGCTCCCAGGAACGGCCCCCA AACTCCTCATCTATGATGATAATAATCGGCCAAG CGGGGTCCCTGACCGATTCTCTGGCTCCAAGTCT GGCACCTCAGCCTCCCTGGCCATCAGTGGGCTCC GGTCCGAGGATGAGGCTGATTATTACTGTGGTGC TTGGGATTATAGCCTGAGTGCTTATGTCTTCGGC GGAGGCACCAAGCTGACGGTCCTAGGC (SEQ ID NO: 182) |
| E12 | EVQLLESGGGLVQTGGSLRLSCAASGF TFSDYAMSWVRQAPGKGLEWVSWIYPG DSSIYYADSVKGRFTISRDNSKNTLYL QMNSLRAEDTAVYYCARLLSIDQAQLH YYYDAMDVWGQGTLVTVSSGGGGSGGG GSGGGGSQSVLTQPPSPSGTPGQRVTI SCTGSSSNIGNYYVYWYQQLPGTAPKL LIYANSHRPSGVPDRFSGSKSGTSASL AISGLRSEDEADYYCGSWDDSLSAYVF GGGTKLTVLG (SEQ ID NO: 175) | GAGGTGCAGCTGTTGGAGTCTGGGGGAGGCTTGG TACAGACTGGGGGGTCCCTGAGACTCTCCTGTGC AGCCTCTGGATTCACCTTTAGCGATTATGCTATG AGCTGGGTCCGCCAGGCTCCAGGGAAAGGGCTGG AGTGGGTCTCATGGATCTATCCTGGTGATAGTAG TATATATTACGCTGATTCTGTAAAGGTCGGTTC ACCATCTCCAGAGACAATTCCAAGAACACGCTGT ATCTGCAAATGAACAGCCTGAGAGCCGAGGACAC GGCCGTGTATTACTGTGCGAGACTTCTTAGTATT GATCAGGCTCAGTTGCATTATTATTATGATGCTA TGGACGTCTGGGGCCAGGGTACACTGGTCACCGT GAGCTCAGGTGGAGGCGGTTCAGGCGGAGGTGGA TCCGGCGGTGGCGGATCGCAGTCTGTGCTGACTC AGCCACCCTCAGCGTCTGGGACCCCCGGGCAGAG GGTCACCATCTCTTGTACTGGCTCTTCATCTAAT ATTGGCAATTATTATGTCTACTGGTACCAGCAGC TCCCAGGAACGGCCCCCAAACTCCTCATCTATGC TAATAGTCATCGGCCAAGCGGGGTCCCTGACCGA TTCTCTGGCTCCAAGTCTGGCACCTCAGCCTCCC |

TABLE 9-continued

| scFv | Amino acid sequence of scFv | Coding nucleotide sequence of scFv |
|---|---|---|
| | | TGGCCATCAGTGGGCTCCGGTCCGAGGATGAGGC<br>TGATTATTACTGTGGTTCTTGGGATGATAGCCTG<br>AGTGCTTATGTCTTCGGCGGAGGCACCAAGCTGA<br>CGGTCCTAGGC<br>(SEQ ID NO: 183) |

Example 2: Preparation of an Anti-c-Met/anti-VEGF Bispecific Antibody

Each of the 8 anti-VEGF scFvs prepared in the above Example 1 was fused at the c-terminus of the Fc region of the anti-c-Met antibody L3-1Y-IgG2 prepared in the above reference example 1. The fusion procedures are as follows.

A DNA segment having a nucleotide sequence (SEQ ID NO: 67) corresponding to the heavy chain of the anti-c-Met antibody L3-1Y-IgG2 prepared in above reference example 1 was inserted into a pcDNA™ 3.3-TOPO TA Cloning Kit (Cat no. 8300-01) which is included in OptiCHO™ Antibody Express Kit (Cat no. 12762-019) by Invitrogen Inc., and a DNA segment having a nucleotide sequence (SEQ ID NO: 69) corresponding to the light chain of the anti-c-Met antibody L3-1Y-IgG2 was inserted into a pOptiVEC™-TOPO TA Cloning Kit. Thereafter, the anti-VEGF scFv coding DNA prepared in Example 1 was fused at the c-terminus of the Fc region of L3-1Y-IgG2 inserted into pcDNA™ 3.3, using the coding DNA sequence of a linker peptide having 10 amino acid lengths consisting of (GGGGS)2, to construct vectors for the expression of bispecific antibodies.

The constructed vectors were each amplified using Qiagen Maxiprep kit (Cat no. 12662) and transiently expressed using the Freestyle™ MAX 293 Expression System (Invitrogen) in 293 F cells, cultured in suspension using FreeStyle™ 293 Expression Medium. One day prior to transient expression, the cells were prepared at a concentration of $5 \times 10^5$ cells/ml. Transient expression started when the number of the cells reached $1 \times 10^6$ cells/ml. Transfection was performed by a liposomal reagent method using Freestyle™ MAX reagent (Invitrogen). DNA was prepared in a 15-ml tube in a 3:2 ratio of heavy chain DNA:light chain DNA and mixed with 2 ml of OptiPro™ SFM (Invitrogen) (A), and 100 μl of Freestyle™ MAX reagent and 2 ml of OptiPro™ SFM were mixed in another 15-ml tube (B), and after (A) and (B) were mixed and incubated for 15 min., the mixture solution was then slowly mixed into the cells which were prepared one day before. After the transfection was complete, the cells were cultured in a 37° C., 80% humidity, 8% $CO_2$, 130 rpm incubator for 5 days.

The cultured cells were centrifuged to obtain 100 ml of supernatants, which were then purified using AKTA Prime (GE healthcare). The culture was flowed at a flow rate of 5 ml/min. onto the AKTA Prime installed with a Protein A column (GE healthcare, 17-0405-03) to perform elution using an IgG elution buffer (Thermo Scientific, 21004). The buffer was replaced by a PBS buffer to finally obtain purified bispecific anti-c-Met/anti-VEGF antibodies.

The prepared anti-c-Met/anti-VEGF bispecific antibodies wherein an anti-VEGF scFv is fused to the c-terminus of anti-c-Met antibody L3-1Y-IgG2 are respectively named as MV-15, MV-16, MV-17, MV-18, MV-19, MV-20, MV-21, or MV-22. The name of the anti-VEGF scFvs prepared in Example 1 and the name of anti-c-Met/anti-VEGF bispecific antibodies comprising each of the anti-VEGF scFvs were summarized in Table 10:

TABLE 10

| Name of an anti-VEGF scFy | Name of an anti-c-Met/anti-VEGF bispecific antibody |
|---|---|
| E2 | MV-15 |
| E2 | MV-16 |
| E3 | MV-17 |
| E5 | MV-18 |
| E7 | MV-19 |
| E10 | MV-20 |
| E11 | MV-21 |
| E12 | MV-22 |

Comparative Example: Preparation of a Fusion Protein of an Anti-c-Met Antibody and Ig2 Domain (VIG2)

Figure 9:
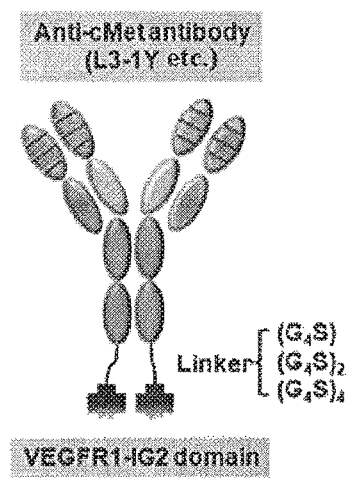
FIG. 9 is an illustration of an antibody capable of binding to c-Met and VEGF at the same time.

The anti-c-Met antibodies manufactured in Reference Example 1 were fused to a linker by coupling the C-terminal of their heavy chain therewith. Thereafter, an Ig2 domain, that is, amino acids from $129^{th}$ to $229^{th}$ among the amino acids constituting VEGF receptor 1 was sequentially fused at the terminal of the linker to manufacture antibodies capable of binding to c-Met and VEGF at the same time. FIG. 9 provides an illustration.

Among 1338 amino acids constituting VEGF receptor 1 (P17948.2; SEQ ID NO: 184), a gene sequence encoding 101 amino acids from $129^{th}$ to $229^{th}$ constituting the Ig2 domain which has been shown to be most important for VEGF-binding was secured from NCBI database.

Amino acid sequence of Ig2 domain (VIG2)
(SEQ ID NO: 185):
SDTGRPFVEMYSEIPEIIHMTEGRELVIPCRVTSPNITVTLKKFPLDTL

IPDGKRIIWDSRKGFIISNATYKEIGLLTCEATVNGHLYKTNYLTHRQT

NTI

Nucleotide sequence of Ig2 domain (VIG2)
(SEQ ID NO: 186):
AGTGATACAGGTAGACCTTTCGTAGAGATGTACAGTGAAATCCCCGAAAT

TATACACATGACTGAAGGAAGGGAGCTCGTCATTCCCTGCCGGGTTACGT

CACCTAACATCACTGTTACTTTAAAAAAGTTTCCACTTGACACTTTGATC

CCTGATGGAAAACGCATAATCTGGGACAGTAGAAAGGGCTTCATCATATC

AAATGCAACGTACAAAGAAATAGGGCTTCTGACCTGTGAAGCAACAGTCA

ATGGGCATTTGTATAAGACAAACTATCTCACACATCGACAAACCAATACA

ATC

In order to couple the heavy chain of the c-Met antibody manufactured in the above and the Ig2 domain (VIG2), three types of linkers were designed having repeating GGGGS motifs: 'GGGGS'(G4S), (SEQ ID NO: 187) 'GGGGSGGGGS'((G4S)2) (SEQ ID NO: 188), or 'GGGGSGGGGSGGGGSGGGGS'((G4S)4) (SEQ ID NO: 189). The peptide linker was to be placed between the c-Met antibody and the Ig2 domain (VIG2) of VEGF receptor 1. Accordingly, a gene was synthesized that encoded the heavy chain of the anti-c-Met antibody, the linker sequence, and the VEGF-binding fragment. The synthesized gene also included a stop codon (TGA) at the end of the designed final gene. The synthesized gene was inserted into pOptivec vector (Invitrogen) using an EcoRI/XhoI cloning site to produce a heavy chain expression vector. The vector used in the manufacture of L3-1Y/IgG2 was used as a light chain expression vector.

Each of the constructed vectors were amplified using Qiagen Maxiprep kit (Cat no. 12662), and the vector including the heavy chain and the vector containing the light chain were transfected at the ratio of 4:1 (80 ug:20 ug) into 293T cells ($2.5 \times 10^7$ cells) to which 360 μl of 2 M $CaCl_2$ was added. Thereafter, the transfected cells were cultured in a DMEM medium containing 10% FBS at 37° C. in 5% $CO_2$ conditions for 5 hours, and then cultured in an FBS-free DMEM medium at 37° C. in 5% $CO_2$ conditions for 48 hours.

The cultured cells were centrifuged to obtain 100 ml of each supernatant, which was purified using AKTA Prime (GE Healthcare). Protein A column (GE Healthcare, 17-0405-03) was placed in the AKTA Prime, and the cultured solution flowed at a rate of 5 ml/min and was eluted with IgG elution buffer (Thermo Scientific, 21004). The buffer was exchanged with a PBS buffer, and thus antibodies capable of binding to cMet and VEGF at the same time were finally purified.

The prepared fusion proteins were named as shown in Table 11:

TABLE 11

| | Name | Heavy Chain | Hinge | Constant Region | Linker | Light Chain | VEGF-binding fragment |
|---|---|---|---|---|---|---|---|
| Fusion protein | MV10AY | SEQ ID NO: 62 | U6-HC7 (SEQ ID NO: 101) | IgG1 | (G4S)2 | SEQ ID NO: 68 | VIG2 (SEQ ID NO: 185) |
| | MV10AY U3 HC9/ IgG1 | SEQ ID NO: 64 | U3 HC9 (SEQ ID NO: 102) | IgG1 | (G4S)2 | SEQ ID NO: 68 | VIG2 (SEQ ID NO: 185) |
| | MV10AY U3 HC9/ IgG2 | SEQ ID NO: 66 | U3 HC9 (SEQ ID NO: 102) | IgG2 | (G4S)2 | SEQ ID NO: 68 | VIG2 (SEQ ID NO: 185) |

Among the prepared fusion proteins, MV10AY U3 HC9/IgG2 was selected for use in the below experiments as a comparative group.

Example 3: Examination of Activities of the Anti-c-Met/Anti-VEGF Bispecific Antibody as an Anti-c-Met Antibody 3.1. Binding Affinity to c-Met An examination on whether the anti-c-Met/anti-VEGF bispecific antibody maintains binding affinity to c-Met was conducted using Biacore T100(GE). A human Fab binding agent (GE Healthcare) was immobilized onto a CM5 chip (#BR-1005-30, GE) according to the manufacturer's instructions. About 90~120 RU of the anti-c-Met/anti-VEGF bispecific antibody was captured, and c-Met-Fc (#358-MT/CF, R&D Systems) was injected thereto at various concentrations. Then, 10 mM Glycine-HCl (pH 2.1) solution was injected thereto to regenerate the surface. The obtained data were fitted using BIAevaluation software (GE Healthcare, Biacore T100 evaluation software), to measure the binding affinity to c-Met.

The obtained results are shown in Table 12:

TABLE 12

| Binding affinity to c-Met | | | | | | | | |
|---|---|---|---|---|---|---|---|---|
| BsAb | MV-15 | MV-16 | MV-17 | MV-18 | MV-19 | MV-20 | MV-21 | MV-22 |
| KD(nM) | 0.10 | 0.21 | 0.09 | 0.05 | 0.30 | 0.04 | 0.04 | 0.06 |

As shown in Table 12, all of the 8 bispecific antibodies prepared in Example 2 have excellent c-Met binding affinity of about 0.2 nM or less.

3.2. c-Met Degradation

An examination on whether the 8 anti-c-Met/anti-VEGF bispecific antibodies prepared in Example 2 maintain the activity of c-Met degradation was conducted through ELISA using MKN45 cell line. Based on the fact that the c-Met antibody included in the bispecific antibody binds to c-Met, thereby inducing internalization and degradation of c-Met, the efficacy of the bispecific antibody can be examined by measuring the increase or decrease of total amount of c-Met.

In particular, the amount c-Met was measured using quantitative ELISA, wherein human total HGF R/c-Met ELISA kit (R&D systems) and the gastric cancer cell line MKN45 (JCRB0254; Health Science Research Resource Bank; HSRRB, Shinjuku, Japan) were used for the assay. 200,000 cells/ml were mixed with 5 ug/ml of each of the anti-c-Met/anti-VEGF bispecific antibodies, and cultured for 24 hours (medium: RPMI with 10% Fetal Bovine Serum), and then, subjected to ELISA, wherein Super Aquablue (eBiosciences) was used for the assay and colorimetric signals were measured by OD values at 450 nm wavelength.

The values obtained from groups treated with the an anti-c-Met/anti-VEGF bispecific antibodies were calculated as relative values compared to that of antibody non-treated group ("media"; supposing the value of "media" as "100%"). For comparison, the same experimentations were conducted for groups treated with anti-c-Met antibody L3-1Y/IgG2 prepared in the reference example and fusion protein MV10AY prepared in the comparative example.

Figure 2:
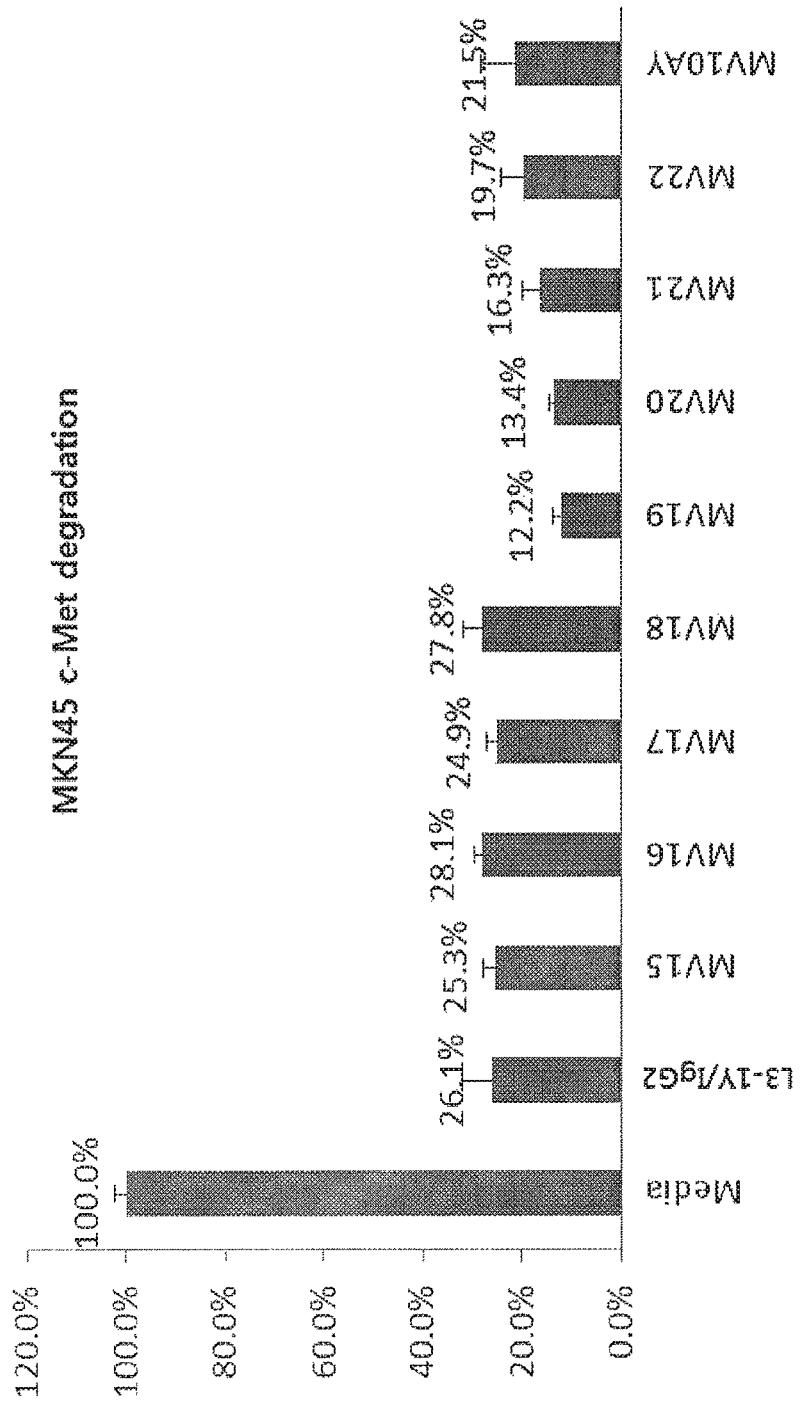
FIG. 2 is a graph showing c-Met degrading activity of various anti-c-Met/anti-VEGF bispecific antibodies.

The obtained results are shown in FIG. 2. As shown in FIG. 2, the c-Met degradation activities of the anti-c-Met/anti-VEGF bispecific antibodies are equal to or more than those of anti-c-Met antibody L3-1Y/IgG2, indicating that the anti-c-Met/anti-VEGF bispecific antibodies maintain the c-Met degradation activities of the anti-c-Met antibody comprised therein.

3.3. Akt Phosphorylation Inhibition

An examination on whether the 8 anti-c-Met/anti-VEGF bispecific antibodies prepared in Example 2 maintain the activity of Akt phosphorylation was conducted for Caki-1 cell line.

The phosphorylation site of Akt is the $473^{rd}$ position (Ser 473), and thus, PathScan phospho-AKT1 (Ser473) chemiluminescent Sandwich ELISA kit (Cell signaling) were used for the examination. Renal cancer cell line Caki-1 (HTB-46; American Type Culture Collection (ATCC), Manassas, Va.) was cultured and one day after, 200,000 cells/ml of the cultured renal cancer cell line Caki-1 were treated with a mixture of 5 ug/ml of each of the anti-c-Met/anti-VEGF bispecific antibodies and serum-free DMEM medium (GIBCO, Invitrogen) for 30 minutes, and then subjected to ELISA using the ELISA kit. The change in Akt phosphorylation upon treatment with the anti-c-Met antibody or anti-c-Met/anti-VEGF bispecific antibodies is calculated by comparing to the change in Akt phosphorylation upon treatment with the positive control 5D5 anti-c-Met antibody (isolated and purified from hybridoma (American Type Culture Collection; ATCC Cat. # HB11895, Manassas, Va.)). For comparison, the same experiments were conducted for an antibody non-treated group ("media"), groups treated with anti-c-Met antibody L3-1Y/IgG2 prepared in the reference example and fusion protein MV10AY prepared in the comparative example.

Figure 3:
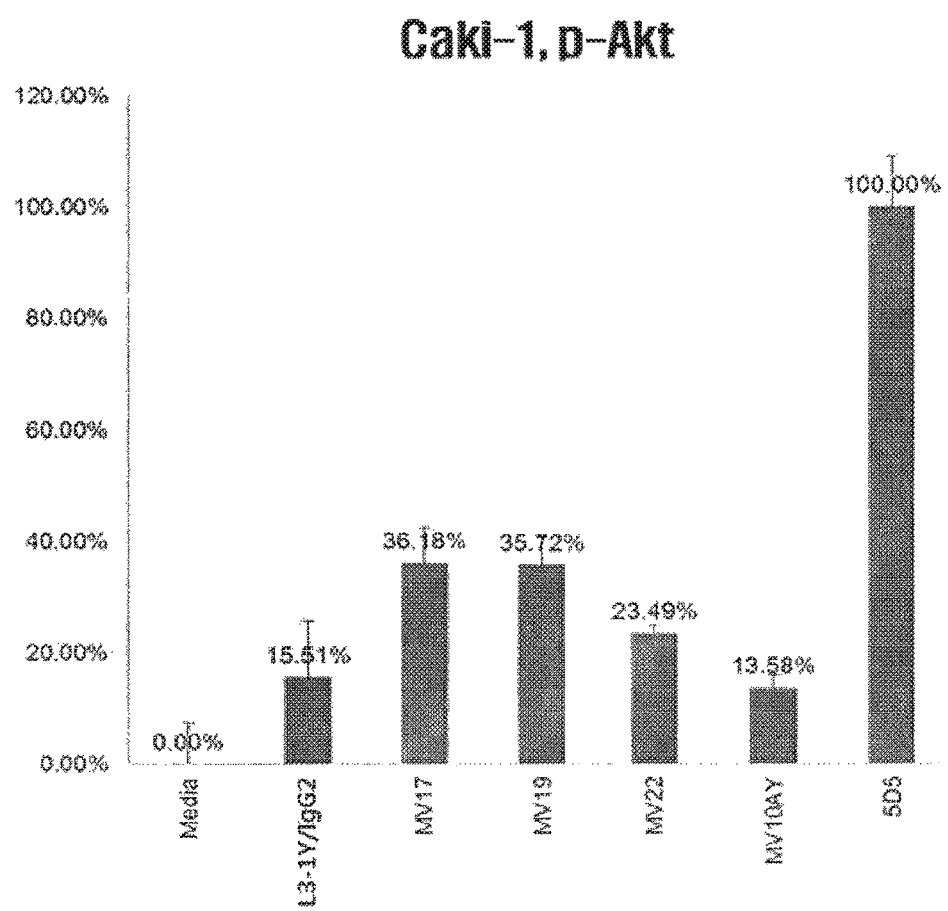
FIG. 3 is a graph showing Akt phosphorylation inhibiting activity of various anti-c-Met/anti-VEGF bispecific antibodies.

As shown in FIG. 3, the anti-c-Met/anti-VEGF bispecific antibodies prepared in Example 2 maintain the Akt phosphorylation inhibiting activities of the anti-c-Met antibody comprised therein, and show considerably increased inhibition of Akt phosphorylation compared to the 5D5 antibody.

3.4. Inhibition of Gastric Cancer Cell Proliferation

The cancer cell proliferation inhibiting activities of the 8 anti-c-Met/anti-VEGF bispecific antibodies prepared in Example 2 were examined for gastric cancer cell line MKN45.

Human gastric cancer cell line MKN45 (JCRB0254) was provided from Health Science Research Resource Bank (HSRRB, Shinjuku, Japan). The cells were cultured in RPMI1640 medium (GIBCO, Cat. #11875-119) supplemented with 10% (v/v) fetal bovine serum (FBS, GIBCO Cat. #16000-044) and 1% (v/v) penicillin/streptomycin (GIBCO, Cat. #15410-122), under 5% $CO_2$-containing wetting atmosphere at 37° C., and subcultured before confluence. The cells were counted by CEDEX Analyzer (Roche Diagnostics). The cancer cell proliferation by treatment with an antibody (in vitro) was examined by a luminescent assay using Celltiter Glo (CTG: Promega, USA).

The assay was conducted according to the manufacturer's manual. In brief, the MKN45 cells in FBS 10% (v/v)-contained RPMI1640 medium were seeded onto a black 96-well plate (Corning Incorporated, Cat. #Costar 3603) at the concentration of $1 \times 10^4$ cells/well. The antibodies were diluted in 10% FBS-contained RPMI1640 medium at the final concentration of 0.008 μg/mL, 0.04 μg/mL, 0.2 μg/mL, and 1 μg/mL, respectively and added to the cells. After a 72 hour incubation, 100 μL of CTG solution was added to each well, and further incubation was performed at room temperature for 30 minutes. The obtained luminescent signals were recorded using Envision 2104 Multi-label Reader (Perkin Elmer, Waltham, Mass., USA). For comparison, the same experimentations were conducted for groups treated with anti-c-Met antibody L3-1Y/IgG2 prepared in the reference example and fusion protein MV10AY prepared in the comparative example.

Figure 4:
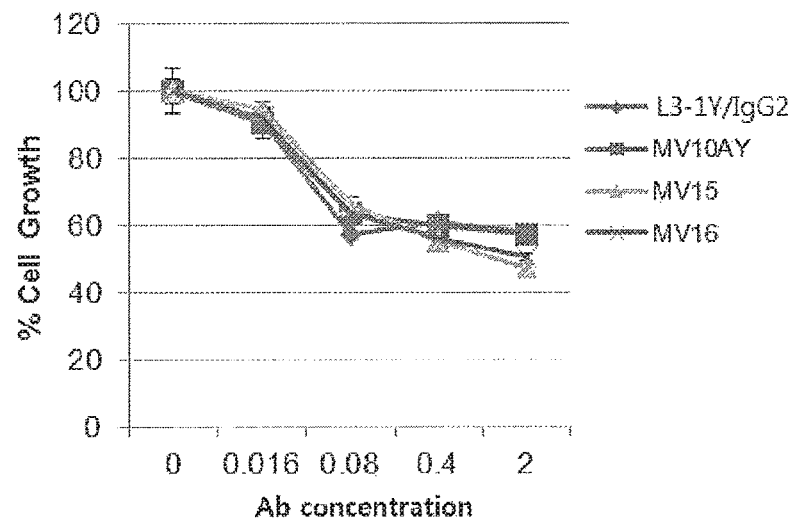
FIG. 4 is a graph showing cancer cell (gastric cancer cell line MKN45) growth inhibiting activity of various anti-c-Met/anti-VEGF bispecific antibodies.
Figure 5:
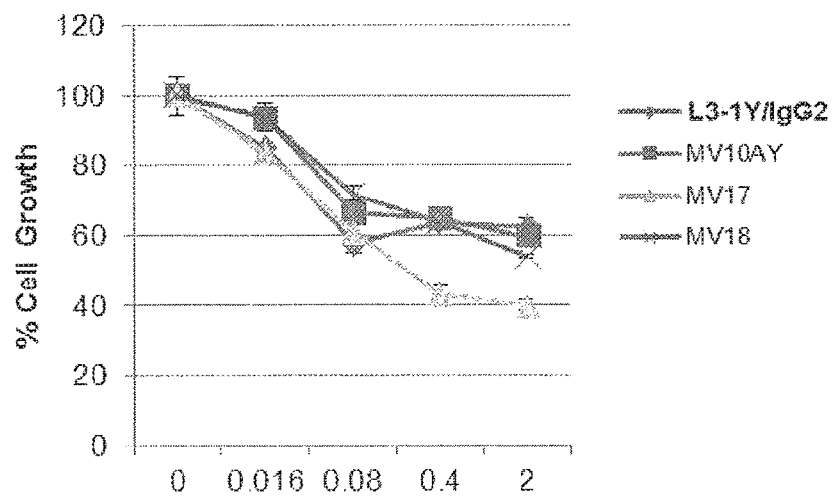
FIG. 5 is a graph showing cancer cell (gastric cancer cell line MKN45) growth inhibiting activity of various anti-c-Met/anti-VEGF bispecific antibodies.
Figure 6:
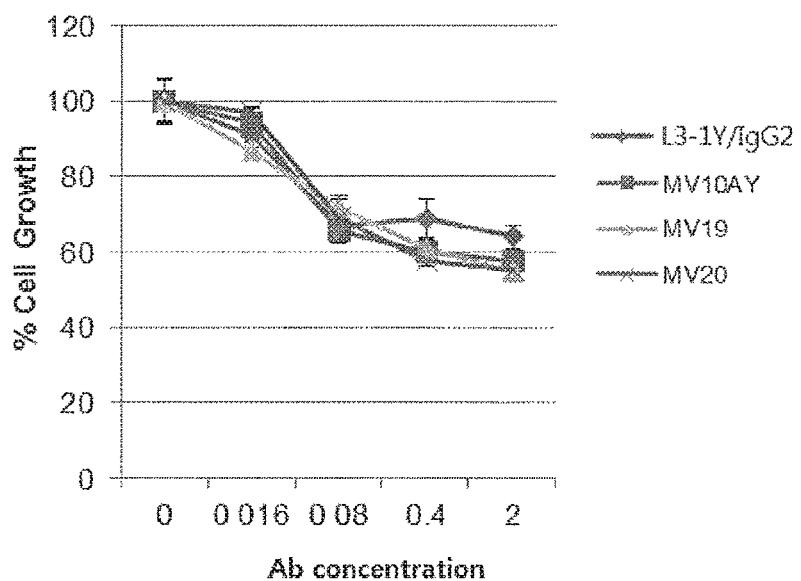
FIG. 6 is a graph showing cancer cell (gastric cancer cell line MKN45) growth inhibiting activity of various anti-c-Met/anti-VEGF bispecific antibodies.
Figure 7:
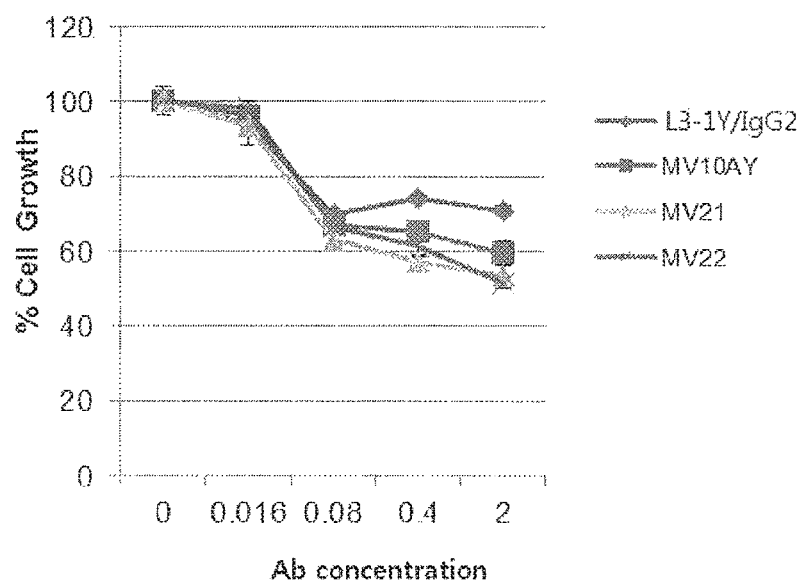
FIG. 7 is a graph showing cancer cell (gastric cancer cell line MKN45) growth inhibiting activity of various anti-c-Met/anti-VEGF bispecific antibodies.

The results are shown in FIG. 4 (MV-15 and MV-16), FIG. 5 (MV-17 and MV-18), FIG. 6 (MV-19 and MV-20), and FIG. 7 (MV-21 and MV-22). As shown in FIGS. 4-7, all the 8 anti-c-Met/anti-VEGF bispecific antibodies prepared in Example 2 exhibit increased inhibition of cancer cell proliferation compared to the anti-c-Met antibody L3-1Y/IgG2 and MV10AY.

Example 4: Activities of the Anti-c-Met/Anti-VEGF Bispecific Antibody as an Anti-VEGF Antibody 4.1. VEGF Binding Affinity An examination on whether the 8 anti-c-Met/anti-VEGF bispecific antibodies prepared in Example 2 maintains binding affinity to VEGF was conducted using Biacore T100 (GE). VEGF (R&D systems) immobilized on the surface of CM5 chip (#BR-1005-30, GE) by amino coupling according to the manufacturer's instructions. About 90~120 RU of the anti-c-Met/anti-VEGF bispecific antibody was captured, and VEGF-Fc (#358-MT/CF, R&D Systems) was injected thereto at various concentrations. Then, a solution containing 1M NaCl and 5 mM NaOH was injected thereto to regenerate the surface. The obtained data were fitted using BIAevaluation software (GE Healthcare, Biacore T100 evaluation software), to measure the binding affinity to VEGF.

The obtained results are shown in Table 13:

TABLE 13

| BsAb | Binding affinity to VEGF | | | | | | | |
| --- | --- | --- | --- | --- | --- | --- | --- | --- |
| | MV-15 | MV-16 | MV-17 | MV-18 | MV-19 | MV-20 | MV-21 | MV-22 |
| KD(nM) | 6.83 | 14.78 | 5.76 | 4.23 | 1.00 | 4.43 | 8.27 | 2.20 |

As shown in Table 13, all of the 8 bispecific antibodies prepared in Example 2 have VEGF binding affinity of about 15 nM or less.

4.2. Inhibition of Migration of Human Umbilical Vein Endothelial Cell (HUVEC)

In this example, it was examined whether the 8 anti-c-Met/anti-VEGF bispecific antibodies prepared in Example 2 inhibit the migration of human umbilical vein endothelial cell (HUVEC), which is generally exhibited by anti-VEGF antibodies. To examine the migration inhibiting effect by treatment with an antibody (in vitro), the following assay was performed. Since the cell migration directly participates in cancer metastasis, the following assay is widely used for examine cell metastasis ability.

Oris™ Cell migration assay using Oris 96-well plate (Platypus Technologies) was performed. 10000 cells of HUVEC (ATCC) were seeded in each well of 96-well plate equipped with a stopper, and cultured in serum-free medium (EBM, Lonza) for 24 hours with treatment with 0.4 µg/ml of HGF (R&D systems) and 0.4 µg/ml of VEGF (R&D systems), followed by removing the stopper. The stopper, which is a circular rubber object, prevents cell growth, and thus, when it is removed after 24 hour incubation, a circular space (cell-free space), wherein no cells exist, is formed.

After removing the stopper, cells were treated at various concentrations (0.05 to 10 µg/ml) with MV-19 and MV-22 antibodies prepared in Example 1, an anti-c-Met antibody L3-1Y, and antibody MV10AY, and 24 hours after, the cells were stained with fluorescent material, calcein AM (BD), wherein only cells are stained, and the cell-free space remains non-stained part. Therefore, as inhibition of cell migration is increased, the non-stained space becomes larger, and thus, the degree of cell migration can be examined by measuring the size of the non-stained space. The fluorescent intensity was read using multilabel reader (Perkin-Elmer, Envision), and the obtained values were converted by comparing the fluorescent intensity of VEGF+HGF treated group ("media"; antibody non-treated group; the value of which is supposed as 100%).

Figure 8:
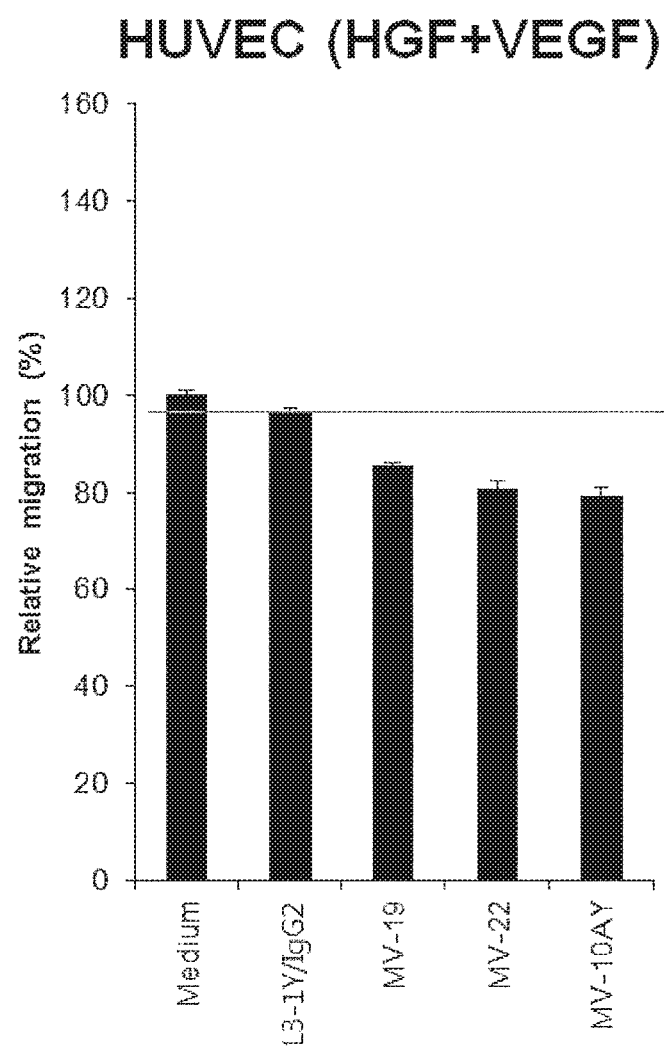
FIG. 8 is a graph showing an activity of various anti-c-Met/anti-VEGF bispecific antibodies to inhibit migration of human umbilical vein endothelial cell (HUVEC).

The results at the antibody concentration of 10 µg/ml are shown in FIG. 8. As shown in FIG. 8, the inhibition of cell migration of the anti-c-Met/anti-VEGF bispecific antibodies prepared in Example 2 is considerably increased compared to that of the anti-c-Met antibody L3-1Y/IgG2, and equal to that of MV10AY.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. An anti-VEGF antibody or an antigen-binding fragment thereof comprising
a CDR-H1 comprising the amino acid sequence of SEQ ID NO: 110, a CDR-H2 comprising the amino acid sequence of SEQ ID NO: 121, a CDR-H3 comprising the amino acid sequence of SEQ ID NO: 129, a CDR-L1 comprising the amino acid sequence of SEQ ID NO: 137, a CDR-L2 comprising the amino acid sequence of SEQ ID NO: 145, and a CDR-L3 comprising the amino acid sequence of SEQ ID NO: 151.

2. The anti-VEGF antibody or an anti-VEGF antigen-binding fragment of claim 1, wherein the anti-VEGF antibody or the anti-VEGF antigen-binding fragment comprises
a heavy chain variable region comprising the amino acid sequence of SEQ ID NO: 159 and a light chain variable region comprising the amino acid sequence of SEQ ID NO: 167.

3. The anti-VEGF antibody or an antigen-binding fragment thereof of claim 1, which is an anti-VEGF scFv comprising SEQ ID NO: 175.

4. A pharmaceutical composition comprising the anti-VEGF antibody or an antigen-binding fragment thereof of claim 1, and a pharmaceutically acceptable carrier.

5. A method of treating a cancer in a subject, comprising administering a therapeutically effective amount of the anti-VEGF antibody or the antigen-binding fragment thereof of claim 1 to the subject to inhibit cancer cell growth, thereby treating the cancer.

6. The anti-VEGF antibody or an antigen-binding fragment thereof of claim 1, which is an scFv, (scFv)2, scFvFc, Fab, or Fab'.

7. An anti-c-Met/anti-VEGF bispecific antibody comprising an anti-c-Met antibody that comprises two heavy chains and two light chains and an scFv of the anti-VEGF antibody linked to the C-terminus of each anti-c-Met antibody heavy chain, wherein the anti-c-Met heavy chain comprises
a CDR-H1 comprising the amino acid sequence of SEQ ID NO: 1, a CDR-H2 comprising the amino acid sequence of SEQ ID NO: 2, a CDR-H3 comprising the amino acid sequence of SEQ ID NO: 3;
the anti-c-Met light chain comprises a CDR-L1 comprising the amino acid sequence of SEQ ID NO: 10, a CDR-L2 comprising the amino acid sequence of SEQ ID NO: 11, and a CDR-L3 comprising the amino acid sequence of SEQ ID NO: 13;
and the anti-VEGF scFv comprises a CDR-H1 comprising the amino acid sequence of SEQ ID NO: 110, a CDR-H2 comprising the amino acid sequence of SEQ ID NO: 121, a CDR-H3 comprising the amino acid sequence of SEQ ID NO: 129, a CDR-L1 comprising the amino acid sequence of SEQ ID NO: 137, a CDR-L2 comprising the amino acid sequence of SEQ ID NO: 145, and a CDR-L3 comprising the amino acid sequence of SEQ ID NO: 151.

8. The anti-c-Met/anti-VEGF bispecific antibody of claim 7, wherein the anti-c-Met heavy chain comprises
SEQ ID NO: 17, and
the anti-c-Met light chain comprises SEQ ID NO: 18.

9. An anti-c-Met/anti-VEGF bispecific antibody of claim 7, wherein the anti-c-Met heavy chain comprises
SEQ ID NO: 62, the $18^{th}$ to $462^{nd}$ positions of SEQ ID NO: 62, SEQ ID NO: 64, the $18^{th}$ to $461^{st}$ positions of SEQ ID NO: 64, SEQ ID NO: 66, or the $18^{th}$ to $460^{th}$ positions of SEQ ID NO: 66; and
the anti-c-Met light chain comprises SEQ ID NO: 68, the $21^{st}$ to $240^{th}$ positions of SEQ ID NO: 68, SEQ ID NO: 70, or the $21^{st}$ to $240^{th}$ positions of SEQ ID NO: 70.

10. A pharmaceutical composition comprising the anti-c-Met/anti-VEGF bispecific antibody of claim 7, and a pharmaceutically acceptable carrier.

11. A method of treating a cancer in a subject, comprising administering a therapeutically effective amount of-the anti-c-Met/anti-VEGF bispecific antibody of claim 7 to the subject to inhibit cancer cell growth, thereby treating the cancer.

12. The anti-c-Met/anti-VEGF bispecific antibody of claim 7, wherein the anti-VEGF scFv comprises SEQ ID NO: 175.

* * * * *

SEQUENCE LISTING

```
<160> NUMBER OF SEQ ID NOS: 190

<210> SEQ ID NO 1
<211> LENGTH: 5
<212> TYPE: PRT
<213> ORGANISM: Artificial Sequence
<220> FEATURE:
<223> OTHER INFORMATION: Synthetic heavy chain CDR1 of AbF46

<400> SEQUENCE: 1

Asp Tyr Tyr Met Ser
 1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic heavy chain CDR2 of AbF46
```

-continued

```
<400> SEQUENCE: 2

Phe Ile Arg Asn Lys Ala Asn Gly Tyr Thr Thr Glu Tyr Ser Ala Ser
 1               5                  10                  15

Val Lys Gly

<210> SEQ ID NO 3
<211> LENGTH: 6
<212> TYPE: PRT
<213> ORGANISM: Artificial Sequence
<220> FEATURE:
<223> OTHER INFORMATION: Synthetic heavy chain CDR3 of AbF46

<400> SEQUENCE: 3

Asp Asn Trp Phe Ala Tyr
 1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic heavy chain CDR1 of c-Met antibody
<220> FEATURE:
<221> NAME/KEY: MOD_RES
<222> LOCATION: (1)
<223> OTHER INFORMATION: Xaa is Pro or Ser or absent
<220> FEATURE:
<221> NAME/KEY: MOD_RES
<222> LOCATION: (2)
<223> OTHER INFORMATION: Xaa is Glu or Asp

<400> SEQUENCE: 4

Xaa Xaa Tyr Tyr Met Ser
 1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic heavy chain CDR2 of c-Met antibody
<220> FEATURE:
<221> NAME/KEY: MOD_RES
<222> LOCATION: (3)
<223> OTHER INFORMATION: Xaa is Asn or Lys
<220> FEATURE:
<221> NAME/KEY: MOD_RES
<222> LOCATION: (4)
<223> OTHER INFORMATION: Xaa is Ala or Val
<220> FEATURE:
<221> NAME/KEY: MOD_RES
<222> LOCATION: (7)
<223> OTHER INFORMATION: Xaa is Asn or Thr

<400> SEQUENCE: 5

Arg Asn Xaa Xaa Asn Gly Xaa Thr
 1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic heavy chain CDR3 of c-Met antibody
<220> FEATURE:
<221> NAME/KEY: MOD_RES
<222> LOCATION: (5)
<223> OTHER INFORMATION: Xaa is Ser or Thr
```

-continued

```
<400> SEQUENCE: 6

Asp Asn Trp Leu Xaa Tyr
 1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic light chain CDR1 of c-Met antibody
<220> FEATURE:
<221> NAME/KEY: MOD_RES
<222> LOCATION: (4)
<223> OTHER INFORMATION: Xaa is His, Arg, Gln or Lys
<220> FEATURE:
<221> NAME/KEY: MOD_RES
<222> LOCATION: (12)
<223> OTHER INFORMATION: Xaa is His or Gln
<220> FEATURE:
<221> NAME/KEY: MOD_RES
<222> LOCATION: (13)
<223> OTHER INFORMATION: Xaa is Lys or Asn
<220> FEATURE:
<221> NAME/KEY: MOD_RES
<222> LOCATION: (9)
<223> OTHER INFORMATION: Xaa is Ser or Trp

<400> SEQUENCE: 7

Lys Ser Ser Xaa Ser Leu Leu Ala Xaa Gly Asn Xaa Xaa Asn Tyr Leu
 1               5                  10                  15

Ala

<210> SEQ ID NO 8
<211> LENGTH: 7
<212> TYPE: PRT
<213> ORGANISM: Artificial Sequence
<220> FEATURE:
<223> OTHER INFORMATION: Synthetic light chain CDR2 of c-Met antibody
<220> FEATURE:
<221> NAME/KEY: MOD_RES
<222> LOCATION: (2)
<223> OTHER INFORMATION: Xaa is Ala or Gly
<220> FEATURE:
<221> NAME/KEY: MOD_RES
<222> LOCATION: (4)
<223> OTHER INFORMATION: Xaa is Thr or Lys
<220> FEATURE:
<221> NAME/KEY: MOD_RES
<222> LOCATION: (7)
<223> OTHER INFORMATION: Xaa is Ser or Pro

<400> SEQUENCE: 8

Trp Xaa Ser Xaa Arg Val Xaa
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic light chain CDR3 of c-Met antibody
<220> FEATURE:
<221> NAME/KEY: MOD_RES
<222> LOCATION: (1)
<223> OTHER INFORMATION: Xaa is Gly, Ala or Gln
<220> FEATURE:
<221> NAME/KEY: MOD_RES
<222> LOCATION: (6)
<223> OTHER INFORMATION: Xaa is Arg, His, Ser, Ala, Gly or Lys
<220> FEATURE:
<221> NAME/KEY: MOD_RES
<222> LOCATION: (8)
```

```
<223> OTHER INFORMATION: Xaa is Leu, Tyr, Phe or Met

<400> SEQUENCE: 9

Xaa Gln Ser Tyr Ser Xaa Pro Xaa Thr
 1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic light chain CDR1 of AbF46

<400> SEQUENCE: 10

Lys Ser Ser Gln Ser Leu Leu Ala Ser Gly Asn Gln Asn Asn Tyr Leu
 1               5                  10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic light chain CDR2 of AbF46

<400> SEQUENCE: 11

Trp Ala Ser Thr Arg Val Ser
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic light chain CDR3 of AbF46

<400> SEQUENCE: 12

Gln Gln Ser Tyr Ser Ala Pro Leu Thr
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic CDR-L3 derived from L3-1 clone

<400> SEQUENCE: 13

Gln Gln Ser Tyr Ser Arg Pro Tyr Thr
 1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic CDR-L3 derived from L3-2 clone

<400> SEQUENCE: 14

Gly Gln Ser Tyr Ser Arg Pro Leu Thr
 1               5

<210> SEQ ID NO 15
<211> LENGTH: 9
<212> TYPE: PRT
<213> ORGANISM: Artificial Sequence
```

```
<220> FEATURE:
<223> OTHER INFORMATION: Synthetic CDR-L3 derived from L3-3 clone

<400> SEQUENCE: 15

Ala Gln Ser Tyr Ser His Pro Phe Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic CDR-L3 derived from L3-5 clone

<400> SEQUENCE: 16

Gln Gln Ser Tyr Ser Arg Pro Phe Thr
 1               5

<210> SEQ ID NO 17
<211> LENGTH: 117
<212> TYPE: PRT
<213> ORGANISM: Artificial Sequence
<220> FEATURE:
<223> OTHER INFORMATION: Synthetic heavy chain variable region of anti
      c-Met humanized antibody(huAbF46-H4)

<400> SEQUENCE: 17

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 18
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 18

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
        50                  55                  60
```

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Tyr Thr Phe Gly Gln Gly Thr Lys Val Glu Ile
            100                 105                 110

Lys Arg

<210> SEQ ID NO 19
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gly Gln
                85                  90                  95

Ser Tyr Ser Arg Pro Leu Thr Phe Gly Gln Gly Thr Lys Val Glu Ile
            100                 105                 110

Lys Arg

<210> SEQ ID NO 20
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Lys Pro Gly Lys
            35                  40                  45

Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Ala Gln
                85                  90                  95

Ser Tyr Ser His Pro Phe Ser Phe Gly Gln Gly Thr Lys Val Glu Ile
            100                 105                 110

Lys Arg

```
<210> SEQ ID NO 21
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 21

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Arg Pro Phe Thr Phe Gly Gln Gly Thr Lys Val Glu Ile
            100                 105                 110

Lys Arg

<210> SEQ ID NO 22
<211> LENGTH: 6
<212> TYPE: PRT
<213> ORGANISM: Artificial Sequence
<220> FEATURE:
<223> OTHER INFORMATION: Synthetic CDR-H1 derived from H11-4 clone

<400> SEQUENCE: 22

Pro Glu Tyr Tyr Met Ser
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic CDR-H1 derived from YC151 clone

<400> SEQUENCE: 23

Pro Asp Tyr Tyr Met Ser
 1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic CDR-H1 derived from YC193 clone

<400> SEQUENCE: 24

Ser Asp Tyr Tyr Met Ser
 1               5

<210> SEQ ID NO 25
<211> LENGTH: 8
<212> TYPE: PRT
<213> ORGANISM: Artificial Sequence
<220> FEATURE:
```

<223> OTHER INFORMATION: Synthetic CDR-H2 derived from YC244 clone

<400> SEQUENCE: 25

Arg Asn Asn Ala Asn Gly Asn Thr
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic CDR-H2 derived from YC321 clone

<400> SEQUENCE: 26

Arg Asn Lys Val Asn Gly Tyr Thr
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic CDR-H3 derived from YC354 clone

<400> SEQUENCE: 27

Asp Asn Trp Leu Ser Tyr
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic CDR-H3 derived from YC374 clone

<400> SEQUENCE: 28

Asp Asn Trp Leu Thr Tyr
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic CDR-L1 derived from L1-1 clone

<400> SEQUENCE: 29

Lys Ser Ser His Ser Leu Leu Ala Ser Gly Asn Gln Asn Asn Tyr Leu
1               5                   10                  15

Ala

<210> SEQ ID NO 30
<211> LENGTH: 17
<212> TYPE: PRT
<213> ORGANISM: Artificial Sequence
<220> FEATURE:
<223> OTHER INFORMATION: Synthetic CDR-L1 derived from L1-3 clone

<400> SEQUENCE: 30

Lys Ser Ser Arg Ser Leu Leu Ser Ser Gly Asn His Lys Asn Tyr Leu
1               5                   10                  15

Ala

<210> SEQ ID NO 31
<211> LENGTH: 17

```
<212> TYPE: PRT
<213> ORGANISM: Artificial Sequence
<220> FEATURE:
<223> OTHER INFORMATION: Synthetic CDR-L1 derived from L1-4 clone

<400> SEQUENCE: 31

Lys Ser Ser Lys Ser Leu Leu Ala Ser Gly Asn Gln Asn Asn Tyr Leu
  1               5                  10                  15

Ala

<210> SEQ ID NO 32
<211> LENGTH: 17
<212> TYPE: PRT
<213> ORGANISM: Artificial Sequence
<220> FEATURE:
<223> OTHER INFORMATION: Synthetic CDR-L1 derived from L1-12 clone

<400> SEQUENCE: 32

Lys Ser Ser Arg Ser Leu Leu Ala Ser Gly Asn Gln Asn Asn Tyr Leu
  1               5                  10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Synthetic CDR-L1 derived from L1-22 clone

<400> SEQUENCE: 33

Lys Ser Ser His Ser Leu Leu Ala Ser Gly Asn Gln Asn Asn Tyr Leu
  1               5                  10                  15

Ala

<210> SEQ ID NO 34
<211> LENGTH: 7
<212> TYPE: PRT
<213> ORGANISM: Artificial Sequence
<220> FEATURE:
<223> OTHER INFORMATION: Synthetic CDR-L2 derived from L2-9 clone

<400> SEQUENCE: 34

Trp Ala Ser Lys Arg Val Ser
  1               5

<210> SEQ ID NO 35
<211> LENGTH: 7
<212> TYPE: PRT
<213> ORGANISM: Artificial Sequence
<220> FEATURE:
<223> OTHER INFORMATION: Synthetic CDR-L2 derived from L2-12 clone

<400> SEQUENCE: 35

Trp Gly Ser Thr Arg Val Ser
  1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic CDR-L2 derived from L2-16 clone

<400> SEQUENCE: 36

Trp Gly Ser Thr Arg Val Pro
```

<210> SEQ ID NO 37
<211> LENGTH: 9
<212> TYPE: PRT
<213> ORGANISM: Artificial Sequence
<220> FEATURE:
<223> OTHER INFORMATION: Synthetic CDR-L3 derived from L3-32 clone

<400> SEQUENCE: 37

Gln Gln Ser Tyr Ser Lys Pro Phe Thr
 1               5

<210> SEQ ID NO 38
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      chAbF46
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 38
gaattcgccg ccaccatgga atggagctgg gttttctcg taacactttt aaatggtatc     60
cagtgtgagg tgaagctggt ggagtctgga ggaggcttgg tacagcctgg gggttctctg    120
agactctcct gtgcaactTc tgggttcacc ttcactgatt actacatgag ctgggtccgc    180
cagcctccag aaaggcact tgagtggttg ggttttatta aaacaaagc taatggttac    240 acaacagagt acagtgcatc tgtgaagggt cggttcacca tctccagaga taattcccaa    300
agcatcctct atcttcaaat ggacaccctg agagctgagg acagtgccac ttattactgt    360
gcaagagata actggtttgc ttactgggc aagggactc tggtcactgt ctctgcagct    420
agcaccaagg gcccatcggt cttccccctg gcaccctcct ccaagagcac ctctggggc    480 acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780

```
tcagtcttcc tcttcccccc aaaacccaag dacaccctca tgatctcccg daccoctgag      840 gtcacatgcg tggtggtgga cgtgagccac gaagaccctg aggtcaagtt caactggtac      900
gtggacggcg tggaggtgca taatgccaag acaaagccgc gggaggagca gtacaacagc      960
acgtaccgtg tggtcagcgt cctcaccgtc ctgcaccagg actggctgaa tggcaaggag     1020
tacaagtgca aggtctccaa caaagccctc ccagccccca tcgagaaaac catctccaaa     1080
gccaaagggc agccccgaga accacaggtg tacaccctgc ccccatcccg ggaggagatg     1140
accaagaacc aggtcagcct gacctgcctg gtcaaaggct tctatcccag cgacatcgcc     1200
gtggagtggg agagcaatgg gcagccggag aacaactaca agaccacgcc tcccgtgctg     1260
gactccgacg gctccttctt cctctacagc aagctcaccg tggacaagag caggtggcag     1320
caggggaacg tcttctcatg ctccgtgatg catgaggctc tgcacaacca ctacacgcag     1380
aagagcctct ccctgtctcc gggtaaatga ctcgag                               1416

<210> SEQ ID NO 39
<211> LENGTH: 759
<212> TYPE: DNA
<213> ORGANISM: Artificial Sequence
<220> FEATURE:
<223> OTHER INFORMATION: Synthetic nucleotide sequence of light chain of
      chAbF46
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 39
gaattcacta gtgattaatt cgccgccacc atgattcac aggcccaggt cctcatgttg        60
ctgctgctat cggtatctgg tacctgtgga gacattttga tgacccagtc tccatcctcc      120
ctgactgtgt cagcaggaga gaaggtcact atgagctgca gtccagtca gagtcttta       180 gctagtggca accaaaataa ctacttggcc tggcaccagc agaaaccagg acgatctcct      240
aaaatgctga atttggggc atccactagg gtatctggag tccctgatcg cttcataggc      300
agtggatctg ggacggattt cactctgacc atcaacagtg tgcaggctga agatctggct      360
gtttattact gtcagcagtc ctacagcgct ccgctcacgt tcggtgctgg gaccaagctg      420
gagctgaaac gtacggtggc tgcaccatct gtcttcatct tcccgccatc tgatgagcag      480
ttgaaatctg gaactgcctc tgttgtgtgc ctgctgaata acttctatcc cagagaggcc      540
```

```
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga acacaaagt ctacgcctgc gaagtcaccc atcagggcct gagctcgccc    720
gtcacaaaga gcttcaacag gggagagtgt tgactcgag                          759
```

```
<210> SEQ ID NO 40
<211> LENGTH: 447
<212> TYPE: PRT
<213> ORGANISM: Artificial Sequence
<220> FEATURE:
<223> OTHER INFORMATION: Synthetic amino acid sequence of H1-heavy

<400> SEQUENCE: 40

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 41
<211> LENGTH: 447
<212> TYPE: PRT
<213> ORGANISM: Artificial Sequence
<220> FEATURE:
<223> OTHER INFORMATION: Synthetic amino acid sequence of H3-heavy

<400> SEQUENCE: 41

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Arg Ala Glu Asp Thr Ala Val Tyr
                 85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 42
<211> LENGTH: 447
<212> TYPE: PRT
<213> ORGANISM: Artificial Sequence
<220> FEATURE:
<223> OTHER INFORMATION: Synthetic amino acid sequence of H4-heavy

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

-continued

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 43
<211> LENGTH: 220
<212> TYPE: PRT
<213> ORGANISM: Artificial Sequence
<220> FEATURE:
<223> OTHER INFORMATION: Synthetic amino acid sequence of H1-light

<400> SEQUENCE: 43

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 44
<211> LENGTH: 220
<212> TYPE: PRT
<213> ORGANISM: Artificial Sequence
<220> FEATURE:
<223> OTHER INFORMATION: Synthetic amino acid sequence of H2-light

<400> SEQUENCE: 44

Asp Ile Val Met Thr Gln Thr Pro Leu Ser Leu Pro Val Thr Pro Gly
  1               5                  10                  15

Glu Pro Ala Ser Ile Ser Cys Lys Ser Ser Gln Ser Leu Leu Ala Ser
             20                  25                  30

Gly Asn Gln Asn Asn Tyr Leu Ala Trp His Leu Gln Lys Pro Gly Gln
         35                  40                  45

Ser Pro Gln Met Leu Ile Ile Trp Ala Ser Thr Arg Val Ser Gly Val
     50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Ser Tyr Ser Ala Pro Leu Thr Phe Gly Gln Gly Thr Lys Leu Glu Leu
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220
```

<210> SEQ ID NO 45
<211> LENGTH: 220
<212> TYPE: PRT
<213> ORGANISM: Artificial Sequence
<220> FEATURE:
<223> OTHER INFORMATION: Synthetic amino acid sequence of H3-light

<400> SEQUENCE: 45

```
Asp Ile Val Met Thr Gln Ser Pro Asp Ser Leu Ala Val Ser Leu Gly
 1               5                  10                  15

Glu Arg Ala Thr Ile Asn Cys Lys Ser Gln Ser Leu Leu Ala Ser
            20                  25                  30

Gly Asn Gln Asn Asn Tyr Leu Ala Trp Tyr Gln Lys Pro Gly Gln
        35                  40                  45

Pro Pro Lys Leu Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
               100                 105                 110

Lys Arg Thr Val Ala Ala Pro Ser Val Phe Ile Phe Pro Pro Ser Asp
           115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 46
<211> LENGTH: 219
<212> TYPE: PRT
<213> ORGANISM: Artificial Sequence
<220> FEATURE:
<223> OTHER INFORMATION: Synthetic amino acid sequence of H4-light

<400> SEQUENCE: 46

```
Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95
```

```
Ser Tyr Ser Ala Pro Leu Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu
    210                 215

<210> SEQ ID NO 47
<211> LENGTH: 1350
<212> TYPE: DNA
<213> ORGANISM: Artificial Sequence
<220> FEATURE:
<223> OTHER INFORMATION: Synthetic nucleotide sequence of H1-heavy

<400> SEQUENCE: 47
gaggtgcagc tggtggagtc tgggggaggc ttggtccagc ctggagggtc cctgagactc     60
tcctgtgcag cctctggatt caccttcact gactactaca tgagctgggt ccgccaggct    120
ccagggaagg gctggagtg gttgggcttt attagaaaca agctaacgg ttacaccaca      180 gaatacagtg cgtctgtgaa aggcagattc accatctcaa gagataattc aaagaactca    240
ctgtatctgc aaatgaacag cctgaaaacc gaggacacgg ccgtgtatta ctgtgctaga    300
gataactggt ttgcttactg gggtcaagga accctggtca ccgtctcctc ggctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
ggcagccccc gagaaccaca ggtgtacacc ctgcccccat cccgggagga tgaccaag     1080 aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
```

```
ctctccctgt ctccgggtaa atgactcgag                               1350
```

<210> SEQ ID NO 48
<211> LENGTH: 1350
<212> TYPE: DNA
<213> ORGANISM: Artificial Sequence
<220> FEATURE:
<223> OTHER INFORMATION: Synthetic nucleotide sequence of H3-heavy

<400> SEQUENCE: 48

```
gaggtgcagc tggtggagtc tgggggaggc ttggtccagc ctggagggtc cctgagactc    60
tcctgtgcag cctctggatt caccttcact gactactaca tgagctgggt ccgccaggct   120
ccagggaagg ggctggagtg gttgggcttt attagaaaca agctaacgg ttacaccaca    180
gaatacagtg cgtctgtgaa aggcagattc accatctcaa gagataattc aaagaactca   240
ctgtatctgc aaatgaacag cctgcgtgct gaggacacgg ccgtgtatta ctgtgctaga   300
gataactggt ttgcttactg gggtcaagga accctggtca ccgtctcctc ggctagcacc   360
aagggcccat cggtcttccc cctggcaccc tcctccaaga gcacctctgg gggcacagcg   420
gccctgggct gcctggtcaa ggactacttc cccgaaccgg tgacggtgtc gtggaactca   480
ggcgccctga ccagcggcgt gcacaccttc ccggctgtcc tacagtcctc aggactctac   540
tccctcagca gcgtggtgac cgtgccctcc agcagcttgg gcacccagac ctacatctgc   600
aacgtgaatc acaagcccag caacaccaag gtggacaaga agttgagcc caaatcttgt   660
gacaaaactc acacatgccc accgtgccca gcacctgaac tcctggggg accgtcagtc   720
ttcctcttcc cccaaaaacc caaggacacc ctcatgatct cccggacccc tgaggtcaca   780
tgcgtggtgg tggacgtgag ccacgaagac cctgaggtca agttcaactg gtacgtggac   840
ggcgtggagg tgcataatgc caagacaaag ccgcgggagg agcagtacaa cagcacgtac   900
cgtgtggtca gcgtcctcac cgtcctgcac caggactggc tgaatggcaa ggagtacaag   960
tgcaaggtct ccaacaaagc cctcccagcc cccatcgaga aaaccatctc caaagccaaa  1020
gggcagcccc gagaaccaca ggtgtacacc ctgcccccat cccgggagga gatgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta cagcaagctc accgtggaca agagcaggtg gcagcagggg  1260
aacgtcttct catgctccgt gatgcatgag gctctgcaca accactacac gcagaagagc  1320
ctctccctgt ctccgggtaa atgactcgag                                   1350
```

<210> SEQ ID NO 49
<211> LENGTH: 1350
<212> TYPE: DNA
<213> ORGANISM: Artificial Sequence
<220> FEATURE:
<223> OTHER INFORMATION: Synthetic nucleotide sequence of H4-heavy

<400> SEQUENCE: 49

```
gaggttcagc tggtggagtc tggcggtggc ctggtgcagc caggggggctc actccgtttg    60
tcctgtgcag cttctggctt caccttcact gattactaca tgagctgggt gcgtcaggcc   120
ccgggtaagg gcctggaatg gttgggtttt attagaaaca agctaatgg ttacacaaca    180
gagtacagtg catctgtgaa gggtcgtttc actataagca gagataattc caaaacaca    240
ctgtacctgc agatgaacag cctgcgtgct gaggacactg ccgtctatta ttgtgctaga   300
gataactggt ttgcttactg gggccaaggg actctggtca ccgtctcctc ggctagcacc   360
```

```
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt     660 gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa   1020
gggcagcccc gagaaccaca ggtgtacacc ctgcccccat cccgggagga gatgaccaag   1080
aaccaggtca gcctgacctg cctggtcaaa ggcttctatc ccagcgacat cgccgtggag   1140
tgggagagca atgggcagcc ggagaacaac tacaagacca cgcctcccgt gctggactcc   1200
gacggctcct tcttcctcta cagcaagctc accgtggaca agagcaggtg gcagcagggg   1260
aacgtcttct catgctccgt gatgcatgag gctctgcaca accactacac gcagaagagc   1320
ctctccctgt ctccgggtaa atgactcgag                                    1350

<210> SEQ ID NO 50
<211> LENGTH: 669
<212> TYPE: DNA
<213> ORGANISM: Artificial Sequence
<220> FEATURE:
<223> OTHER INFORMATION: Synthetic nucleotide sequence of H1-light

<400> SEQUENCE: 50
gacatcgtga tgacccagtc tccagactcc ctggctgtgt ctctgggcga gagggccacc     60
atcaactgca gtccagcca gagtcttta gctagcggca accaaaataa ctacttagct      120
tggcaccagc agaaaccagg acagcctcct aagatgctca tatttgggc atctacccgg     180 gtatccgggg tccctgaccg attcagtggc agcgggtctg ggacagattt cactctcacc    240
atcagcagcc tgcaggctga agatgtgca gtttattact gtcagcaatc ctatagtgct    300
cctctcacgt tcggaggcgg taccaaggtg gagatcaaac gtacggtggc tgcaccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga acacaaagt ctacgcctgc    600 gaagtcaccc atcagggcct gagctcgccc gtcacaaaga gcttcaacag gggagagtgt    660
tgactcgag                                                            669

<210> SEQ ID NO 51
<211> LENGTH: 669
<212> TYPE: DNA
<213> ORGANISM: Artificial Sequence
<220> FEATURE:
<223> OTHER INFORMATION: Synthetic nucleotide sequence of H2-light

<400> SEQUENCE: 51
```

```
gatattgtga tgacccagac tccactctcc ctgcccgtca cccctggaga gccggcctcc      60
atctcctgca agtccagtca gagtctttta gctagtggca accaaaataa ctacttggcc     120
tggcacctgc agaagccagg gcagtctcca cagatgctga tcatttgggc atccactagg     180
gtatctggag tcccagacag gttcagtggc agtgggtcag gcactgattt cacactgaaa     240
atcagcaggg tggaggctga ggatgttgga gtttattact gccagcagtc ctacagcgct     300
ccgctcacgt tcggacaggg taccaagctg gagctcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669

<210> SEQ ID NO 52
<211> LENGTH: 669
<212> TYPE: DNA
<213> ORGANISM: Artificial Sequence
<220> FEATURE:
<223> OTHER INFORMATION: Synthetic nucleotide sequence of H3-light

<400> SEQUENCE: 52
gacatcgtga tgacccagtc tccagactcc ctggctgtgt ctctgggcga gagggccacc      60
atcaactgca gtccagcca gagtctttta gctagcggca accaaaataa ctacttagct     120
tggtaccagc agaaaccagg acagcctcct aagctgctca ttatttgggc atctacccgg     180
gtatccgggg tccctgaccg attcagtggc agcgggtctg ggacagattt cactctcacc     240
atcagcagcc tgcaggctga agatgtggca gtttattact gtcagcaatc ctatagtgct     300
cctctcacgt tcggaggcgg taccaaggtg gagatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660
tgactcgag                                                             669

<210> SEQ ID NO 53
<211> LENGTH: 669
<212> TYPE: DNA
<213> ORGANISM: Artificial Sequence
<220> FEATURE:
<223> OTHER INFORMATION: Synthetic nucleotide sequence of H4-light

<400> SEQUENCE: 53
gatatccaga tgacccagtc cccgagctcc ctgtccgcct ctgtgggcga tagggtcacc      60
atcacctgca gtccagtca gagtctttta gctagtggca accaaaataa ctacttggcc     120
tggcaccaac agaaaccagg aaaagctccg aaaatgctga ttatttgggc atccactagg     180
gtatctggag tcccttctcg cttctctgga tccgggtctg gacggatttt cactctgacc     240
atcagcagtc tgcagccgga agacttcgca acttattact gtcagcagtc ctacagcgct     300
ccgctcacgt tcggacaggg taccaaggtg gagatcaaac gtacggtggc tgcaccatct     360
```

```
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
tgactcgag                                                             669
```

<210> SEQ ID NO 54
<211> LENGTH: 23
<212> TYPE: PRT
<213> ORGANISM: Artificial Sequence
<220> FEATURE:
<223> OTHER INFORMATION: Synthetic linker between VH and VL

<400> SEQUENCE: 54

Gly Leu Gly Gly Leu Gly Gly Gly Ser Gly Gly Gly Ser Gly
 1               5                  10                  15

Gly Ser Ser Gly Val Gly Ser
            20

<210> SEQ ID NO 55
<211> LENGTH: 1088
<212> TYPE: DNA
<213> ORGANISM: Artificial Sequence
<220> FEATURE:
<223> OTHER INFORMATION: Synthetic polynucleotide encoding scFv of
      huAbF46 antibody

<400> SEQUENCE: 55

```
gctagcgttt tagcagaagt tcaattggtt gaatctggtg gtggtttggt tcaaccaggt     60
ggttctttga gattgtcttg tgctgcttct ggttttactt tcaccgatta ttacatgtcc    120
tgggttagac aagctccagg taaaggtttg gaatggttgg gtttcattag aaacaaggct    180
aacggttaca ctaccgaata ttctgcttct gttaagggta gattcaccat ttctagagac    240
aactctaaga cacccttgta cttgcaaatg aactccttga gagctgaaga tactgctgtt    300
tattactgcg ctagagataa ttggtttgct tattgggtc aaggtacttt ggttactgtt    360
tcttctggcc tcgggggcct cggaggagga ggtagtggcg gaggaggctc cggtggatcc    420
agcggtgtgg gttccgatat tcaaatgacc caatctccat cttctttgtc tgcttcagtt    480
ggtgatagag ttaccattac ttgtaagtcc tcccaatctt tgttggcttc tggtaatcag    540
aacaattact ggcttggca tcaacaaaaa ccaggtaaag ctccaaagat gttgattatt    600
tgggcttcta ccagagtttc tggtgttcca tctagatttt ctggttctgg ttccggtact    660
gattttactt tgaccatttc atccttgcaa ccagaagatt tcgctactta ctactgtcaa    720
caatcttact ctgctccatt gacttttggt caaggtacaa aggtcgaaat caagagagaa    780
ttcggtaagc ctatccctaa ccctctcctc ggtctcgatt ctacgggtgg tggtggatct    840
ggtggtggtg gttctggtgg tggtggttct caggaactga caactatatg cgagcaaatc    900
ccctcaccaa tttagaatc gacgccgtac tctttgtcaa cgactactat tttggccaac    960
gggaaggcaa tgcaaggagt ttttgaatat tacaaatcag taacgtttgt cagtaattgc   1020
ggttctcacc cctcaacaac tagcaaaggc agccccataa acacacagta tgttttttga   1080
gtttaaac                                                            1088
```

```
<210> SEQ ID NO 56
<211> LENGTH: 5597
<212> TYPE: DNA
<213> ORGANISM: Artificial Sequence
<220> FEATURE:
<223> OTHER INFORMATION: Synthetic expression vector including
      polynucleotide encoding scFv of huAbF46 antibody
<220> FEATURE:
<221> NAME/KEY: misc_difference
<222> LOCATION: (573)..(578)
<223> OTHER INFORMATION: NheI restriction site
<220> FEATURE:
<221> NAME/KEY: misc_difference
<222> LOCATION: (588)..(938)
<223> OTHER INFORMATION: huAbF46 VH
<220> FEATURE:
<221> NAME/KEY: misc_difference
<222> LOCATION: (939)..(1007)
<223> OTHER INFORMATION: linker
<220> FEATURE:
<221> NAME/KEY: misc_difference
<222> LOCATION: (1008)..(1349)
<223> OTHER INFORMATION: huAbF46 VL
<220> FEATURE:
<221> NAME/KEY: misc_difference
<222> LOCATION: (1350)..(1355)
<223> OTHER INFORMATION: EcoRI restriction site
<220> FEATURE:
<221> NAME/KEY: misc_difference
<222> LOCATION: (1356)..(1397)
<223> OTHER INFORMATION: V5 epitope
<220> FEATURE:
<221> NAME/KEY: misc_difference
<222> LOCATION: (1398)..(1442)
<223> OTHER INFORMATION: (G4S)3 linker
<220> FEATURE:
<221> NAME/KEY: misc_difference
<222> LOCATION: (1443)..(1649)
<223> OTHER INFORMATION: Aga2
<220> FEATURE:
<221> NAME/KEY: misc_difference
<222> LOCATION: (1650)..(1652)
<223> OTHER INFORMATION: TGA(stop codon)
<220> FEATURE:
<221> NAME/KEY: misc_difference
<222> LOCATION: (1653)..(1660)
<223> OTHER INFORMATION: PmeI restriction site

<400> SEQUENCE: 56
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg ttttttcaata tttttctgtta ttgctagcgt tttagcagaa gttcaattgg     600
ttgaatctgg tggtgttttg gttcaaccag gtggttcttt gagattgtct tgtgctgctt     660
ctggttttac tttcaccgat tattacatgt cctgggttag acaagctcca ggtaaaggtt     720
tggaatggtt gggtttcatt agaaacaagg ctaacggtta cactaccgaa tattctgctt     780
ctgttaaggg tagattcacc atttctagag acaactctaa gaacaccttg tacttgcaaa     840
tgaactcctt gagagctgaa gatactgctg tttattactg cgctagagat aattggtttg     900
```

```
cttattgggg tcaaggtact ttggttactg tttcttctgg cctcggggc ctcggaggag    960 gaggtagtgg cggaggaggc tccggtggat ccagcggtgt gggttccgat attcaaatga   1020
cccaatctcc atcttctttg tctgcttcag ttggtgatag agttaccatt acttgtaagt   1080
cctcccaatc tttgttggct tctggtaatc agaacaatta cttggcttgg catcaacaaa   1140
aaccaggtaa agctccaaag atgttgatta tttgggcttc taccagagtt tctggtgttc   1200
catctagatt ttctggttct ggttccggta ctgattttac tttgaccatt tcatccttgc   1260
aaccagaaga tttcgctact tactactgtc aacaatctta ctctgctcca ttgacttttg   1320
gtcaaggtac aaaggtcgaa atcaagagag aattcggtaa gcctatccct aaccctctcc   1380
tcggtctcga ttctacgggt ggtggtggat ctggtggtgg tggttctggt ggtggtggtt   1440
ctcaggaact gacaactata tgcgagcaaa tcccctcacc aactttagaa tcgacgccgt   1500
actctttgtc aacgactact attttggcca acgggaaggc aatgcaagga gttttttgaat   1560 attacaaatc agtaacgttt gtcagtaatt gcggttctca cccctcaaca actagcaaag   1620
gcagccccat aaacacacag tatgtttttt gagtttaaac ccgctgatct gataacaaca   1680
gtgtagatgt aacaaaatcg actttgttcc cactgtactt ttagctcgta caaaatacaa   1740 tatactttc atttctccgt aaacaacatg tttcccatg taatatcctt ttctattttt    1800
cgttccgtta ccaactttac acatacttta tatagctatt cacttctata cactaaaaaa   1860
ctaagacaat tttaattttg ctgcctgcca tatttcaatt tgttataaat tcctataatt   1920
tatcctatta gtagctaaaa aaagatgaat gtgaatcgaa tcctaagaga attgggcaag   1980
tgcacaaaca atacttaaat aaatactact cagtaataac ctatttctta gcattttga    2040 cgaaatttgc tattttgtta gagtctttta caccatttgt ctccacacct ccgcttacat   2100
caacaccaat aacgccattt aatctaagcg catcaccaac attttctggc gtcagtccac   2160
cagctaacat aaaatgtaag ctctcgggc tctcttgcct tccaacccag tcagaaatcg    2220
agttccaatc caaaagttca cctgtcccac ctgcttctga atcaaacaag ggaataaacg   2280
aatgaggttt ctgtgaagct gcactgagta gtatgttgca gtcttttgga aatacgagtc   2340
ttttaataac tggcaaaccg aggaactctt ggtattcttg ccacgactca tctccgtgca   2400
gttggacgat atcaatgccg taatcattga ccagagccaa acatcctcc ttaggttgat    2460 tacgaaacac gccaaccaag tatttcggag tgcctgaact attttttatat gcttttacaa   2520 gacttgaaat tttccttgca ataaccgggt caattgttct cttctcattg ggcacacata   2580
taatacccag caagtcagca tcggaatcta gagcacattc tgcggcctct gtgctctgca   2640
agccgcaaac tttcaccaat ggaccagaac tacctgtgaa attaataaca gacatactcc   2700
aagctgcctt tgtgtgctta atcacgtata ctcacgtgct caatagtcac caatgccctc   2760
cctcttggcc ctctccttt ctttttcga ccgaatttct tgaagacgaa agggcctcgt    2820
gatacgccta ttttataggt taatgtcat gataataatg tttcttagg acggatcgct    2880 tgcctgtaac ttacacgcgc ctcgtatctt ttaatgatgg ataatttggg aatttactc    2940 tgtgttatt tattttatg ttttgtattt ggatttaga agtaaataa agaaggtaga      3000 agagttacgg aatgaagaaa aaaaaataaa caaaggttta aaaatttca acaaaaagcg    3060 tactttacat atatatttat tagacaagaa aagcagatta aatagatata cattcgatta   3120
acgataagta aaatgtaaaa tcacaggatt ttcgtgtgtg gtcttctaca cagacaagat   3180
gaaacaattc ggcattaata cctgagagca ggaagagcaa gataaaaggt agtatttgtt   3240
```

-continued

```
ggcgatcccc ctagagtctt ttacatcttc ggaaaacaaa aactattttt tctttaattt      3300 cttttttac tttctatttt taatttatat atttatatta aaaaatttaa attataatta       3360
tttttatagc acgtgatgaa aaggacccag gtggcacttt tcggggaaat gtgcgcggaa     3420
cccctatttg tttattttc taaatacatt caaatatgta tccgctcatg agacaataac       3480
cctgataaat gcttcaataa tattgaaaaa ggaagagtat gagtattcaa catttccgtg     3540
tcgcccttat tcccttttt gcggcatttt gccttcctgt ttttgctcac ccagaaacgc      3600
tggtgaaagt aaaagatgct gaagatcagt tgggtgcacg agtgggttac atcgaactgg    3660
atctcaacag cggtaagatc cttgagagtt ttcgccccga gaacgtttt ccaatgatga     3720 gcacttttaa agttctgcta tgtggcgcgg tattatcccg tgttgacgcc gggcaagagc    3780
aactcggtcg ccgcatacac tattctcaga atgacttggt tgagtactca ccagtcacag    3840
aaaagcatct tacggatggc atgacagtaa gagaattatg cagtgctgcc ataaccatga    3900
gtgataacac tgcggccaac ttacttctga caacgatcgg aggaccgaag gagctaaccg   3960
cttttttgca acatgggg gatcatgtaa ctcgccttga tcgttgggaa ccggagctga      4020
atgaagccat accaaacgac gagcgtgaca ccacgatgcc tgtagcaatg gcaacaacgt    4080
tgcgcaaact attaactggc gaactactta ctctagcttc ccggcaacaa ttaatagact    4140
ggatggaggc ggataaagtt gcaggaccac ttctgcgctc ggcccttccg gctggctggt    4200
ttattgctga taaatctgga gccggtgagc gtgggtctcg cggtatcatt gcagcactgg    4260
ggccagatgg taagccctcc cgtatcgtag ttatctacac gacgggcagt caggcaacta    4320
tggatgaacg aaatagacag atcgctgaga taggtgcctc actgattaag cattggtaac    4380
tgtcagacca gtttactca tatatacttt agattgattt aaaacttcat ttttaattta     4440
aaaggatcta ggtgaagatc cttttttgata atctcatgac caaaatccct taacgtgagt   4500
tttcgttcca ctgagcgtca gaccccgtag aaaagatcaa aggatcttct tgagatcctt    4560
tttttctgcg cgtaatctgc tgcttgcaaa caaaaaaacc accgctacca gcggtggttt   4620
gtttgccgga tcaagagcta ccaactcttt ttccgaaggt aactggcttc agcagagcgc    4680
agataccaaa tactgtcctt ctagtgtagc cgtagttagg ccaccacttc aagaactctg    4740
tagcaccgcc tacatacctc gctctgctaa tcctgttacc agtggctgct gccagtggcg    4800
ataagtcgtg tcttaccggg ttggactcaa gacgatagtt accggataag gcgcagcggt    4860
cgggctgaac ggggggttcg tgcacacagc ccagcttgga gcgaacgacc tacaccgaac    4920
tgagatacct acagcgtgag cattgagaaa gcgccacgct tcccgaaggg agaaaggcgg    4980
acaggtatcc ggtaagcggc agggtcggaa caggagagcg cacgagggag cttccagggg   5040
ggaacgcctg gtatctttat agtcctgtcg ggtttcgcca cctctgactt gagcgtcgat     5100
ttttgtgatg ctcgtcaggg gggccgagcc tatggaaaaa cgccagcaac gcggcctttt    5160
tacggttcct ggccttttgc tggccttttg ctcacatgtt ctttcctgcg ttatcccctg    5220
attctgtgga taaccgtatt accgcctttg agtgagctga taccgctcgc cgcagccgaa    5280
cgaccgagcg cagcgagtca gtgagcgagg aagcggaaga gcgcccaata cgcaaaccgc    5340
ctctccccgc gcgttggccg attcattaat gcagctggca cgacaggttt cccgactgga    5400
aagcgggcag tgagcgcaac gcaattaatg tgagttacct cactcattag gcaccccagg    5460
ctttacactt tatgcttccg gctcctatgt tgtgtggaat tgtgagcgga taacaatttc    5520
acacaggaaa cagctatgac catgattacg ccaagctcgg aattaaccct cactaaaggg    5580
aacaaaagct ggctagt                                                    5597
```

<210> SEQ ID NO 57
<211> LENGTH: 13
<212> TYPE: PRT
<213> ORGANISM: Artificial Sequence
<220> FEATURE:
<223> OTHER INFORMATION: Synthetic U6-HC7 hinge

<400> SEQUENCE: 57

Glu Pro Lys Ser Cys Asp Cys His Cys Pro Pro Cys Pro
 1               5                  10

<210> SEQ ID NO 58
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-1 clone

<400> SEQUENCE: 58
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtcagcagtc ctacagccgc ccgtacacgt tcggacaggg taccaaggtg     420
gagatcaaac gtacg                                                     435

<210> SEQ ID NO 59
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-2 clone

<400> SEQUENCE: 59
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg ggacggattt cactctgacc atcagcagtc tgcagccgga agacttcgca     360
acttattact gtgggcagtc ctacagccgt ccgctcacgt tcggacaggg taccaaggtg     420
gagatcaaac gtacg                                                     435

<210> SEQ ID NO 60
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-3 clone

<400> SEQUENCE: 60

```
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg gacggattt cactctgacc atcagcagtc tgcagccgga agacttcgca     360
acttattact gtgcacagtc ctacagccat ccgttctctt tcggacaggg taccaaggtg     420
gagatcaaac gtacg                                                     435

<210> SEQ ID NO 61
<211> LENGTH: 435
<212> TYPE: DNA
<213> ORGANISM: Artificial Sequence
<220> FEATURE:
<223> OTHER INFORMATION: Synthetic polynucleotide encoding CDR-L3
      derived from L3-5 clone

<400> SEQUENCE: 61
gaattcacta gtgattaatt cgccgccacc atggattcac aggcccaggt cctcatgttg      60
ctgctgctat cggtatctgg tacctgtgga gatatccaga tgacccagtc cccgagctcc     120
ctgtccgcct ctgtgggcga tagggtcacc atcacctgca agtccagtca gagtctttta     180
gctagtggca accaaaataa ctacttggcc tggcaccaac agaaaccagg aaaagctccg     240
aaaatgctga ttatttgggc atccactagg gtatctggag tcccttctcg cttctctgga     300
tccgggtctg gacggattt cactctgacc atcagcagtc tgcagccgga agacttcgca     360
acttattact gtgcagcagtc ctacagccgc ccgtttacgt tcggacaggg taccaaggtg     420
gagatcaaac gtacg                                                     435

<210> SEQ ID NO 62
<211> LENGTH: 462
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, U6-HC7 hinge and constant region of
      human IgG1

<400> SEQUENCE: 62

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Asn Trp Phe Ala Tyr Trp Gly Gln Gly Thr
            115                 120                 125
```

```
Leu Val Thr Val Ser Ser Ala Ser Thr Lys Gly Pro Ser Val Phe Pro
    130                 135                 140
Leu Ala Pro Ser Ser Lys Ser Thr Ser Gly Gly Thr Ala Ala Leu Gly
145                 150                 155                 160
Cys Leu Val Lys Asp Tyr Phe Pro Glu Pro Val Thr Val Ser Trp Asn
                165                 170                 175
Ser Gly Ala Leu Thr Ser Gly Val His Thr Phe Pro Ala Val Leu Gln
            180                 185                 190
Ser Ser Gly Leu Tyr Ser Leu Ser Ser Val Val Thr Val Pro Ser Ser
        195                 200                 205
Ser Leu Gly Thr Gln Thr Tyr Ile Cys Asn Val Asn His Lys Pro Ser
    210                 215                 220
Asn Thr Lys Val Asp Lys Lys Val Glu Pro Lys Ser Cys Asp Cys His
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Ala Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
    370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Val Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
    450                 455                 460

<210> SEQ ID NO 63
<211> LENGTH: 1410
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, U6-HC7 hinge and
      constant region of human IgG1

<400> SEQUENCE: 63
gaattcgccg ccaccatgga atggagctgg gttttcctcg taacactttt aaatggtatc      60
cagtgtgagg ttcagctggt ggagtctggc ggtggcctgg tgcagccagg gggctcactc    120
```

```
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
agctgcgatt gccactgtcc tccatgtcca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga gatgaccaag   1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg   1320 aacgtcttct catgctccgt gatgcatgag gctctgcaca accactacac gcagaagagc   1380
ctctccctgt ctccgggtaa atgactcgag                                     1410
```

<210> SEQ ID NO 64
<211> LENGTH: 461
<212> TYPE: PRT
<213> ORGANISM: Artificial Sequence
<220> FEATURE:
<223> OTHER INFORMATION: Synthetic polypeptide consisting of heavy chain of huAbF46-H4-A1, human IgG2 hinge and constant region of human IgG1

<400> SEQUENCE: 64

```
Met Glu Trp Ser Trp Val Phe Leu Val Thr Leu Leu Asn Gly Ile Gln
 1               5                  10                  15

Cys Glu Val Gln Leu Val Glu Ser Gly Gly Gly Leu Val Gln Pro Gly
             20                  25                  30

Gly Ser Leu Arg Leu Ser Cys Ala Ala Ser Gly Phe Thr Phe Thr Asp
         35                  40                  45

Tyr Tyr Met Ser Trp Val Arg Gln Ala Pro Gly Lys Gly Leu Glu Trp
     50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr
        115                 120                 125
```

Leu Val Thr Val Ser Ser Ala Ser Thr Lys Gly Pro Ser Val Phe Pro
            130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
210                 215                 220

Asn Thr Lys Val Asp Lys Lys Val Glu Arg Lys Cys Cys Val Glu Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
450                 455                 460

<210> SEQ ID NO 65
<211> LENGTH: 1407
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG1

<400> SEQUENCE: 65
gaattcgccg ccaccatgga atggagctgg gttttctctg taacactttt aaatggtatc    60
cagtgtgagg ttcagctggt ggagtctggc ggtggcctgg tgcagccagg ggctcactc   120

```
cgtttgtcct gtgcagcttc tggcttcacc ttcactgatt actacatgag ctgggtgcgt    180
caggccccgg gtaagggcct ggaatggttg ggttttatta gaaacaaagc taatggttac    240
acaacagagt acagtgcatc tgtgaagggt cgtttcacta taagcagaga taattccaaa    300
aacacactgt acctgcagat gaacagcctg cgtgctgagg acactgccgt ctattattgt    360
gctagagata actggtttgc ttactggggc caagggactc tggtcaccgt ctcctcggct    420
agcaccaagg gcccatcggt cttccccctg cacctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagaggaag    720
tgctgtgtgg agtgcccccc ctgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc ctcccgtgct ggactccgac   1260
ggctccttct cctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg actcgag                                      1407
```

<210> SEQ ID NO 66
<211> LENGTH: 460
<212> TYPE: PRT
<213> ORGANISM: Artificial Sequence
<220> FEATURE:
<223> OTHER INFORMATION: Synthetic polypeptide consisting of heavy chain
      of huAbF46-H4-A1, human IgG2 hinge and constant region of
      human IgG2

<400> SEQUENCE: 66

Met Glu Trp Ser Trp Val Phe Leu Val Thr Leu Leu Asn Gly Ile Gln
  1               5                  10                  15

Cys Glu Val Gln Leu Val Glu Ser Gly Gly Gly Leu Val Gln Pro Gly
                 20                  25                  30

Gly Ser Leu Arg Leu Ser Cys Ala Ala Ser Gly Phe Thr Phe Thr Asp
             35                  40                  45

Tyr Tyr Met Ser Trp Val Arg Gln Ala Pro Gly Lys Gly Leu Glu Trp
         50                  55                  60

Leu Gly Phe Ile Arg Asn Lys Ala Asn Gly Tyr Thr Thr Glu Tyr Ser
 65                  70                  75                  80

Ala Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
            100                 105                 110

Tyr Tyr Cys Ala Arg Asp Asn Trp Phe Ala Tyr Trp Gly Gln Gly Thr

```
            115                 120                 125
Leu Val Thr Val Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Asn Phe Gly Thr Gln Thr Tyr Thr Cys Asn Val Asp His Lys Pro Ser
    210                 215                 220

Asn Thr Lys Val Asp Lys Thr Val Glu Arg Lys Cys Cys Val Glu Cys
225                 230                 235                 240

Pro Pro Cys Pro Ala Pro Pro Val Ala Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Gln Phe
            275                 280                 285

Asn Trp Tyr Val Asp Gly Val Glu Val His Asn Ala Lys Thr Lys Pro
        290                 295                 300

Arg Glu Glu Gln Phe Asn Ser Thr Phe Arg Val Val Ser Val Leu Thr
305                 310                 315                 320

Val Val His Gln Asp Trp Leu Asn Gly Lys Glu Tyr Lys Cys Lys Val
                325                 330                 335

Ser Asn Lys Gly Leu Pro Ala Pro Ile Glu Lys Thr Ile Ser Lys Thr
            340                 345                 350

Lys Gly Gln Pro Arg Glu Pro Gln Val Tyr Thr Leu Pro Pro Ser Arg
        355                 360                 365

Glu Glu Met Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Met Leu Asp Ser Asp Gly Ser
                405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
        435                 440                 445

Tyr Thr Gln Lys Ser Leu Ser Leu Ser Pro Gly Lys
    450                 455                 460
```

<210> SEQ ID NO 67
<211> LENGTH: 1404
<212> TYPE: DNA
<213> ORGANISM: Artificial Sequence
<220> FEATURE:
<223> OTHER INFORMATION: Synthetic polynucleotide encoding polypeptide
      consisting of heavy chain of huAbF46-H4-A1, human IgG2 hinge and
      constant region of human IgG2

<400> SEQUENCE: 67
gaattcgccg ccaccatgga atggagctgg gttttctcg taacactttt aaatggtatc    60

```
cagtgtgagg ttcagctggt ggagtctggc ggtggcctgg tgcagccagg gggctcactc      120
cgtttgtcct gtgcagcttc tggcttcacc ttcactgatt actacatgag ctgggtgcgt      180
caggccccgg gtaagggcct ggaatggttg ggttttatta gaaacaaagc taatggttac      240
acaacagagt acagtgcatc tgtgaagggt cgtttcacta taagcagaga taattccaaa      300
aacacactgt acctgcagat gaacagcctg cgtgctgagg acactgccgt ctattattgt      360
gctagagata actggtttgc ttactggggc caagggactc tggtcaccgt ctcctcggct      420
agcaccaagg gcccatcggt cttccccctg gcgccctgct ccaggagcac ctccgagagc      480
acagcggccc tgggctgcct ggtcaaggac tacttccccg aaccggtgac ggtgtcgtgg      540
aactcaggcg ctctgaccag cggcgtgcac accttcccag ctgtcctaca gtcctcagga      600
ctctactccc tcagcagcgt ggtgaccgtg ccctccagca acttcggcac ccagacctac      660
acctgcaacg tagatcacaa gcccagcaac accaaggtgg acaagacagt tgagcgcaaa      720
tgttgtgtcg agtgcccacc gtgcccagca ccacctgtgg caggaccgtc agtcttcctc      780
ttccccccaa aacccaagga caccctcatg atctcccgga cccctgaggt cacgtgcgtg      840
gtggtggacg tgagccacga agaccccgag gtccagttca actggtacgt ggacggcgtg      900
gaggtgcata atgccaagac aaagccacgg gaggagcagt tcaacagcac gttccgtgtg      960
gtcagcgtcc tcaccgttgt gcaccaggac tggctgaacg gcaaggagta caagtgcaag     1020
gtctccaaca aaggcctccc agcccccatc gagaaaacca tctccaaaac caagggcag     1080
ccccgagaac acaggtgta caccctgccc ccatcccggg aggagatgac caagaaccag     1140
gtcagcctga cctgcctggt caaaggcttc taccccagcg acatcgccgt ggagtgggag     1200
agcaatgggc agccggagaa caactacaag accacgcctc ccatgctgga ctccgacggc     1260
tccttcttcc tctacagcaa gctcaccgtg gacaagagca ggtggcagca ggggaacgtc     1320
ttctcatgct ccgtgatgca tgaggctctg cacaaccact acacgcagaa gagcctctcc     1380
ctgtctccgg gtaaatgact cgag                                            1404
```

<210> SEQ ID NO 68
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1(H36Y) and human kappa constant region

<400> SEQUENCE: 68

```
Met Asp Ser Gln Ala Gln Val Leu Met Leu Leu Leu Leu Ser Val Ser
  1               5                  10                  15

Gly Thr Cys Gly Asp Ile Gln Met Thr Gln Ser Pro Ser Ser Leu Ser
             20                  25                  30

Ala Ser Val Gly Asp Arg Val Thr Ile Thr Cys Lys Ser Ser Gln Ser
         35                  40                  45

Leu Leu Ala Ser Gly Asn Gln Asn Asn Tyr Leu Ala Trp Tyr Gln Gln
     50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Ser Gly Thr Asp
                 85                  90                  95

Phe Thr Leu Thr Ile Ser Ser Leu Gln Pro Glu Asp Phe Ala Thr Tyr
            100                 105                 110

Tyr Cys Gln Gln Ser Tyr Ser Arg Pro Tyr Thr Phe Gly Gln Gly Thr
```

```
                115                 120                 125
Lys Val Glu Ile Lys Arg Thr Val Ala Ala Pro Ser Val Phe Ile Phe
        130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 69
<211> LENGTH: 758
<212> TYPE: DNA
<213> ORGANISM: Artificial Sequence
<220> FEATURE:
<223> OTHER INFORMATION: Synthetic polynucleotide encoding polypeptide
      consisting of light chain of huAbF46-H4-A1(H36Y) and human kappa
      constant region

<400> SEQUENCE: 69
aattcactag tgattaattc gccgccacca tggattcaca ggcccaggtc ctcatgttgc      60
tgctgctatc ggtatctggt acctgtggag atatccagat gacccagtcc ccgagctccc     120
tgtccgcctc tgtgggcgat agggtcacca tcacctgcaa gtccagtcag agtcttttag     180
ctagtggcaa ccaaaataac tacttggcct ggtaccaaca gaaaccagga aaagctccga     240
aaatgctgat tatttgggca tccactaggg tatctgagt ccttctcgc ttctctggat       300 ccgggtctgg gacggatttc actctgacca tcagcagtct gcagccggaa gacttcgcaa     360
cttattactg tcagcagtcc tacagccgcc gtacacgtt cggacagggt accaaggtgg      420
agatcaaacg tacggtggct gcaccatctg tcttcatctt cccgccatct gatgagcagt     480
tgaaatctgg aactgcctct gttgtgtgcc tgctgaataa cttctatccc agagaggcca     540
aagtacagtg gaaggtggat aacgcccccc aatcgggtaa ctcccaggag agtgtcacag     600
agcaggacag caaggacagc acctacagcc tcagcagcac cctgacgctg agcaaagcag     660
actacgagaa acacaaagtc tacgcctgcg aagtcaccca tcagggcctg agctcgcccg     720
tcacaaagag cttcaacagg ggagagtgtt gactcgag                             758

<210> SEQ ID NO 70
<211> LENGTH: 240
<212> TYPE: PRT
<213> ORGANISM: Artificial Sequence
<220> FEATURE:
<223> OTHER INFORMATION: Synthetic polypeptide consisting of light chain
      of huAbF46-H4-A1 and human kappa constant region

<400> SEQUENCE: 70

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
            20                  25                  30

Ala Ser Val Gly Asp Arg Val Thr Ile Thr Cys Lys Ser Ser Gln Ser
```

```
                35                  40                  45
Leu Leu Ala Ser Gly Asn Gln Asn Asn Tyr Leu Ala Trp His Gln Gln
         50                  55                  60

Lys Pro Gly Lys Ala Pro Lys Met Leu Ile Ile Trp Ala Ser Thr Arg
 65                  70                  75                  80

Val Ser Gly Val Pro Ser Arg Phe Ser Gly Ser Gly Thr Asp
                 85                  90                  95

Phe Thr Leu Thr Ile Ser Ser Leu Gln Pro Glu Asp Phe Ala Thr Tyr
             100                 105                 110

Tyr Cys Gln Gln Ser Tyr Ser Arg Pro Tyr Thr Phe Gly Gln Gly Thr
             115                 120                 125

Lys Val Glu Ile Lys Arg Thr Val Ala Ala Pro Ser Val Phe Ile Phe
         130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240

<210> SEQ ID NO 71
<211> LENGTH: 19
<212> TYPE: PRT
<213> ORGANISM: Artificial Sequence
<220> FEATURE:
<223> OTHER INFORMATION: Synthetic epitope in SEMA domain of c-Met

<400> SEQUENCE: 71

Phe Ser Pro Gln Ile Glu Glu Pro Ser Gln Cys Pro Asp Cys Val Val
 1               5                  10                  15

Ser Ala Leu

<210> SEQ ID NO 72
<211> LENGTH: 10
<212> TYPE: PRT
<213> ORGANISM: Artificial Sequence
<220> FEATURE:
<223> OTHER INFORMATION: Synthetic epitope in SEMA domain of c-Met

<400> SEQUENCE: 72

Pro Gln Ile Glu Glu Pro Ser Gln Cys Pro
 1               5                  10

<210> SEQ ID NO 73
<211> LENGTH: 5
<212> TYPE: PRT
<213> ORGANISM: Artificial Sequence
<220> FEATURE:
<223> OTHER INFORMATION: Synthetic epitope in SEMA domain of c-Met

<400> SEQUENCE: 73

Glu Glu Pro Ser Gln
 1               5
```

<210> SEQ ID NO 74
<211> LENGTH: 117
<212> TYPE: PRT
<213> ORGANISM: Artificial Sequence
<220> FEATURE:
<223> OTHER INFORMATION: Synthetic heavy chain variable region of
      anti-c-Met antibody (AbF46 or huAbF46-H1)

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 75
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody (AbF46 or huAbF46-H1)

<400> SEQUENCE: 75

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Leu Leu Ala Ser
            20                  25                  30

Gly Asn Gln Asn Asn Tyr Leu Ala Trp His Gln Gln Lys Pro Gly Gln
        35                  40                  45

Pro Pro Lys Met Leu Ile Ile Trp Ala Ser Thr Arg Val Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gly Gly Thr Lys Val Glu Ile
            100                 105                 110

Lys Arg

<210> SEQ ID NO 76
<211> LENGTH: 1416
<212> TYPE: DNA
<213> ORGANISM: Artificial Sequence
<220> FEATURE:
<223> OTHER INFORMATION: Synthetic nucleotide sequence of heavy chain of
      anti-c-Met antibody (AbF46 or huAbF46-H1)
<220> FEATURE:
<221> NAME/KEY: misc_feature

```
<222> LOCATION: (1)..(6)
<223> OTHER INFORMATION: EcoRI restriction site
<220> FEATURE:
<221> NAME/KEY: misc_feature
<222> LOCATION: (7)..(66)
<223> OTHER INFORMATION: signal sequence
<220> FEATURE:
<221> NAME/KEY: misc_feature
<222> LOCATION: (67)..(417)
<223> OTHER INFORMATION: VH - heavy chain variable region
<220> FEATURE:
<221> NAME/KEY: misc_feature
<222> LOCATION: (418)..(423)
<223> OTHER INFORMATION: NdeI restriction site
<220> FEATURE:
<221> NAME/KEY: misc_feature
<222> LOCATION: (418)..(1407)
<223> OTHER INFORMATION: CH - heavy chain constant region
<220> FEATURE:
<221> NAME/KEY: misc_feature
<222> LOCATION: (1408)..(1410)
<223> OTHER INFORMATION: TGA - stop codon
<220> FEATURE:
<221> NAME/KEY: misc_feature
<222> LOCATION: (1411)..(1416)
<223> OTHER INFORMATION: XhoI restriction site

<400> SEQUENCE: 76
gaattcgccg ccaccatgga atggagctgg gttttctcg taacactttt aaatggtatc      60
cagtgtgagg tgaagctggt ggagtctgga ggaggcttgg tacagcctgg gggttctctg     120
agactctcct gtgcaacttc tgggttcacc ttcactgatt actacatgag ctgggtccgc     180
cagcctccag aaaggcact tgagtggttg ggttttatta aaacaaagc taatggttac       240 acaacagagt acagtgcatc tgtgaagggt cggttcacca tctccagaga taattcccaa     300
agcatcctct atcttcaaat ggcaccctg agagctgagg acagtgccac ttattactgt      360
gcaagagata actggtttgc ttactgggc aagggactc tggtcactgt ctctgcagct      420
agcaccaagg gcccatcggt cttccccctg gcaccctcct ccaagagcac ctctgggggc    480
acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagaaagt tgagcccaaa    720
tcttgtgaca aaactcacac atgcccaccg tgcccagcac ctgaactcct ggggggaccg    780
tcagtcttcc tcttcccccc aaaacccaag gacaccctca tgatctcccg gacccctgag    840
gtcacatgcg tggtggtgga cgtgagccac gaagaccctg aggtcaagtt caactggtac    900
gtggacggcg tggaggtgca taatgccaag acaaagccgc gggaggagca gtacaacagc    960
acgtaccgtg tggtcagcgt cctcaccgtc ctgcaccagg actggctgaa tggcaaggag   1020
tacaagtgca aggtctccaa caaagccctc ccagccccca tcgagaaaac catctccaaa   1080
gccaaagggc agccccgaga accacaggtg tacaccctgc ccccatcccg ggaggagatg   1140
accaagaacc aggtcagcct gacctgcctg gtcaaaggct tctatcccag cgacatcgcc   1200
gtggagtggg agagcaatgg gcagccggag aacaactaca agaccacgcc tcccgtgctg   1260
gactccgacg gctccttctt cctctacagc aagctcaccg tggacaagag caggtggcag   1320
caggggaacg tcttctcatg ctccgtgatg catgaggctc tgcacaacca ctacacgcag   1380
aagagcctct ccctgtctcc gggtaaatga ctcgag                              1416

<210> SEQ ID NO 77
```

<211> LENGTH: 759
<212> TYPE: DNA
<213> ORGANISM: Artificial Sequence
<220> FEATURE:
<223> OTHER INFORMATION: Synthetic nucleotide sequence of light chain of anti-c-Met antibody (AbF46 or huAbF46-H1)
<220> FEATURE:
<221> NAME/KEY: misc_difference
<222> LOCATION: (1)..(6)
<223> OTHER INFORMATION: EcoRI restriction site
<220> FEATURE:
<221> NAME/KEY: misc_difference
<222> LOCATION: (7)..(90)
<223> OTHER INFORMATION: signal sequence
<220> FEATURE:
<221> NAME/KEY: misc_difference
<222> LOCATION: (91)..(432)
<223> OTHER INFORMATION: VL - light chain variable region
<220> FEATURE:
<221> NAME/KEY: misc_difference
<222> LOCATION: (430)..(435)
<223> OTHER INFORMATION: BsiWI restriction site
<220> FEATURE:
<221> NAME/KEY: misc_difference
<222> LOCATION: (433)..(750)
<223> OTHER INFORMATION: CL - light chain constant region
<220> FEATURE:
<221> NAME/KEY: misc_difference
<222> LOCATION: (751)..(753)
<223> OTHER INFORMATION: stop codon
<220> FEATURE:
<221> NAME/KEY: misc_difference
<222> LOCATION: (754)..(759)
<223> OTHER INFORMATION: XhoI restriction site

<400> SEQUENCE: 77

```
gaattcacta gtgattaatt cgccgccacc atggattcac aggcccaggt cctcatgttg    60
ctgctgctat cggtatctgg tacctgtgga cattttgatg acccagtc tccatcctcc     120 ctgactgtgt cagcaggaga aaggtcact atgagctgca agtccagtca gagtctttta    180
gctagtggca accaaaataa ctacttggcc tggcaccagc agaaaccagg acgatctcct   240
aaaatgctga taatttgggc atccactagg gtatctggag tccctgatcg cttcataggc   300
agtggatctg ggacggattt cactctgacc atcaacagtg tgcaggctga agatctggct  360
gtttattact gtcagcagtc ctacagcgct ccgctcacgt tcggtgctgg gaccaagctg  420
gagctgaaac gtacggtggc tgcaccatct gtcttcatct tcccgccatc tgatgagcag  480
ttgaaatctg gaactgcctc tgttgtgtgc ctgctgaata acttctatcc cagagaggcc  540
aaagtacagt ggaaggtgga taacgccctc caatcgggta actcccagga gagtgtcaca  600
gagcaggaca gcaaggacag cacctacagc ctcagcagca ccctgacgct gagcaaagca  660
gactacgaga aacacaaagt ctacgcctgc gaagtcaccc atcagggcct gagctcgccc  720
gtcacaaaga gcttcaacag gggagagtgt tgactcgag                         759
```

<210> SEQ ID NO 78
<211> LENGTH: 4170
<212> TYPE: DNA
<213> ORGANISM: Artificial Sequence
<220> FEATURE:
<223> OTHER INFORMATION: Synthetic polynucleotide encoding c-Met protein

<400> SEQUENCE: 78

```
atgaaggccc ccgctgtgct tgcacctggc atcctcgtgc tcctgtttac cttggtgcag    60
aggagcaatg gggagtgtaa agaggcacta gcaaagtccg agatgaatgt gaatatgaag   120
tatcagcttc ccaacttcac cgcggaaaca cccatccaga atgtcattct acatgagcat   180
```

```
cacattttcc ttggtgccac taactacatt tatgttttaa atgaggaaga ccttcagaag    240
gttgctgagt acaagactgg gcctgtgctg gaacacccag attgtttccc atgtcaggac    300
tgcagcagca aagccaattt atcaggaggt gtttggaaag ataacatcaa catggctcta    360
gttgtcgaca cctactatga tgatcaactc attagctgtg gcagcgtcaa cagagggacc    420
tgccagcgac atgtctttcc ccacaatcat actgctgaca tacagtcgga ggttcactgc    480
atattctccc cacagataga agagcccagc cagtgtcctg actgtgtggt gagcgccctg    540
ggagccaaag tcctttcatc tgtaaaggac cggttcatca acttctttgt aggcaatacc    600
ataaattctt cttatttccc agatcatcca ttgcattcga tatcagtgag aaggctaaag    660
gaaacgaaag atggttttat gttttgacg gaccagtcct acattgatgt tttacctgag    720
ttcagagatt cttaccccat taagtatgtc catgcctttg aaagcaacaa ttttatttac    780
ttcttgacgg tccaaaggga aactctagat gctcagactt tcacacaag aataatcagg    840 ttctgttcca taaactctgg attgcattcc tacatggaaa tgcctctgga gtgtattctc    900
acagaaaaga gaaaaagag atccacaaag aaggaagtgt taatatact tcaggctgcg    960 tatgtcagca agcctgggc ccagcttgct agacaaatag gagccagcct gaatgatgac   1020
attcttttcg gggtgttcgc acaaagcaag ccagattctg ccgaaccaat ggatcgatct   1080
gccatgtgtg cattccctat caaatatgtc aacgacttct tcaacaagat cgtcaacaaa   1140
aacaatgtga gatgtctcca gcattttac ggacccaatc atgagcactg ctttaatagg   1200
acacttctga gaaattcatc aggctgtgaa gcgcgccgtg atgaatatcg aacagagttt   1260
accacagctt tgcagcgcgt tgacttattc atgggtcaat tcagcgaagt cctcttaaca   1320
tctatatcca ccttcattaa aggagacctc accatagcta atcttgggac atcagagggt   1380
cgcttcatgc aggttgtggt ttctcgatca ggaccatcaa cccctcatgt gaattttctc   1440
ctggactccc atccagtgtc tccagaagtg attgtggagc atacattaaa ccaaaatggc   1500
tacacactgg ttatcactgg gaagaagatc acgaagatcc cattgaatgg cttgggctgc   1560
agacatttcc agtcctgcag tcaatgcctc tctgccccac cctttgttca gtgtggctgg   1620
tgccacgaca aatgtgtgcg atcggaggaa tgcctgagcg ggacatggac tcaacagatc   1680
tgtctgcctg caatctacaa ggttttccca aatagtgcac cccttgaagg agggacaagg   1740
ctgaccatat gtggctggga ctttggattt cggaggaata taaatttga tttaaagaaa   1800 actagagttc tccttggaaa tgagagctgc accttgactt taagtgagag cacgatgaat   1860
acattgaaat gcacagttgg tcctgccatg aataagcatt tcaatatgtc cataattatt   1920
tcaaatggcc acgggacaac acaatacagt acattctcct atgtggatcc tgtaataaca   1980
agtatttcgc cgaaatacgg tcctatggct ggtggcactt tacttacttt aactggaaat   2040
tacctaaaca gtgggaattc tagacacatt tcaattggtg gaaaaacatg tactttaaaa   2100
agtgtgtcaa acagtattct tgaatgttat accccagccc aaaccatttc aactgagttt   2160
gctgttaaat tgaaaattga cttagccaac cgagagacaa gcatcttcag ttaccgtgaa   2220
gatcccattg tctatgaaat tcatccaacc aaatctttta ttagtggtgg gagcacaata   2280
acaggtgttg ggaaaaacct gaattcagtt agtgtcccga aatggtcat aaatgtgcat   2340 gaagcaggaa ggaactttac agtggcatgt caacatcgct ctaattcaga gataatctgt   2400
tgtaccactc cttccctgca acagctgaat ctgcaactcc ccctgaaaac caaagccttt   2460
ttcatgttag atgggatcct ttccaaatac tttgatctca tttatgtaca taatcctgtg   2520
tttaagcctt ttgaaaagcc agtgatgatc tcaatgggca atgaaaatgt actggaaatt   2580
```

```
aagggaaatg atattgaccc tgaagcagtt aaaggtgaag tgttaaaagt tggaaataag    2640
agctgtgaga atatacactt acattctgaa gccgttttat gcacggtccc caatgacctg    2700
ctgaaattga acagcgagct aaatatagag tggaagcaag caatttcttc aaccgtcctt    2760
ggaaaagtaa tagttcaacc agatcagaat ttcacaggat tgattgctgg tgttgtctca    2820
atatcaacag cactgttatt actacttggg ttttttcctgt ggctgaaaaa gagaaagcaa    2880
attaaagatc tgggcagtga attagttcgc tacgatgcaa gagtacacac tcctcatttg    2940
gataggcttg taagtgcccg aagtgtaagc ccaactacag aaatggtttc aaatgaatct    3000
gtagactacc gagctacttt tccagaagat cagtttccta attcatctca gaacggttca    3060
tgccgacaag tgcagtatcc tctgacagac atgtccccca tcctaactag tggggactct    3120
gatatatcca gtccattact gcaaaatact gtccacattg acctcagtgc tctaaatcca    3180
gagctggtcc aggcagtgca gcatgtagtg attgggccca gtagcctgat tgtgcatttc    3240
aatgaagtca taggaagagg gcattttggt tgtgtatatc atgggacttt gttggacaat    3300
gatggcaaga aaattcactg tgctgtgaaa tccttgaaca gaatcactga cataggagaa    3360
gtttcccaat ttctgaccga gggaatcatc atgaaagatt ttagtcatcc caatgtcctc    3420
tcgctcctgg gaatctgcct gcgaagtgaa gggtctccgc tggtggtcct accatacatg    3480
aaacatggag atcttcgaaa tttcattcga aatgagactc ataatccaac tgtaaaagat    3540
cttattggct ttggtcttca agtagccaaa ggcatgaaat atcttgcaag caaaaagttt    3600
gtccacagag acttggctgc aagaaactgt atgctggatg aaaaattcac agtcaaggtt    3660
gctgattttg gtcttgccag agacatgtat gataaagaat actatagtgt acacaacaaa    3720
acaggtgcaa agctgccagt gaagtggatg gctttggaaa gtctgcaaac tcaaaagttt    3780
accaccaagt cagatgtgtg gtcctttggc gtgctcctct gggagctgat gacaagagga    3840
gccccacctt atcctgacgt aaacaccttt gatataactg tttacttgtt gcaagggaga    3900
agactcctac aacccgaata ctgcccagac cccttatatg aagtaatgct aaaatgctgg    3960
caccctaaag ccgaaatgcg cccatccttt tctgaactgg tgtcccggat atcagcgatc    4020
ttctctactt tcattgggga gcactatgtc catgtgaacg ctacttatgt gaacgtaaaa    4080
tgtgtcgctc cgtatccttc tctgttgtca tcagaagata cgctgatga tgaggtggac    4140 acacgaccag cctccttctg ggagacatca                                     4170
```

<210> SEQ ID NO 79
<211> LENGTH: 444
<212> TYPE: PRT
<213> ORGANISM: Artificial Sequence
<220> FEATURE:
<223> OTHER INFORMATION: Synthetic SEMA domain of c-Met

<400> SEQUENCE: 79

```
Leu His Glu His His Ile Phe Leu Gly Ala Thr Asn Tyr Ile Tyr Val
  1               5                  10                  15

Leu Asn Glu Glu Asp Leu Gln Lys Val Ala Glu Tyr Lys Thr Gly Pro
             20                  25                  30

Val Leu Glu His Pro Asp Cys Phe Pro Cys Gln Asp Cys Ser Ser Lys
         35                  40                  45

Ala Asn Leu Ser Gly Gly Val Trp Lys Asp Asn Ile Asn Met Ala Leu
     50                  55                  60

Val Val Asp Thr Tyr Tyr Asp Asp Gln Leu Ile Ser Cys Gly Ser Val
 65                  70                  75                  80
```

```
Asn Arg Gly Thr Cys Gln Arg His Val Phe Pro His Asn His Thr Ala
                85                  90                  95

Asp Ile Gln Ser Glu Val His Cys Ile Phe Ser Pro Gln Ile Glu Glu
            100                 105                 110

Pro Ser Gln Cys Pro Asp Cys Val Val Ser Ala Leu Gly Ala Lys Val
        115                 120                 125

Leu Ser Ser Val Lys Asp Arg Phe Ile Asn Phe Val Gly Asn Thr
130                 135                 140

Ile Asn Ser Ser Tyr Phe Pro Asp His Pro Leu His Ser Ile Ser Val
145                 150                 155                 160

Arg Arg Leu Lys Glu Thr Lys Asp Gly Phe Met Phe Leu Thr Asp Gln
                165                 170                 175

Ser Tyr Ile Asp Val Leu Pro Glu Phe Arg Asp Ser Tyr Pro Ile Lys
            180                 185                 190

Tyr Val His Ala Phe Glu Ser Asn Asn Phe Ile Tyr Phe Leu Thr Val
        195                 200                 205

Gln Arg Glu Thr Leu Asp Ala Gln Thr Phe His Thr Arg Ile Ile Arg
210                 215                 220

Phe Cys Ser Ile Asn Ser Gly Leu His Ser Tyr Met Glu Met Pro Leu
225                 230                 235                 240

Glu Cys Ile Leu Thr Glu Lys Arg Lys Lys Arg Ser Thr Lys Lys Glu
                245                 250                 255

Val Phe Asn Ile Leu Gln Ala Ala Tyr Val Ser Lys Pro Gly Ala Gln
            260                 265                 270

Leu Ala Arg Gln Ile Gly Ala Ser Leu Asn Asp Asp Ile Leu Phe Gly
        275                 280                 285

Val Phe Ala Gln Ser Lys Pro Asp Ser Ala Glu Pro Met Asp Arg Ser
290                 295                 300

Ala Met Cys Ala Phe Pro Ile Lys Tyr Val Asn Asp Phe Phe Asn Lys
305                 310                 315                 320

Ile Val Asn Lys Asn Asn Val Arg Cys Leu Gln His Phe Tyr Gly Pro
                325                 330                 335

Asn His Glu His Cys Phe Asn Arg Thr Leu Leu Arg Asn Ser Ser Gly
            340                 345                 350

Cys Glu Ala Arg Arg Asp Glu Tyr Arg Thr Glu Phe Thr Thr Ala Leu
        355                 360                 365

Gln Arg Val Asp Leu Phe Met Gly Gln Phe Ser Glu Val Leu Leu Thr
370                 375                 380

Ser Ile Ser Thr Phe Ile Lys Gly Asp Leu Thr Ile Ala Asn Leu Gly
385                 390                 395                 400

Thr Ser Glu Gly Arg Phe Met Gln Val Val Ser Arg Ser Gly Pro
                405                 410                 415

Ser Thr Pro His Val Asn Phe Leu Leu Asp Ser His Pro Val Ser Pro
            420                 425                 430

Glu Val Ile Val Glu His Thr Leu Asn Gln Asn Gly
        435                 440
```

<210> SEQ ID NO 80
<211> LENGTH: 451
<212> TYPE: PRT
<213> ORGANISM: Artificial Sequence
<220> FEATURE:
<223> OTHER INFORMATION: Synthetic PSI-IPT domain of c-Met

<400> SEQUENCE: 80

```
Tyr Thr Leu Val Ile Thr Gly Lys Lys Ile Thr Lys Ile Pro Leu Asn
  1               5                  10                  15

Gly Leu Gly Cys Arg His Phe Gln Ser Cys Ser Gln Cys Leu Ser Ala
             20                  25                  30

Pro Pro Phe Val Gln Cys Gly Trp Cys His Asp Lys Cys Val Arg Ser
         35                  40                  45

Glu Glu Cys Leu Ser Gly Thr Trp Thr Gln Gln Ile Cys Leu Pro Ala
     50                  55                  60

Ile Tyr Lys Val Phe Pro Asn Ser Ala Pro Leu Glu Gly Gly Thr Arg
 65              70                  75                      80

Leu Thr Ile Cys Gly Trp Asp Phe Gly Phe Arg Arg Asn Asn Lys Phe
                 85                  90                  95

Asp Leu Lys Lys Thr Arg Val Leu Leu Gly Asn Glu Ser Cys Thr Leu
            100                 105                 110

Thr Leu Ser Glu Ser Thr Met Asn Thr Leu Lys Cys Thr Val Gly Pro
        115                 120                 125

Ala Met Asn Lys His Phe Asn Met Ser Ile Ile Ser Asn Gly His
130                 135                 140

Gly Thr Thr Gln Tyr Ser Thr Phe Ser Tyr Val Asp Pro Val Ile Thr
145                 150                 155                 160

Ser Ile Ser Pro Lys Tyr Gly Pro Met Ala Gly Gly Thr Leu Leu Thr
                165                 170                 175

Leu Thr Gly Asn Tyr Leu Asn Ser Gly Asn Ser Arg His Ile Ser Ile
            180                 185                 190

Gly Gly Lys Thr Cys Thr Leu Lys Ser Val Ser Asn Ser Ile Leu Glu
        195                 200                 205

Cys Tyr Thr Pro Ala Gln Thr Ile Ser Thr Glu Phe Ala Val Lys Leu
        210                 215                 220

Lys Ile Asp Leu Ala Asn Arg Glu Thr Ser Ile Phe Ser Tyr Arg Glu
225                 230                 235                 240

Asp Pro Ile Val Tyr Glu Ile His Pro Thr Lys Ser Phe Ile Ser Thr
                245                 250                 255

Trp Trp Lys Glu Pro Leu Asn Ile Val Ser Phe Leu Phe Cys Phe Ala
            260                 265                 270

Ser Gly Gly Ser Thr Ile Thr Gly Val Gly Lys Asn Leu Asn Ser Val
        275                 280                 285

Ser Val Pro Arg Met Val Ile Asn Val His Glu Ala Gly Arg Asn Phe
        290                 295                 300

Thr Val Ala Cys Gln His Arg Ser Asn Ser Glu Ile Ile Cys Cys Thr
305                 310                 315                 320

Thr Pro Ser Leu Gln Gln Leu Asn Leu Gln Leu Pro Leu Lys Thr Lys
                325                 330                 335

Ala Phe Phe Met Leu Asp Gly Ile Leu Ser Lys Tyr Phe Asp Leu Ile
            340                 345                 350

Tyr Val His Asn Pro Val Phe Lys Pro Phe Glu Lys Pro Val Met Ile
        355                 360                 365

Ser Met Gly Asn Glu Asn Val Leu Glu Ile Lys Gly Asn Asp Ile Asp
370                 375                 380

Pro Glu Ala Val Lys Gly Glu Val Leu Lys Val Gly Asn Lys Ser Cys
385                 390                 395                 400

Glu Asn Ile His Leu His Ser Glu Ala Val Leu Cys Thr Val Pro Asn
                405                 410                 415
```

```
Asp Leu Leu Lys Leu Asn Ser Glu Leu Asn Ile Glu Trp Lys Gln Ala
            420                 425                 430

Ile Ser Ser Thr Val Leu Gly Lys Val Ile Val Gln Pro Asp Gln Asn
        435                 440                 445

Phe Thr Gly
    450

<210> SEQ ID NO 81
<211> LENGTH: 313
<212> TYPE: PRT
<213> ORGANISM: Artificial Sequence
<220> FEATURE:
<223> OTHER INFORMATION: Synthetic TyrKc domain of c-Met

<400> SEQUENCE: 81

Val His Phe Asn Glu Val Ile Gly Arg Gly His Phe Gly Cys Val Tyr
 1               5                  10                  15

His Gly Thr Leu Leu Asp Asn Asp Gly Lys Lys Ile His Cys Ala Val
            20                  25                  30

Lys Ser Leu Asn Arg Ile Thr Asp Ile Gly Glu Val Ser Gln Phe Leu
        35                  40                  45

Thr Glu Gly Ile Ile Met Lys Asp Phe Ser His Pro Asn Val Leu Ser
 50                  55                  60

Leu Leu Gly Ile Cys Leu Arg Ser Gly Ser Pro Leu Val Val Leu
65                  70                  75                  80

Pro Tyr Met Lys His Gly Asp Leu Arg Asn Phe Ile Arg Asn Glu Thr
                85                  90                  95

His Asn Pro Thr Val Lys Asp Leu Ile Gly Phe Gly Leu Gln Val Ala
            100                 105                 110

Lys Gly Met Lys Tyr Leu Ala Ser Lys Lys Phe Val His Arg Asp Leu
        115                 120                 125

Ala Ala Arg Asn Cys Met Leu Asp Glu Lys Phe Thr Val Lys Val Ala
    130                 135                 140

Asp Phe Gly Leu Ala Arg Asp Met Tyr Asp Lys Glu Tyr Tyr Ser Val
145                 150                 155                 160

His Asn Lys Thr Gly Ala Lys Leu Pro Val Lys Trp Met Ala Leu Glu
                165                 170                 175

Ser Leu Gln Thr Gln Lys Phe Thr Thr Lys Ser Asp Val Trp Ser Phe
            180                 185                 190

Gly Val Leu Leu Trp Glu Leu Met Thr Arg Gly Ala Pro Pro Tyr Pro
        195                 200                 205

Asp Val Asn Thr Phe Asp Ile Thr Val Tyr Leu Leu Gln Gly Arg Arg
    210                 215                 220

Leu Leu Gln Pro Glu Tyr Cys Pro Asp Pro Leu Tyr Glu Val Met Leu
225                 230                 235                 240

Lys Cys Trp His Pro Lys Ala Glu Met Arg Pro Ser Phe Ser Glu Leu
                245                 250                 255

Val Ser Arg Ile Ser Ala Ile Phe Ser Thr Phe Ile Gly Glu His Tyr
            260                 265                 270

Val His Val Asn Ala Thr Tyr Val Asn Val Lys Cys Val Ala Pro Tyr
        275                 280                 285

Pro Ser Leu Leu Ser Ser Glu Asp Asn Ala Asp Asp Glu Val Asp Thr
    290                 295                 300

Arg Pro Ala Ser Phe Trp Glu Thr Ser
305                 310
```

<210> SEQ ID NO 82
<211> LENGTH: 1332
<212> TYPE: DNA
<213> ORGANISM: Artificial Sequence
<220> FEATURE:
<223> OTHER INFORMATION: Synthetic polynucleotide encoding SEMA domain of c-Met

<400> SEQUENCE: 82

```
ctacatgagc atcacatttt ccttggtgcc actaactaca tttatgtttt aaatgaggaa      60
gaccttcaga aggttgctga gtacaagact gggcctgtgc tggaacaccc agattgtttc     120
ccatgtcagg actgcagcag caaagccaat ttatcaggag tgtttggaa agataacatc      180
aacatggctc tagttgtcga cacctactat gatgatcaac tcattagctg tggcagcgtc     240
aacagaggga cctgccagcg acatgtcttt ccccacaatc atactgctga catacagtcg     300
gaggttcact gcatattctc cccacagata aagagccca gccagtgtcc tgactgtgtg      360
gtgagcgccc tggagccaa agtcctttca tctgtaaagg accggttcat caacttcttt      420
gtaggcaata ccataaattc ttcttatttc ccagatcatc cattgcattc gatatcagtg     480
agaaggctaa aggaaacgaa agatgggtttt atgtttttga cggaccagtc ctacattgat      540
gttttacctg agttcagaga ttcttacccc attaagtatg tccatgcctt tgaaagcaac      600
aattttattt acttcttgac ggtccaaagg gaaactctag atgctcagac ttttcacaca      660
agaataatca ggttctgttc cataaactct ggattgcatt cctacatgga aatgcctctg      720
gagtgtattc tcacagaaaa gagaaaaaag agatccacaa agaaggagt gtttaatata      780
cttcaggctg cgtatgtcag caagcctggg gcccagcttg ctagacaaat aggagccagc      840
ctgaatgatg acattctttt cggggtgttc gcacaaagca agccagattc tgccgaacca      900
atggatcgat ctgccatgtg tgcattccct atcaaatatg tcaacgactt cttcaacaag      960
atcgtcaaca aaaacaatgt gagatgtctc cagcatttttt acggacccaa tcatgagcac     1020
tgctttaata ggacacttct gagaaattca tcaggctgtg aagcgcgccg tgatgaatat     1080
cgaacagagt ttaccacagc tttgcagcgc gttgacttat tcatgggtca attcagcgaa     1140
gtcctcttaa catctatatc caccttcatt aaaggagacc tcaccatagc taatcttggg     1200
acatcagagg gtcgcttcat gcaggttgtg gtttctcgat caggaccatc aacccctcat     1260
gtgaattttc tcctggactc ccatccagtg tctccagaag tgattgtgga gcatacatta     1320
aaccaaaatg gc                                                         1332
```

<210> SEQ ID NO 83
<211> LENGTH: 1299
<212> TYPE: DNA
<213> ORGANISM: Artificial Sequence
<220> FEATURE:
<223> OTHER INFORMATION: Synthetic polynucleotide encoding PSI-IPT domain of c-Met

<400> SEQUENCE: 83

```
tacacactgg ttatcactgg gaagaagatc acgaagatcc cattgaatgg cttgggctgc      60
agacatttcc agtcctgcag tcaatgcctc tctgccccac cctttgttca gtgtggctgg     120
tgccacgaca atgtgtgcg atcggaggaa tgcctgagcg ggacatggac tcaacagatc     180
tgtctgcctg caatctacaa ggtttttccca aatagtgcac cccttgaagg agggacaagg     240
ctgaccatat gtggctggga ctttggattt cggaggaata taaaatttga tttaaagaaa      300
actagagttc tccttggaaa tgagagctgc accttgactt aagtgagag cacgatgaat     360
```

```
acattgaaat gcacagttgg tcctgccatg aataagcatt tcaatatgtc cataattatt      420
tcaaatggcc acgggacaac acaatacagt acattctcct atgtggatcc tgtaataaca      480
agtatttcgc cgaaatacgg tcctatggct ggtggcactt tacttacttt aactggaaat      540
tacctaaaca gtgggaattc tagacacatt tcaattggtg gaaaaacatg tactttaaaa      600
agtgtgtcaa acagtattct tgaatgttat accccagccc aaaccatttc aactgagttt      660
gctgttaaat tgaaaattga cttagccaac cgagagacaa gcatcttcag ttaccgtgaa      720
gatcccattg tctatgaaat tcatccaacc aaatcttta ttagtggtgg gagcacaata       780
acaggtgttg ggaaaaacct gaattcagtt agtgtcccga gaatggtcat aaatgtgcat      840
gaagcaggaa ggaactttac agtggcatgt caacatcgct ctaattcaga gataatctgt      900
tgtaccactc cttccctgca acagctgaat ctgcaactcc ccctgaaaac caaagccttt      960
ttcatgttag atgggatcct ttccaaatac tttgatctca tttatgtaca taatcctgtg     1020
tttaagcctt ttgaaaagcc agtgatgatc tcaatgggca atgaaaatgt actggaaatt     1080
aagggaaatg atattgaccc tgaagcagtt aaaggtgaag tgttaaaagt tggaaataag     1140
agctgtgaga atatacactt acattctgaa gccgttttat gcacggtccc caatgacctg     1200
ctgaaattga acagcgagct aaatatagag tggaagcaag caatttcttc aaccgtcctt     1260
ggaaaagtaa tagttcaacc agatcagaat ttcacagga                            1299

<210> SEQ ID NO 84
<211> LENGTH: 939
<212> TYPE: DNA
<213> ORGANISM: Artificial Sequence
<220> FEATURE:
<223> OTHER INFORMATION: Synthetic polynucleotide encoding TyrKc domain
      of c-Met

<400> SEQUENCE: 84
gtgcatttca atgaagtcat aggaagaggg cattttggtt gtgtatatca tgggactttg       60
ttggacaatg atggcaagaa aattcactgt gctgtgaaat ccttgaacag aatcactgac      120
ataggagaag tttcccaatt tctgaccgag ggaatcatca tgaaagattt tagtcatccc      180
aatgtcctct cgctcctggg aatctgcctg cgaagtgaag ggtctccgct ggtggtccta      240
ccatacatga acatggagag tcttcgaaat tcattcgaa atgagactca taatccaact       300
gtaaaagatc ttattggctt tggtcttcaa gtagccaaag gcatgaaata tcttgcaagc      360
aaaaagtttg tccacagaga cttggctgca agaaactgta tgctggatga aaaattcaca      420
gtcaaggttg ctgattttgg tcttgccaga gacatgtatg ataaagaata ctatagtgta      480
cacaacaaaa caggtgcaaa gctgccagtg aagtggatgg ctttggaaag tctgcaaact      540
caaaagttta ccaccaagtc agatgtgtgg tcctttggcg tgctcctctg ggagctgatg      600
acaagaggag cccccaccta tcctgacgta aacacctttg atataactgt ttacttgttg      660
caagggagaa gactcctaca acccgaatac tgcccagacc ccttatatga agtaatgcta      720
aaatgctggc accctaaagc cgaaatgcgc ccatcctttt ctgaactggt gtccggata       780 tcagcgatct tctctacttt cattggggag cactatgtcc atgtgaacgc tacttatgtg      840
aacgtaaaat gtgtcgctcc gtatccttct ctgttgtcat cagaagataa cgctgatgat      900
gaggtggaca cacgaccagc ctccttctgg gagacatca                            939

<210> SEQ ID NO 85
<211> LENGTH: 13
```

-continued

```
<212> TYPE: PRT
<213> ORGANISM: Artificial Sequence
<220> FEATURE:
<223> OTHER INFORMATION: Synthetic heavy chain CDR3 of anti-c-Met
      antibody

<400> SEQUENCE: 85

Asp Asn Trp Phe Ala Tyr Trp Gly Gln Gly Thr Leu Val
  1               5                  10

<210> SEQ ID NO 86
<211> LENGTH: 10
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 86

Leu Thr Phe Gly Ala Gly Thr Lys Leu Glu
  1               5                  10

<210> SEQ ID NO 87
<211> LENGTH: 117
<212> TYPE: PRT
<213> ORGANISM: Artificial Sequence
<220> FEATURE:
<223> OTHER INFORMATION: Synthetic heavy chain variable region of
      monoclonal antibody AbF46

<400> SEQUENCE: 87

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Ala Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asp Thr Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ala
            115

<210> SEQ ID NO 88
<211> LENGTH: 114
<212> TYPE: PRT
<213> ORGANISM: Artificial Sequence
<220> FEATURE:
<223> OTHER INFORMATION: Synthetic light chain variable region of
      anti-c-Met antibody

<400> SEQUENCE: 88

Asp Ile Leu Met Thr Gln Ser Pro Ser Ser Leu Thr Val Ser Ala Gly
  1               5                  10                  15

Glu Lys Val Thr Met Ser Cys Lys Ser Ser Gln Ser Leu Leu Ala Ser
             20                  25                  30

Gly Asn Gln Asn Asn Tyr Leu Ala Trp His Gln Gln Lys Pro Gly Arg
         35                  40                  45
```

```
Ser Pro Lys Met Leu Ile Ile Trp Ala Ser Thr Arg Val Ser Gly Val
        50                  55                  60

Pro Asp Arg Phe Ile Gly Ser Gly Ser Gly Thr Asp Phe Thr Leu Thr
 65                  70                  75                  80

Ile Asn Ser Val Gln Ala Glu Asp Leu Ala Val Tyr Tyr Cys Gln Gln
                 85                  90                  95

Ser Tyr Ser Ala Pro Leu Thr Phe Gly Ala Gly Thr Lys Leu Glu Leu
            100                 105                 110

Lys Arg

<210> SEQ ID NO 89
<211> LENGTH: 17
<212> TYPE: PRT
<213> ORGANISM: Artificial Sequence
<220> FEATURE:
<223> OTHER INFORMATION: Synthetic light chain CDR3 of anti-c-Met
      antibody

<400> SEQUENCE: 89

Gln Gln Ser Tyr Ser Ala Pro Leu Thr Phe Gly Ala Gly Thr Lys Leu
  1               5                  10                  15

Glu

<210> SEQ ID NO 90
<211> LENGTH: 117
<212> TYPE: PRT
<213> ORGANISM: Artificial Sequence
<220> FEATURE:
<223> OTHER INFORMATION: Synthetic heavy chain variable region of AT-VH1

<400> SEQUENCE: 90

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Ser Thr
 65                  70                  75                  80

Leu Tyr Leu Gln Met Asn Ser Leu Arg Ala Glu Asp Ser Ala Thr Tyr
                 85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 91
<211> LENGTH: 117
<212> TYPE: PRT
<213> ORGANISM: Artificial Sequence
<220> FEATURE:
<223> OTHER INFORMATION: Synthetic heavy chain variable region of AT-VH2

<400> SEQUENCE: 91

Glu Val Lys Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
```

```
                    20                  25                  30
Tyr Met Ser Trp Val Arg Gln Pro Pro Gly Lys Gly Leu Glu Trp Leu
            35                  40                  45
Gly Phe Ile Arg Asn Lys Ala Asn Gly Tyr Thr Thr Glu Tyr Ser Ala
        50                  55                  60
Ser Val Lys Gly Arg Phe Thr Ile Ser Arg Asp Asn Ser Lys Ser Thr
 65                  70                  75                  80
Leu Tyr Leu Gln Met Asn Ser Leu Arg Ala Glu Asp Thr Ala Thr Tyr
                85                  90                  95
Tyr Cys Ala Arg Asp Asn Trp Phe Ala Tyr Trp Gly Gln Gly Thr Leu
            100                 105                 110
Val Thr Val Ser Ser
        115

<210> SEQ ID NO 92
<211> LENGTH: 117
<212> TYPE: PRT
<213> ORGANISM: Artificial Sequence
<220> FEATURE:
<223> OTHER INFORMATION: Synthetic heavy chain variable region of AT-VH3

<400> SEQUENCE: 92

Glu Val Gln Leu Val Glu Ser Gly Gly Gly Leu Val Gln Pro Gly Gly
 1               5                  10                  15
Ser Leu Arg Leu Ser Cys Ala Thr Ser Gly Phe Thr Phe Thr Asp Tyr
            20                  25                  30
Tyr Met Ser Trp Val Arg Gln Pro Pro Gly Lys Gly Leu Glu Trp Leu
            35                  40                  45
Gly Phe Ile Arg Asn Lys Ala Asn Gly Tyr Thr Thr Glu Tyr Ser Ala
        50                  55                  60
Ser Val Lys Gly Arg Phe Thr Ile Ser Arg Asp Asn Ser Lys Ser Thr
 65                  70                  75                  80
Leu Tyr Leu Gln Met Asn Ser Leu Arg Ala Glu Asp Thr Ala Thr Tyr
                85                  90                  95
Tyr Cys Ala Arg Asp Asn Trp Phe Ala Tyr Trp Gly Gln Gly Thr Leu
            100                 105                 110
Val Thr Val Ser Ser
        115

<210> SEQ ID NO 93
<211> LENGTH: 117
<212> TYPE: PRT
<213> ORGANISM: Artificial Sequence
<220> FEATURE:
<223> OTHER INFORMATION: Synthetic heavy chain variable region of AT-VH4

<400> SEQUENCE: 93

Glu Val Gln Leu Val Glu Ser Gly Gly Gly Leu Val Gln Pro Gly Gly
 1               5                  10                  15
Ser Leu Arg Leu Ser Cys Ala Thr Ser Gly Phe Thr Phe Thr Asp Tyr
            20                  25                  30
Tyr Met Ser Trp Val Arg Gln Pro Pro Gly Lys Gly Leu Glu Trp Leu
            35                  40                  45
Gly Phe Ile Arg Asn Lys Ala Asn Gly Tyr Thr Thr Glu Tyr Ser Ala
        50                  55                  60
Ser Val Lys Gly Arg Phe Thr Ile Ser Arg Asp Asn Ser Lys Asn Thr
 65                  70                  75                  80
```

```
Leu Tyr Leu Gln Met Asn Ser Leu Arg Ala Glu Asp Thr Ala Thr Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 94
<211> LENGTH: 117
<212> TYPE: PRT
<213> ORGANISM: Artificial Sequence
<220> FEATURE:
<223> OTHER INFORMATION: Synthetic heavy chain variable region of AT-VH5

<400> SEQUENCE: 94

Glu Val Gln Leu Val Glu Ser Gly Gly Gly Leu Val Gln Pro Gly Gly
  1               5                  10                  15

Ser Leu Arg Leu Ser Cys Ala Thr Ser Gly Phe Thr Phe Thr Asp Tyr
             20                  25                  30

Tyr Met Ser Trp Val Arg Gln Pro Pro Gly Lys Gly Leu Glu Trp Leu
         35                  40                  45

Gly Phe Ile Arg Asn Lys Ala Asn Gly Tyr Thr Thr Glu Tyr Ser Ala
     50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 95
<211> LENGTH: 114
<212> TYPE: PRT
<213> ORGANISM: Artificial Sequence
<220> FEATURE:
<223> OTHER INFORMATION: Synthetic light chain variable region of anti
      c-Met humanized antibody(huAbF46-H4)

<400> SEQUENCE: 95

Asp Ile Gln Met Thr Gln Ser Pro Ser Ser Leu Ser Ala Ser Val Gly
  1               5                  10                  15

Asp Arg Val Thr Ile Thr Cys Lys Ser Ser Gln Ser Leu Leu Ala Ser
             20                  25                  30

Gly Asn Gln Asn Asn Tyr Leu Ala Trp His Gln Gln Lys Pro Gly Lys
         35                  40                  45

Ala Pro Lys Met Leu Ile Ile Trp Ala Ser Thr Arg Val Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 96
```

```
<211> LENGTH: 113
<212> TYPE: PRT
<213> ORGANISM: Artificial Sequence
<220> FEATURE:
<223> OTHER INFORMATION: Synthetic light chain variable region of AT-Vk1

<400> SEQUENCE: 96

Asp Ile Leu Met Thr Gln Ser Pro Ser Ser Leu Thr Ala Ser Val Gly
 1               5                  10                  15

Asp Arg Val Thr Met Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 97
<211> LENGTH: 113
<212> TYPE: PRT
<213> ORGANISM: Artificial Sequence
<220> FEATURE:
<223> OTHER INFORMATION: Synthetic light chain variable region of AT-Vk2

<400> SEQUENCE: 97

Asp Ile Leu Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
    50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Ser Tyr Ser Ala Pro Leu Thr Phe Gly Gln Gly Thr Lys Leu Glu Ile
            100                 105                 110

Lys

<210> SEQ ID NO 98
<211> LENGTH: 113
<212> TYPE: PRT
<213> ORGANISM: Artificial Sequence
<220> FEATURE:
<223> OTHER INFORMATION: Synthetic light chain variable region of AT-Vk3

<400> SEQUENCE: 98

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30
```

```
Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ile Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys

<210> SEQ ID NO 99
<211> LENGTH: 113
<212> TYPE: PRT
<213> ORGANISM: Artificial Sequence
<220> FEATURE:
<223> OTHER INFORMATION: Synthetic light chain variable region of AT-Vk4

<400> SEQUENCE: 99

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
                20                  25                  30

Gly Asn Gln Asn Asn Tyr Leu Ala Trp His Gln Gln Lys Pro Gly Lys
            35                  40                  45

Ala Pro Lys Met Leu Ile Ile Trp Ala Ser Thr Arg Val Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Ser Tyr Ser Ala Pro Leu Thr Phe Gly Gln Gly Thr Lys Leu Glu Ile
            100                 105                 110

Lys

<210> SEQ ID NO 100
<211> LENGTH: 13
<212> TYPE: PRT
<213> ORGANISM: Artificial Sequence
<220> FEATURE:
<223> OTHER INFORMATION: Synthetic modified hinge region(U7-HC6)

<400> SEQUENCE: 100

Glu Pro Ser Cys Asp Lys His Cys Cys Pro Pro Cys Pro
 1               5                  10

<210> SEQ ID NO 101
<211> LENGTH: 13
<212> TYPE: PRT
<213> ORGANISM: Artificial Sequence
<220> FEATURE:
<223> OTHER INFORMATION: Synthetic modified hinge region(U6-HC7)

<400> SEQUENCE: 101

Glu Pro Lys Ser Cys Asp Cys His Cys Pro Pro Cys Pro
 1               5                  10

<210> SEQ ID NO 102
```

```
<211> LENGTH: 12
<212> TYPE: PRT
<213> ORGANISM: Artificial Sequence
<220> FEATURE:
<223> OTHER INFORMATION: Synthetic modified hinge region(U3-HC9)

<400> SEQUENCE: 102

Glu Arg Lys Cys Cys Val Glu Cys Pro Pro Cys Pro
1               5                   10

<210> SEQ ID NO 103
<211> LENGTH: 14
<212> TYPE: PRT
<213> ORGANISM: Artificial Sequence
<220> FEATURE:
<223> OTHER INFORMATION: Synthetic modified hinge region(U6-HC8)

<400> SEQUENCE: 103

Glu Pro Arg Asp Cys Gly Cys Lys Pro Cys Pro Pro Cys Pro
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Synthetic modified hinge region(U8-HC5)

<400> SEQUENCE: 104

Glu Lys Cys Asp Lys Thr His Thr Cys Pro Pro Cys Pro
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic human hinge region

<400> SEQUENCE: 105

Glu Pro Lys Ser Cys Asp Lys Thr His Thr Cys Pro Pro Cys Pro
1               5                   10                  15

<210> SEQ ID NO 106
<211> LENGTH: 17
<212> TYPE: PRT
<213> ORGANISM: Artificial Sequence
<220> FEATURE:
<223> OTHER INFORMATION: Synthetic CDR-L1 of antibody L3-11Y

<400> SEQUENCE: 106

Lys Ser Ser Gln Ser Leu Leu Ala Trp Gly Asn Gln Asn Tyr Leu
1               5                   10                  15

Ala

<210> SEQ ID NO 107
<211> LENGTH: 114
<212> TYPE: PRT
<213> ORGANISM: Artificial Sequence
<220> FEATURE:
<223> OTHER INFORMATION: Synthetic amino acid sequence of light chain
      variable region of antibody L3-11Y

<400> SEQUENCE: 107

Asp Ile Gln Met Thr Gln Ser Pro Ser Ser Leu Ser Ala Ser Val Gly
1               5                   10                  15
```

```
Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
             85                  90                  95

Ser Tyr Ser Arg Pro Tyr Thr Phe Gly Gln Gly Thr Lys Val Glu Ile
            100                 105                 110

Lys Arg

<210> SEQ ID NO 108
<211> LENGTH: 220
<212> TYPE: PRT
<213> ORGANISM: Artificial Sequence
<220> FEATURE:
<223> OTHER INFORMATION: Synthetic amino acid sequence of light chain of
      antibody L3-11Y

<400> SEQUENCE: 108

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Trp
             20                  25                  30

Gly Asn Gln Asn Asn Tyr Leu Ala Trp Tyr Gln Gln Lys Pro Gly Lys
         35                  40                  45

Ala Pro Lys Met Leu Ile Ile Trp Ala Ser Thr Arg Val Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
             85                  90                  95

Ser Tyr Ser Arg Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 109
<211> LENGTH: 5
<212> TYPE: PRT
<213> ORGANISM: Artificial Sequence
<220> FEATURE:
```

```
<223> OTHER INFORMATION: Synthetic polypeptide for CDR-H1 of an
      anti-VEGF antibody

<400> SEQUENCE: 109

Gly Tyr Ala Met Ser
 1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic polypeptide for CDR-H1 of an
      anti-VEGF antibody

<400> SEQUENCE: 110

Asp Tyr Ala Met Ser
 1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic polypeptide for CDR-H1 of an
      anti-VEGF antibody

<400> SEQUENCE: 111

Asn Tyr Asp Met Ser
 1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic polypeptide for CDR-H1 of an
      anti-VEGF antibody

<400> SEQUENCE: 112

Asp Tyr Tyr Met Ser
 1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic polypeptide for CDR-H1 of an
      anti-VEGF antibody

<400> SEQUENCE: 113

Ser Tyr Ser Met Ser
 1               5

<210> SEQ ID NO 114
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 114

Ser Ile Tyr Ser Ser Gly Ser Lys Tyr Tyr Ala Asp Ser Val Lys
 1               5                  10                  15

Gly
```

```
<210> SEQ ID NO 115
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 115

Ser Ile Tyr Pro Gly Ser Gly Ser Lys Tyr Tyr Ala Asp Ser Val Lys
 1               5                  10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 116

Gly Ile Tyr Pro Asn Gly Gly Ser Lys Tyr Tyr Ala Asp Ser Val Lys
 1               5                  10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 117

Ala Ile Tyr Ser Gly Gly Gly Ser Ile Tyr Tyr Ala Asp Ser Val Lys
 1               5                  10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 118

Gly Ile Ser His Gly Gly Gly Asn Lys Tyr Tyr Ala Asp Ser Val Lys
 1               5                  10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 119

Leu Ile Ser His Gly Gly Gly Asn Ile Tyr Tyr Ala Asp Ser Val Lys
 1               5                  10                  15
```

Gly

<210> SEQ ID NO 120
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 120

Gly Ile Ser His Asp Gly Gly Asn Thr Tyr Tyr Ala Asp Ser Val Lys
 1               5                  10                  15

Gly

<210> SEQ ID NO 121
<211> LENGTH: 17
<212> TYPE: PRT
<213> ORGANISM: Artificial Sequence
<220> FEATURE:
<223> OTHER INFORMATION: Synthetic polypeptide for CDR-H2 of an
      anti-VEGF antibody

<400> SEQUENCE: 121

Trp Ile Tyr Pro Gly Asp Ser Ser Ile Tyr Tyr Ala Asp Ser Val Lys
 1               5                  10                  15

Gly

<210> SEQ ID NO 122
<211> LENGTH: 18
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 122

Ala Ser Ser Thr Cys Thr Arg Thr Trp Cys Ser Tyr Asp Asp Ala Met
 1               5                  10                  15

Asp Val

<210> SEQ ID NO 123
<211> LENGTH: 12
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 123

Asp Ala Trp Phe Arg Gly His Asn Val Phe Asp Tyr
 1               5                  10

<210> SEQ ID NO 124
<211> LENGTH: 18
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 124

Ala Leu Arg Gln Cys Gln Arg Tyr Trp Cys Ser Tyr Ala Asp Gly Met
 1               5                  10                  15

Asp Val

<210> SEQ ID NO 125
<211> LENGTH: 12
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 125

Asp Val Gln Trp Asn Lys Ala Pro Arg Phe Asp Tyr
 1               5                  10

<210> SEQ ID NO 126
<211> LENGTH: 12
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 126

Asp Leu Arg Ala Asn Asn Asp Thr Gly Phe Asp Tyr
 1               5                  10

<210> SEQ ID NO 127
<211> LENGTH: 18
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 127

Val Pro Val Met Cys Thr Asn His Trp Cys Ser Tyr Ala Asn Gly Met
 1               5                  10                  15

Asp Val

<210> SEQ ID NO 128
<211> LENGTH: 12
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 128

Asp Arg Arg Lys Gly Pro Ser Thr Glu Phe Asp Tyr
 1               5                  10

<210> SEQ ID NO 129
<211> LENGTH: 18
<212> TYPE: PRT
<213> ORGANISM: Artificial Sequence
<220> FEATURE:
<223> OTHER INFORMATION: Synthetic polypeptide for CDR-H3 of an
      anti-VEGF antibody

<400> SEQUENCE: 129

Leu Leu Ser Ile Asp Gln Ala Gln Leu His Tyr Tyr Tyr Asp Ala Met
 1               5                  10                  15

Asp Val

<210> SEQ ID NO 130
<211> LENGTH: 13
<212> TYPE: PRT

```
<213> ORGANISM: Artificial Sequence
<220> FEATURE:
<223> OTHER INFORMATION: Synthetic polypeptide for CDR-L1 of an
      anti-VEGF antibody

<400> SEQUENCE: 130

Thr Gly Ser Ser Ser Asn Ile Gly Asn Asn Ala Val Thr
 1               5                  10

<210> SEQ ID NO 131
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 131

Thr Gly Ser Ser Ser Asn Ile Gly Ser Asn Asn Val Thr
 1               5                  10

<210> SEQ ID NO 132
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 132

Thr Gly Ser Ser Ser Asn Ile Gly Ser Asn Tyr Val Ser
 1               5                  10

<210> SEQ ID NO 133
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 133

Ser Gly Ser Ser Ser Asn Ile Gly Ser Asn Asp Val Ser
 1               5                  10

<210> SEQ ID NO 134
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 134

Thr Gly Ser Ser Ser Asn Ile Gly Ser Asn Ala Val Thr
 1               5                  10

<210> SEQ ID NO 135
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 135

Ser Ala Ser Ser Ser Asn Ile Gly Ser Asn Ala Val Tyr
 1               5                  10
```

<210> SEQ ID NO 136
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 136

Thr Gly Ser Ser Ser Asn Ile Gly Ser Asn Ser Val Ser
 1               5                  10

<210> SEQ ID NO 137
<211> LENGTH: 13
<212> TYPE: PRT
<213> ORGANISM: Artificial Sequence
<220> FEATURE:
<223> OTHER INFORMATION: Synthetic polypeptide for CDR-L1 of an
      anti-VEGF antibody

<400> SEQUENCE: 137

Thr Gly Ser Ser Ser Asn Ile Gly Asn Tyr Tyr Val Tyr
 1               5                  10

<210> SEQ ID NO 138
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 138

Asp Asp Ser His Arg Pro Ser
 1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 139

Ser Asp Ser His Arg Pro Ser
 1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 140

Ala Asp Ser Gln Arg Pro Ser
 1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 141

Ala Asp Ser Asn Arg Pro Ser
 1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 142

Asp Asp Asn His Arg Pro Ser
 1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 143

Ser Asp Asn Gln Arg Pro Ser
 1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 144

Asp Asp Asn Asn Arg Pro Ser
 1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic polypeptide for CDR-L2 of an
      anti-VEGF antibody

<400> SEQUENCE: 145

Ala Asn Ser His Arg Pro Ser
 1               5

<210> SEQ ID NO 146
<211> LENGTH: 11
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 146

Gly Thr Trp Asp Tyr Ser Leu Ser Gly Tyr Val
 1               5                   10

<210> SEQ ID NO 147
<211> LENGTH: 11

```
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 147

Gly Ser Trp Asp Tyr Ser Leu Ser Ala Tyr Val
 1               5                  10

<210> SEQ ID NO 148
<211> LENGTH: 11
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 148

Gly Ser Trp Asp Tyr Ser Leu Ser Gly Tyr Val
 1               5                  10

<210> SEQ ID NO 149
<211> LENGTH: 11
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 149

Gly Ala Trp Asp Tyr Ser Leu Asn Ala Tyr Val
 1               5                  10

<210> SEQ ID NO 150
<211> LENGTH: 11
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 150

Gly Ala Trp Asp Tyr Ser Leu Ser Ala Tyr Val
 1               5                  10

<210> SEQ ID NO 151
<211> LENGTH: 11
<212> TYPE: PRT
<213> ORGANISM: Artificial Sequence
<220> FEATURE:
<223> OTHER INFORMATION: Synthetic polypeptide for CDR-L3 of an
      anti-VEGF antibody

<400> SEQUENCE: 151

Gly Ser Trp Asp Asp Ser Leu Ser Ala Tyr Val
 1               5                  10

<210> SEQ ID NO 152
<211> LENGTH: 127
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 152

Glu Val Gln Leu Leu Glu Ser Gly Gly Gly Leu Val Gln Pro Gly Gly
```

```
                1               5                      10                     15
            Ser Leu Arg Leu Ser Cys Ala Ala Ser Gly Phe Thr Phe Ser Gly Tyr
                           20                     25                     30

Ala Met Ser Trp Val Arg Gln Ala Pro Gly Lys Gly Leu Glu Trp Val
                           35                     40                     45

Ser Ser Ile Tyr Ser Ser Gly Ser Lys Tyr Tyr Ala Asp Ser Val
                           50                     55                     60

Lys Gly Arg Phe Thr Ile Ser Arg Asp Asn Ser Lys Asn Thr Leu Tyr
             65                    70                     75                     80

Leu Gln Met Asn Ser Leu Arg Ala Glu Asp Thr Ala Val Tyr Tyr Cys
                           85                     90                     95

Ala Arg Ala Ser Ser Thr Cys Thr Arg Thr Trp Cys Ser Tyr Asp Asp
                           100                    105                    110

Ala Met Asp Val Trp Gly Gln Gly Thr Leu Val Thr Val Ser Ser
                           115                    120                    125
```

<210> SEQ ID NO 153
<211> LENGTH: 121
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 153

```
            Glu Val Gln Leu Leu Glu Ser Gly Gly Gly Leu Val Gln Thr Gly Gly
             1               5                      10                     15

Ser Leu Arg Leu Ser Cys Ala Ala Ser Gly Phe Thr Phe Ser Asp Tyr
                           20                     25                     30

Ala Met Ser Trp Val Arg Gln Ala Pro Gly Lys Gly Leu Glu Trp Val
                           35                     40                     45

Ser Ser Ile Tyr Pro Gly Ser Gly Ser Lys Tyr Tyr Ala Asp Ser Val
                           50                     55                     60

Lys Gly Arg Phe Ala Ile Ser Arg Asp Asn Ser Lys Asn Thr Leu Tyr
             65                    70                     75                     80

Leu Gln Met Asn Ser Leu Arg Ala Glu Asp Thr Ala Val Tyr Tyr Cys
                           85                     90                     95

Ala Arg Asp Ala Trp Phe Arg Gly His Asn Val Phe Asp Tyr Trp Gly
                           100                    105                    110

Gln Gly Thr Leu Val Thr Val Ser Ser
                           115                    120
```

<210> SEQ ID NO 154
<211> LENGTH: 127
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 154

```
            Glu Val Gln Leu Leu Glu Ser Gly Gly Gly Leu Val Gln Pro Gly Gly
             1               5                      10                     15

Ser Leu Arg Leu Ser Cys Ala Ala Ser Gly Phe Thr Phe Ser Asn Tyr
                           20                     25                     30

Asp Met Ser Trp Val Arg Gln Ala Pro Gly Lys Gly Leu Glu Trp Val
                           35                     40                     45

Ser Gly Ile Tyr Pro Asn Gly Gly Ser Lys Tyr Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Ala Leu Arg Gln Cys Gln Arg Tyr Trp Cys Ser Tyr Ala Asp
            100                 105                 110

Gly Met Asp Val Trp Gly Gln Gly Thr Leu Val Thr Val Ser Ser
        115                 120                 125
```

<210> SEQ ID NO 155
<211> LENGTH: 121
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 155

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Tyr
                20                  25                  30

Tyr Met Ser Trp Val Arg Gln Ala Pro Gly Lys Gly Leu Glu Trp Val
            35                  40                  45

Ser Ala Ile Tyr Ser Gly Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Val Gln Trp Asn Lys Ala Pro Arg Phe Asp Tyr Trp Gly
            100                 105                 110

Gln Gly Thr Leu Val Thr Val Ser Ser
        115                 120
```

<210> SEQ ID NO 156
<211> LENGTH: 121
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 156

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                20                  25                  30

Ser Met Ser Trp Val Arg Gln Ala Pro Gly Lys Gly Leu Glu Trp Val
            35                  40                  45

Ser Gly Ile Ser His Gly Gly Gly Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Arg Ala Asn Asn Asp Thr Gly Phe Asp Tyr Trp Gly
```

Gln Gly Thr Leu Val Thr Val Ser Ser
        115                 120

<210> SEQ ID NO 157
<211> LENGTH: 127
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 157

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Asp Met Ser Trp Val Arg Gln Ala Pro Gly Lys Gly Leu Glu Trp Val
         35                  40                  45

Ser Leu Ile Ser His Gly Gly Gly Asn Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Pro Val Met Cys Thr Asn His Trp Cys Ser Tyr Ala Asn
            100                 105                 110

Gly Met Asp Val Trp Gly Gln Gly Thr Leu Val Thr Val Ser Ser
        115                 120                 125

<210> SEQ ID NO 158
<211> LENGTH: 121
<212> TYPE: PRT
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 158

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Ala Met Ser Trp Val Arg Gln Ala Pro Gly Lys Gly Leu Glu Trp Val
         35                  40                  45

Ser Gly Ile Ser His Asp Gly Gly Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Arg Lys Gly Pro Ser Thr Glu Phe Asp Tyr Trp Gly
            100                 105                 110

Gln Gly Thr Leu Val Thr Val Ser Ser
        115                 120

<210> SEQ ID NO 159
<211> LENGTH: 127
<212> TYPE: PRT

```
<213> ORGANISM: Artificial Sequence
<220> FEATURE:
<223> OTHER INFORMATION: Synthetic polypeptide for heavy chain variable
      region of an anti-VEGF antibody

<400> SEQUENCE: 159

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Trp Ile Tyr Pro Gly Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Leu Ser Ile Asp Gln Ala Gln Leu His Tyr Tyr Tyr Asp
            100                 105                 110

Ala Met Asp Val Trp Gly Gln Gly Thr Leu Val Thr Val Ser Ser
        115                 120                 125

<210> SEQ ID NO 160
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 160

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Asn
            20                  25                  30

Ala Val Thr Trp Tyr Gln Gln Leu Pro Gly Thr Ala Pro Lys Leu Leu
        35                  40                  45

Ile Tyr Asp Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Thr Trp Asp Tyr Ser Leu
                85                  90                  95

Ser Gly Tyr Val Phe Gly Gly Gly Thr Lys Leu Thr Val Leu Gly
            100                 105                 110

<210> SEQ ID NO 161
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 161

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ser Asn
            20                  25                  30
```

```
Asn Val Thr Trp Tyr Gln Gln Leu Pro Gly Thr Ala Pro Lys Leu Leu
            35                  40                  45

Ile Tyr Ser Asp Ser His Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gly Ser Trp Asp Tyr Ser Leu
                 85                  90                  95

Ser Ala Tyr Val Phe Gly Gly Gly Thr Lys Leu Thr Val Leu Gly
                100                 105                 110

<210> SEQ ID NO 162
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 162

Gln Ser Val Leu Thr Gln Pro Pro Ser Ala Ser Gly Thr Pro Gly Gln
 1               5                  10                  15

Arg Val Thr Ile Ser Cys Thr Gly Ser Ser Ser Asn Ile Gly Ser Asn
             20                  25                  30

Tyr Val Ser Trp Tyr Gln Gln Leu Pro Gly Thr Ala Pro Lys Leu Leu
            35                  40                  45

Ile Tyr Ala Asp Ser Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Thr Trp Asp Tyr Ser Leu
                 85                  90                  95

Ser Gly Tyr Val Leu Gly Gly Gly Thr Lys Leu Thr Val Leu Gly
                100                 105                 110

<210> SEQ ID NO 163
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 163

Gln Ser Val Leu Thr Gln Pro Pro Ser Ala Ser Gly Ala Pro Gly Gln
 1               5                  10                  15

Arg Val Thr Ile Ser Cys Ser Gly Ser Ser Ser Asn Ile Gly Ser Asn
             20                  25                  30

Asp Val Ser Trp Tyr Gln Gln Leu Pro Gly Thr Ala Pro Lys Leu Leu
            35                  40                  45

Ile Tyr Ala Asp Ser Asn Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gly Ser Trp Asp Tyr Ser Leu
                 85                  90                  95

Ser Gly Tyr Val Phe Gly Gly Gly Thr Lys Leu Thr Val Leu Gly
                100                 105                 110
```

<210> SEQ ID NO 164
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 164

Gln Ser Val Leu Thr Gln Pro Pro Ser Ser Gly Thr Pro Gly Gln
 1               5                  10                  15

Arg Val Thr Ile Ser Cys Thr Gly Ser Ser Ser Asn Ile Gly Ser Asn
            20                  25                  30

Ala Val Thr Trp Tyr Gln Gln Leu Pro Gly Thr Ala Pro Lys Leu Leu
        35                  40                  45

Ile Tyr Asp Asp Asn His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Asn Ala Tyr Val Phe Gly Gly Gly Thr Lys Leu Thr Val Leu Gly
            100                 105                 110

<210> SEQ ID NO 165
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 165

Gln Ser Val Leu Thr Gln Pro Pro Ser Ala Ser Gly Thr Pro Gly Gln
 1               5                  10                  15

Arg Val Ile Ile Ser Cys Ser Ala Ser Ser Ser Asn Ile Gly Ser Asn
            20                  25                  30

Ala Val Tyr Trp Tyr Gln Gln Leu Pro Gly Thr Ala Pro Lys Leu Leu
        35                  40                  45

Ile Tyr Ser Asp Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Tyr Ser Leu
                85                  90                  95

Ser Ala Tyr Val Phe Gly Gly Gly Thr Lys Leu Thr Val Leu Gly
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 166

Gln Ser Val Leu Thr Gln Pro Pro Ser Leu Ser Gly Thr Pro Gly Gln
 1               5                  10                  15

Arg Val Thr Ile Ser Cys Thr Gly Ser Ser Asn Ile Gly Ser Asn
            20                  25                  30

Ser Val Ser Trp Tyr Gln Gln Leu Pro Gly Thr Ala Pro Lys Leu Leu
        35                  40                  45

Ile Tyr Asp Asp Asn Asn Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ala Trp Asp Tyr Ser Leu
                85                  90                  95

Ser Ala Tyr Val Phe Gly Gly Gly Thr Lys Leu Thr Val Leu Gly
            100                 105                 110

<210> SEQ ID NO 167
<211> LENGTH: 111
<212> TYPE: PRT
<213> ORGANISM: Artificial Sequence
<220> FEATURE:
<223> OTHER INFORMATION: Synthetic polypeptide for light chain variable
      region of an anti-VEGF antibody

<400> SEQUENCE: 167

Gln Ser Val Leu Thr Gln Pro Pro Ser Pro Ser Gly Thr Pro Gly Gln
1               5                   10                  15

Arg Val Thr Ile Ser Cys Thr Gly Ser Ser Ser Asn Ile Gly Asn Tyr
            20                  25                  30

Tyr Val Tyr Trp Tyr Gln Gln Leu Pro Gly Thr Ala Pro Lys Leu Leu
        35                  40                  45

Ile Tyr Ala Asn Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gly Ser Trp Asp Asp Ser Leu
                85                  90                  95

Ser Ala Tyr Val Phe Gly Gly Gly Thr Lys Leu Thr Val Leu Gly
            100                 105                 110

<210> SEQ ID NO 168
<211> LENGTH: 253
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ser Ile Tyr Ser Ser Gly Ser Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Ser Thr Cys Thr Arg Thr Trp Cys Ser Tyr Asp Asp

```
          100                 105                 110
Ala Met Asp Val Trp Gly Gln Gly Thr Leu Val Thr Val Ser Ser Gly
            115                 120                 125

Gly Gly Gly Ser Gly Gly Gly Ser Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Thr Gly Ser Ser Asn Ile Gly Asn Asn Ala Val
                165                 170                 175

Thr Trp Tyr Gln Gln Leu Pro Gly Thr Ala Pro Lys Leu Leu Ile Tyr
            180                 185                 190

Asp Asp Ser His Arg Pro Ser Gly Val Pro Asp Arg Phe Ser Gly Ser
                195                 200                 205

Lys Ser Gly Thr Ser Ala Ser Leu Ala Ile Ser Gly Leu Arg Ser Glu
            210                 215                 220

Asp Glu Ala Asp Tyr Tyr Cys Gly Thr Trp Asp Tyr Ser Leu Ser Gly
225                 230                 235                 240

Tyr Val Phe Gly Gly Gly Thr Lys Leu Thr Val Leu Gly
                245                 250

<210> SEQ ID NO 169
<211> LENGTH: 247
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 169

Glu Val Gln Leu Leu Glu Ser Gly Gly Gly Leu Val Gln Thr Gly Gly
1               5                   10                  15

Ser Leu Arg Leu Ser Cys Ala Ala Ser Gly Phe Thr Phe Ser Asp Tyr
                20                  25                  30

Ala Met Ser Trp Val Arg Gln Ala Pro Gly Lys Gly Leu Glu Trp Val
            35                  40                  45

Ser Ser Ile Tyr Pro Gly Ser Gly Ser Lys Tyr Tyr Ala Asp Ser Val
        50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Trp Phe Arg Gly His Asn Val Phe Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Gly Ser Gln Ser Val Leu Thr Gln Pro Pro
    130                 135                 140

Ser Ala Ser Gly Thr Pro Gly Gln Arg Val Thr Ile Ser Cys Thr Gly
145                 150                 155                 160

Ser Ser Ser Asn Ile Gly Ser Asn Asn Val Thr Trp Tyr Gln Gln Leu
                165                 170                 175

Pro Gly Thr Ala Pro Lys Leu Leu Ile Tyr Ser Asp Ser His Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Gln Ser Glu Asp Glu Ala Asp Tyr Tyr
```

```
                      210                 215                 220
Cys Gly Ser Trp Asp Tyr Ser Leu Ser Ala Tyr Val Phe Gly Gly Gly
225                 230                 235                 240

Thr Lys Leu Thr Val Leu Gly
                245

<210> SEQ ID NO 170
<211> LENGTH: 253
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Asp Met Ser Trp Val Arg Gln Ala Pro Gly Lys Gly Leu Glu Trp Val
        35                  40                  45

Ser Gly Ile Tyr Pro Asn Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Arg Gln Cys Gln Arg Tyr Trp Cys Ser Tyr Ala Asp
            100                 105                 110

Gly Met Asp Val Trp Gly Gln Gly Thr Leu Val Thr Val Ser Ser Gly
        115                 120                 125

Gly Gly Gly Ser Gly Gly Gly Ser Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Thr Gly Ser Ser Ser Asn Ile Gly Ser Asn Tyr Val
                165                 170                 175

Ser Trp Tyr Gln Gln Leu Pro Gly Thr Ala Pro Lys Leu Leu Ile Tyr
            180                 185                 190

Ala Asp Ser Gln Arg Pro Ser Gly Val Pro Asp Arg Phe Ser Gly Ser
        195                 200                 205

Lys Ser Gly Thr Ser Ala Ser Leu Ala Ile Ser Gly Leu Arg Ser Glu
    210                 215                 220

Asp Glu Ala Asp Tyr Tyr Cys Gly Thr Trp Asp Tyr Ser Leu Ser Gly
225                 230                 235                 240

Tyr Val Leu Gly Gly Gly Thr Lys Leu Thr Val Leu Gly
                245                 250

<210> SEQ ID NO 171
<211> LENGTH: 247
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 171

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Asp Tyr
                20                  25                  30

Tyr Met Ser Trp Val Arg Gln Ala Pro Gly Lys Gly Leu Glu Trp Val
            35                  40                  45

Ser Ala Ile Tyr Ser Gly Gly Gly Ser Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Gln Trp Asn Lys Ala Pro Arg Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
130                 135                 140

Ser Ala Ser Gly Ala Pro Gly Gln Arg Val Thr Ile Ser Cys Ser Gly
145                 150                 155                 160

Ser Ser Ser Asn Ile Gly Ser Asn Asp Val Ser Trp Tyr Gln Gln Leu
                165                 170                 175

Pro Gly Thr Ala Pro Lys Leu Leu Ile Tyr Ala Asp Ser Asn Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
210                 215                 220

Cys Gly Ser Trp Asp Tyr Ser Leu Ser Gly Tyr Val Phe Gly Gly
225                 230                 235                 240

Thr Lys Leu Thr Val Leu Gly
                245

<210> SEQ ID NO 172
<211> LENGTH: 247
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Ser Trp Val Arg Gln Ala Pro Gly Lys Gly Leu Glu Trp Val
            35                  40                  45

Ser Gly Ile Ser His Gly Gly Gly Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Arg Ala Asn Asn Asp Thr Gly Phe Asp Tyr Trp Gly
            100                 105                 110

Gln Gly Thr Leu Val Thr Val Ser Ser Gly Gly Gly Gly Ser Gly Gly
        115                 120                 125

```
Gly Gly Ser Gly Gly Gly Thr Gln Ser Val Leu Thr Gln Pro Pro
    130             135                 140
Ser Ser Ser Gly Thr Pro Gly Gln Arg Val Thr Ile Ser Cys Thr Gly
145             150                 155                 160
Ser Ser Ser Asn Ile Gly Ser Asn Ala Val Thr Trp Tyr Gln Gln Leu
                165                 170                 175
Pro Gly Thr Ala Pro Lys Leu Leu Ile Tyr Asp Asp Asn His Arg Pro
            180                 185                 190
Ser Gly Val Pro Asp Arg Phe Ser Gly Ser Lys Ser Gly Thr Ser Ala
        195                 200                 205
Ser Leu Ala Ile Ser Gly Leu Arg Ser Glu Asp Glu Ala Asp Tyr Tyr
    210                 215                 220
Cys Gly Ala Trp Asp Tyr Ser Leu Asn Ala Tyr Val Phe Gly Gly Gly
225             230                 235                 240
Thr Lys Leu Thr Val Leu Gly
            245
```

<210> SEQ ID NO 173
<211> LENGTH: 253
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 173

```
Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Ser Asn Tyr
             20                  25                  30
Asp Met Ser Trp Val Arg Gln Ala Pro Gly Lys Gly Leu Glu Trp Val
         35                  40                  45
Ser Leu Ile Ser His Gly Gly Gly Asn Ile Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Val Pro Val Met Cys Thr Asn His Trp Cys Ser Tyr Ala Asn
            100                 105                 110
Gly Met Asp Val Trp Gly Gln Gly Thr Leu Val Thr Val Ser Ser Gly
        115                 120                 125
Gly Gly Gly Ser Gly Gly Gly Ser Gly Gly Gly Gly Ser Gln Ser
    130                 135                 140
Val Leu Thr Gln Pro Pro Ser Ala Ser Gly Thr Pro Gly Gln Arg Val
145                 150                 155                 160
Ile Ile Ser Cys Ser Ala Ser Ser Asn Ile Gly Ser Asn Ala Val
                165                 170                 175
Tyr Trp Tyr Gln Gln Leu Pro Gly Thr Ala Pro Lys Leu Leu Ile Tyr
            180                 185                 190
Ser Asp Asn Gln Arg Pro Ser Gly Val Pro Asp Arg Phe Ser Gly Ser
        195                 200                 205
Lys Ser Gly Thr Ser Ala Ser Leu Ala Ile Ser Gly Leu Arg Ser Glu
    210                 215                 220
Asp Glu Ala Asp Tyr Tyr Cys Gly Ser Trp Asp Tyr Ser Leu Ser Ala
225                 230                 235                 240
```

Tyr Val Phe Gly Gly Gly Thr Lys Leu Thr Val Leu Gly
            245                 250

<210> SEQ ID NO 174
<211> LENGTH: 247
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 174

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Gly Ile Ser His Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Lys Gly Pro Ser Thr Glu Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gln Ser Val Leu Thr Gln Pro Pro
    130                 135                 140

Ser Leu Ser Gly Thr Pro Gly Gln Arg Val Thr Ile Ser Cys Thr Gly
145                 150                 155                 160

Ser Ser Ser Asn Ile Gly Ser Asn Ser Val Ser Trp Tyr Gln Gln Leu
                165                 170                 175

Pro Gly Thr Ala Pro Lys Leu Leu Ile Tyr Asp Asp Asn Asn Arg Pro
            180                 185                 190

Ser Gly Val Pro Asp Arg Phe Ser Gly Ser Lys Ser Gly Thr Ser Ala
        195                 200                 205

Ser Leu Ala Ile Ser Gly Leu Arg Ser Glu Asp Glu Ala Asp Tyr Tyr
    210                 215                 220

Cys Gly Ala Trp Asp Tyr Ser Leu Ser Ala Tyr Val Phe Gly Gly Gly
225                 230                 235                 240

Thr Lys Leu Thr Val Leu Gly
            245

<210> SEQ ID NO 175
<211> LENGTH: 253
<212> TYPE: PRT
<213> ORGANISM: Artificial Sequence
<220> FEATURE:
<223> OTHER INFORMATION: Synthetic polypeptide for an anti-VEGF scFv

<400> SEQUENCE: 175

Glu Val Gln Leu Leu Glu Ser Gly Gly Gly Leu Val Gln Thr Gly Gly
 1               5                  10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

```
Ser Trp Ile Tyr Pro Gly Asp Ser Ser Ile Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Leu Leu Ser Ile Asp Gln Ala Gln Leu His Tyr Tyr Tyr Asp
            100                 105                 110
Ala Met Asp Val Trp Gly Gln Gly Thr Leu Val Thr Val Ser Ser Gly
        115                 120                 125
Gly Gly Gly Ser Gly Gly Gly Ser Gly Gly Gly Ser Gln Ser
130                 135                 140
Val Leu Thr Gln Pro Pro Ser Pro Ser Gly Thr Pro Gly Gln Arg Val
145                 150                 155                 160
Thr Ile Ser Cys Thr Gly Ser Ser Ser Asn Ile Gly Asn Tyr Tyr Val
                165                 170                 175
Tyr Trp Tyr Gln Gln Leu Pro Gly Thr Ala Pro Lys Leu Leu Ile Tyr
            180                 185                 190
Ala Asn Ser His Arg Pro Ser Gly Val Pro Asp Arg Phe Ser Gly Ser
        195                 200                 205
Lys Ser Gly Thr Ser Ala Ser Leu Ala Ile Ser Gly Leu Arg Ser Glu
    210                 215                 220
Asp Glu Ala Asp Tyr Tyr Cys Gly Ser Trp Asp Asp Ser Leu Ser Ala
225                 230                 235                 240
Tyr Val Phe Gly Gly Gly Thr Lys Leu Thr Val Leu Gly
                245                 250

<210> SEQ ID NO 176
<211> LENGTH: 759
<212> TYPE: DNA
<213> ORGANISM: Artificial Sequence
<220> FEATURE:
<223> OTHER INFORMATION: Synthetic polynucleotide encoding an anti-VEGF
      scFv (SEQ ID NO: 168)

<400> SEQUENCE: 176
gaggtgcagc tgttggagtc tgggggaggc ttggtacagc ctgggggtc cctgagactc       60 tcctgtgcag cctctggatt caccttagc ggttatgcta tgagctgggt ccgccaggct     120
ccagggaagg gctggagtg gtctcatcg atctattcta gtagtggtag taaatattac      180
gctgattctg taaaaggtcg gttcaccatc tccagagaca attccaagaa cacgctgtat    240
ctgcaaatga acagcctgag agccgaggac acggccgtgt attactgtgc gagagctagt    300
agtacgtgta cgcggacgtg gtgttcttat gatgatgcta tggacgtctg gggccagggt    360
acactggtca ccgtgagctc aggtggaggc ggttcaggcg aggtggatc cggcggtggc    420 ggatcgcagt ctgtgctgac tcagccaccc tcagcgtctg gaccccggg cagagggtc     480 accatctctt gtactggctc ttcatctaat attggcaata atgctgtcac ctggtaccag   540
cagctcccag gaacggcccc caaactcctc atctatgatg atagtcatcg gccaagcggg   600
gtccctgacc gattctctgg ctccaagtct ggcacctcag cctccctggc catcagtggg    660
ctccggtccg aggatgaggc tgattattac tgtggtactt gggattatag cctgagtggt    720
tatgtcttcg gcggaggcac caagctgacg gtcctaggc                          759

<210> SEQ ID NO 177
```

```
<211> LENGTH: 741
<212> TYPE: DNA
<213> ORGANISM: Artificial Sequence
<220> FEATURE:
<223> OTHER INFORMATION: Synthetic polynucleotide encoding an anti-VEGF
      scFv (SEQ ID NO: 169)

<400> SEQUENCE: 177
gaggtgcagc tgttggagtc tgggggaggc ttggtacaga ctgggggtc cctgagactc      60
tcctgtgcag cctctggatt cacctttagc gattatgcta tgagctgggt ccgccaggct    120
ccagggaagg gctggagtg gtctcatcg atctatcctg gtagtggtag taaatattac     180
gctgattctg taaaaggtcg gttcgccatc tccagagaca attccaagaa cacgctgtat   240
ctgcaaatga acagcctgag agccgaggac acggccgtgt attactgtgc gagagatgct   300
tggtttcggg gtcataatgt tttcgactac tggggccagg gtacactggt caccgtgagc   360
tcaggtggag gcggttcagg cggaggtgga tccggcggtg gcggatcgca gtctgtgctg   420
actcagccac cctcagcgtc tgggaccccc gggcagaggg tcaccatctc ttgtactggc   480
tcttcatcta atattggcag taataatgtc acctggtacc agcagctccc aggaacggcc   540
cccaaactcc tcatctattc tgatagtcat cggccaagcg gggtccctga ccgattctct   600
ggctccaagt ctggcacctc agcctccctg gccatcagtg gctccagtc cgaggatgag    660
gctgattatt actgtggttc ttgggattat agcctgagtg cttatgtctt cggcggaggc   720
accaagctga cggtcctagg c                                              741

<210> SEQ ID NO 178
<211> LENGTH: 759
<212> TYPE: DNA
<213> ORGANISM: Artificial Sequence
<220> FEATURE:
<223> OTHER INFORMATION: Synthetic polynucleotide encoding an anti-VEGF
      scFv (SEQ ID NO: 170)

<400> SEQUENCE: 178
gaggtgcagc tgttggagtc tgggggaggc ttggtacagc ctgggggtc cctgagactc     60
tcctgtgcag cctccggatt cacctttagc aattatgata tgagctgggt ccgccaggct   120
ccagggaagg gctggagtg gtctcagggg atctatccta tggtggtag taaatattac    180
gctgattctg taaaaggtcg gttcaccatc tccagagaca attccaagaa cacgctgtat   240
ctgcaaatga acagcctgag agccgaggac acggccgtgt attactgtgc gagagctctt   300
cgtcagtgtc agcgttattg gtgttcttat gctgatggta tggacgtctg gggccagggt   360
acactggtca ccgtgagctc aggtggaggc ggttcaggcg gaggtggatc cggcggtggc   420
ggatcgcagt ctgtgctgac tcagccaccc tcagcgtctg gaccccccgg gcagaggggtc  480
accatctctt gtactggctc ttcatctaat attggcagta attatgtctc ctggtaccag   540
cagctcccag gaacggcccc caaactcctc atctatgctg atagtcagcg gccaagcggg   600
gtccctgacc gattctctgg ctccaagtct ggcacctcag cctccctggc catcagtggg   660
ctccggtccg aggacgaggc tgattattac tgtggtactt gggattatag cctgagtggt   720
tatgtcttag gcggaggcac caagctgacg gtcctaggc                          759

<210> SEQ ID NO 179
<211> LENGTH: 741
<212> TYPE: DNA
<213> ORGANISM: Artificial Sequence
<220> FEATURE:
<223> OTHER INFORMATION: Synthetic polynucleotide encoding an anti-VEGF
``` scFv (SEQ ID NO: 171)

<400> SEQUENCE: 179

```
gaggtgcagc tgttggagtc tgggggaggc ttggtacagc ctggggggtc cctgagactc    60
tcctgtgcag cctctggatt caccttagc gattattata tgagctgggt ccgccaggct    120
ccagggaagg ggctggagtg ggtctcagcg atctattctg gtggtggtag tatatattac   180
gctgattctg taaaaggtcg gttcaccatc tccagagaca attccaagaa cacgctgtat   240
ctgcaaatga acagcctgag agccgaggac acggccgtgt attactgtgc gagagatgtt   300
cagtggaata aggctcctcg tttcgactac tggggccagg gtacactggt caccgtgagc   360
tcaggtggag gcggttcagg cggaggtgga tccggcggtg gcggatcgca gtctgtgctg   420
actcagccac cctcagcgtc tggggccccc gggcagaggg tcaccatctc ttgtagtggc   480
tcttcatcta atattggcag taatgatgtc tcctggtacc agcagctccc aggaacggcc   540
cccaagctcc tcatctatgc tgatagtaat cggccaagcg ggtccctga  ccgattctct   600
ggctccaagt ctggcacctc agcctccctg gccatcagtg gctccggtc  cgaggatgag   660
gctgattatt actgtggttc ttgggattat agcctgagtg gttatgtctt cggcggaggt   720
accaagctga cggtcctagg c                                             741
```

<210> SEQ ID NO 180
<211> LENGTH: 741
<212> TYPE: DNA
<213> ORGANISM: Artificial Sequence
<220> FEATURE:
<223> OTHER INFORMATION: Synthetic polynucleotide encoding an anti-VEGF
     scFv (SEQ ID NO: 172)

<400> SEQUENCE: 180

```
gaggtgcagc tgttggagtc tgggggaggc ttggtacagc ctggggggtc cctgagactc    60
tcctgtgcag cctctggatt caccttagc agttattcta tgagctgggt ccgccaggct    120
ccagggaagg ggctggagtg ggtctcaggg atctctcatg gtggtggtaa taaatattac   180
gctgattctg taaaaggtcg gttcaccatc tccagagaca attccaagaa cacgctgtat   240
ctgcaaatga acagcctgag agccgaggac acggccgtgt attactgtgc gagagatctt   300
agggcgaata atgatacggg tttcgactac tggggccagg gtacactggt caccgtgagc   360
tcaggtggag gcggttcagg cggaggtgga tccggcggtg gcggaacgca gtctgtgctg   420
actcagccac cctcatcgtc tgggaccccc gggcagaggg tcaccatctc ttgtactggc   480
tcttcatcta atattggcag taatgctgtc acctggtacc agcagctccc aggaacggcc   540
cccaaactcc tcatctatga tgataatcat cggccaagcg ggtccctga  ccgattctct   600
ggctccaagt ctggcacctc agcctccctg gccatcagtg gctccggtc  cgaggatgag   660
gctgattatt actgtggtgc ttgggattat agcctgaatg cttatgtctt cggcggaggc   720
accaagctga cggtcctagg c                                             741
```

<210> SEQ ID NO 181
<211> LENGTH: 759
<212> TYPE: DNA
<213> ORGANISM: Artificial Sequence
<220> FEATURE:
<223> OTHER INFORMATION: Synthetic polynucleotide encoding an anti-VEGF
     scFv (SEQ ID NO: 173)

<400> SEQUENCE: 181

```
gaggtgcagc tgttggagtc tgggggaggc ttggtacagc ctggggggtc cctgagactc    60
```

```
tcctgtgcag cctctggatt cacctttagc aattatgata tgagctgggt ccgccaggct    120
ccagggaagg ggctggagtg ggtctcattg atctctcatg gtggtggtaa tatatattac    180
gctgattctg taaaaggtcg gttcaccatc tccagggaca attccaagaa cacgctgtat    240
ctgcaaatga acagcctgag agccgaggac acggccgtgt attactgtgc gagagttcct    300
gttatgtgta ctaatcattg gtgttcttat gctaatggta tggacgtctg gggccagggt    360
acactggtca ccgtgagctc aggtggaggc ggttcaggcg gaggtggatc cggcggtggc    420
ggatcgcagt ctgtgctgac tcagccaccc tcagcgtctg gaccccggg cagagggtc     480 atcatctcct gtagtgcctc ttcatctaat attggcagta atgctgtcta ctggtaccag    540
cagctcccag aacggcccc caaactcctc atctattctg ataatcagcg gccaagcggg    600
gtccctgacc gattctctgg ctccaagtct ggcacctcag cctccctggc catcagtggg    660
ctccggtccg aggatgaggc tgattattac tgtggttctt gggattatag cctgagtgct    720
tatgtcttcg gcggaggcac caagctgacg gtcctaggc                           759
```

<210> SEQ ID NO 182
<211> LENGTH: 741
<212> TYPE: DNA
<213> ORGANISM: Artificial Sequence
<220> FEATURE:
<223> OTHER INFORMATION: Synthetic polynucleotide encoding an anti-VEGF scFv (SEQ ID NO: 174)

<400> SEQUENCE: 182

```
gaggtgcagc tgttggagtc tgggggaggc ttggtacagc ctgggggtc cctgagactc     60 tcctgtgcag cctctggatt cacctttagc ggttatgcta tgagctgggt ccgccaggct    120
ccagggaagg ggctggagtg ggtctcaggg atctctcatg atggtggtaa tacatattac    180
gctgattctg taaaaggtcg gttcaccatc tccagagaca attccaagaa cacgctgtat    240
ctgcaaatga acagcctgag agccgaggac acggccgtgt attactgtgc gagagatcgt    300
aggaagggtc cttcgactga gttcgactac tggggccagg gtacactggt caccgtgagc    360
tcaggtggag gcggttcagg cggaggtgga tccggcggtg gcggatcgca gtctgtgctg    420
actcagccac cctcagcgtc tggaccccc gggcagaggg tcaccatctc ttgtactggc    480
tcttcatcta atattggcag taattctgtc tcctggtacc agcagctccc aggaacggcc    540
cccaaactcc tcatctatga tgataataat cggccaagcg gggtccctga ccgattctct    600
ggctccaagt ctggcacctc agcctccctg gccatcagtg gctccggtc gaggatgag     660 gctgattatt actgtggtgc ttgggattat agcctgagtg cttatgtctt cggcggaggc    720
accaagctga cggtcctagg c                                              741
```

<210> SEQ ID NO 183
<211> LENGTH: 759
<212> TYPE: DNA
<213> ORGANISM: Artificial Sequence
<220> FEATURE:
<223> OTHER INFORMATION: Synthetic polynucleotide encoding an anti-VEGF scFv (SEQ ID NO: 175)

<400> SEQUENCE: 183

```
gaggtgcagc tgttggagtc tgggggaggc ttggtacaga ctgggggtc cctgagactc     60 tcctgtgcag cctctggatt cacctttagc gattatgcta tgagctgggt ccgccaggct    120
ccagggaaag ggctggagtg ggtctcatgg atctatcctg gtgatagtag tatatattac    180
```

-continued

```
gctgattctg taaaaggtcg gttcaccatc tccagagaca attccaagaa cacgctgtat    240
ctgcaaatga acagcctgag agccgaggac acggccgtgt attactgtgc gagacttctt    300
agtattgatc aggctcagtt gcattattat tatgatgcta tggacgtctg gggccagggt    360
acactggtca ccgtgagctc aggtggaggc ggttcaggcg aggtggatc cggcggtggc     420 ggatcgcagt ctgtgctgac tcagccaccc tcagcgtctg gaccccgg gcagagggtc      480 accatctctt gtactggctc ttcatctaat attggcaatt attatgtcta ctggtaccag    540
cagctcccag gaacggcccc caaactcctc atctatgcta atagtcatcg gccaagcggg    600
gtccctgacc gattctctgg ctccaagtct ggcacctcag cctccctggc catcagtggg    660
ctccggtccg aggatgaggc tgattattac tgtggttctt gggatgatag cctgagtgct    720
tatgtcttcg gcggaggcac caagctgacg gtcctaggc                          759
```

<210> SEQ ID NO 184
<211> LENGTH: 1338
<212> TYPE: PRT
<213> ORGANISM: Artificial Sequence
<220> FEATURE:
<223> OTHER INFORMATION: Synthetic human VEGFR-1

<400> SEQUENCE: 184

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Lys Leu Lys Asp Pro
                 20                  25                  30

Glu Leu Ser Leu Lys Gly Thr Gln His Ile Met Gln Ala Gly Gln Thr
             35                  40                  45

Leu His Leu Gln Cys Arg Gly Glu Ala Ala His Lys Trp Ser Leu Pro
         50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
                100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
        130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
```

-continued

Asn Lys Arg Ala Ser Val Arg Arg Ile Asp Gln Ser Asn Ser His
260                 265                 270
Ala Asn Ile Phe Tyr Ser Val Leu Thr Ile Asp Lys Met Gln Asn Lys
    275                 280                 285
Asp Lys Gly Leu Tyr Thr Cys Arg Val Arg Ser Gly Pro Ser Phe Lys
290                 295                 300
Ser Val Asn Thr Ser Val His Ile Tyr Asp Lys Ala Phe Ile Thr Val
305                 310                 315                 320
Lys His Arg Lys Gln Gln Val Leu Glu Thr Val Ala Gly Lys Arg Ser
            325                 330                 335
Tyr Arg Leu Ser Met Lys Val Lys Ala Phe Pro Ser Pro Glu Val Val
340                 345                 350
Trp Leu Lys Asp Gly Leu Pro Ala Thr Glu Lys Ser Ala Arg Tyr Leu
    355                 360                 365
Thr Arg Gly Tyr Ser Leu Ile Ile Lys Asp Val Thr Glu Glu Asp Ala
370                 375                 380
Gly Asn Tyr Thr Ile Leu Leu Ser Ile Lys Gln Ser Asn Val Phe Lys
385                 390                 395                 400
Asn Leu Thr Ala Thr Leu Ile Val Asn Val Lys Pro Gln Ile Tyr Glu
            405                 410                 415
Lys Ala Val Ser Ser Phe Pro Asp Pro Ala Leu Tyr Pro Leu Gly Ser
420                 425                 430
Arg Gln Ile Leu Thr Cys Thr Ala Tyr Gly Ile Pro Gln Pro Thr Ile
    435                 440                 445
Lys Trp Phe Trp His Pro Cys Asn His Asn His Ser Glu Ala Arg Cys
450                 455                 460
Asp Phe Cys Ser Asn Asn Glu Glu Ser Phe Ile Leu Asp Ala Asp Ser
465                 470                 475                 480
Asn Met Gly Asn Arg Ile Glu Ser Ile Thr Gln Arg Met Ala Ile Ile
            485                 490                 495
Glu Gly Lys Asn Lys Met Ala Ser Thr Leu Val Val Ala Asp Ser Arg
500                 505                 510
Ile Ser Gly Ile Tyr Ile Cys Ile Ala Ser Asn Lys Val Gly Thr Val
    515                 520                 525
Gly Arg Asn Ile Ser Phe Tyr Ile Thr Asp Val Pro Asn Gly Phe His
530                 535                 540
Val Asn Leu Glu Lys Met Pro Thr Glu Gly Glu Asp Leu Lys Leu Ser
545                 550                 555                 560
Cys Thr Val Asn Lys Phe Leu Tyr Arg Asp Val Thr Trp Ile Leu Leu
            565                 570                 575
Arg Thr Val Asn Asn Arg Thr Met His Tyr Ser Ile Ser Lys Gln Lys
580                 585                 590
Met Ala Ile Thr Lys Glu His Ser Ile Thr Leu Asn Leu Thr Ile Met
    595                 600                 605
Asn Val Ser Leu Gln Asp Ser Gly Thr Tyr Ala Cys Arg Ala Arg Asn
610                 615                 620
Val Tyr Thr Gly Glu Glu Ile Leu Gln Lys Lys Glu Ile Thr Ile Arg
625                 630                 635                 640
Asp Gln Glu Ala Pro Tyr Leu Leu Arg Asn Leu Ser Asp His Thr Val
            645                 650                 655
Ala Ile Ser Ser Ser Thr Thr Leu Asp Cys His Ala Asn Gly Val Pro
660                 665                 670

```
Glu Pro Gln Ile Thr Trp Phe Lys Asn Asn His Lys Ile Gln Gln Glu
        690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
        770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
        835                 840                 845

Ile Lys Lys Ser Pro Thr Cys Arg Thr Val Ala Val Lys Met Leu Lys
850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
        995                 1000                1005

Gly Met Glu Phe Leu Ser Ser Arg Lys Cys Ile His Arg Asp Leu Ala
    1010                1015                1020

Ala Arg Asn Ile Leu Leu Ser Glu Asn Val Val Lys Ile Cys Asp
1025                1030                1035                1040

Phe Gly Leu Ala Arg Asp Ile Tyr Lys Asn Pro Asp Tyr Val Arg Lys
                1045                1050                1055

Gly Asp Thr Arg Leu Pro Leu Lys Trp Met Ala Pro Glu Ser Ile Phe
            1060                1065                1070

Asp Lys Ile Tyr Ser Thr Lys Ser Asp Val Trp Ser Tyr Gly Val Leu
        1075                1080                1085

Leu Trp Glu Ile Phe Ser Leu Gly Gly Ser Pro Tyr Pro Gly Val Gln
    1090                1095                1100
```

```
Met Asp Glu Asp Phe Cys Ser Arg Leu Arg Glu Gly Met Arg Met Arg
1105                1110                1115                1120

Ala Pro Glu Tyr Ser Thr Pro Glu Ile Tyr Gln Ile Met Leu Asp Cys
            1125                1130                1135

Trp His Arg Asp Pro Lys Glu Arg Pro Arg Phe Ala Glu Leu Val Glu
        1140                1145                1150

Lys Leu Gly Asp Leu Leu Gln Ala Asn Val Gln Gln Asp Gly Lys Asp
        1155                1160                1165

Tyr Ile Pro Ile Asn Ala Ile Leu Thr Gly Asn Ser Gly Phe Thr Tyr
    1170                1175                1180

Ser Thr Pro Ala Phe Ser Glu Asp Phe Phe Lys Glu Ser Ile Ser Ala
1185                1190                1195                1200

Pro Lys Phe Asn Ser Gly Ser Ser Asp Asp Val Arg Tyr Val Asn Ala
            1205                1210                1215

Phe Lys Phe Met Ser Leu Glu Arg Ile Lys Thr Phe Glu Glu Leu Leu
        1220                1225                1230

Pro Asn Ala Thr Ser Met Phe Asp Asp Tyr Gln Gly Asp Ser Ser Thr
        1235                1240                1245

Leu Leu Ala Ser Pro Met Leu Lys Arg Phe Thr Trp Thr Asp Ser Lys
    1250                1255                1260

Pro Lys Ala Ser Leu Lys Ile Asp Leu Arg Val Thr Ser Lys Ser Lys
1265                1270                1275                1280

Glu Ser Gly Leu Ser Asp Val Ser Arg Pro Ser Phe Cys His Ser Ser
            1285                1290                1295

Cys Gly His Val Ser Glu Gly Lys Arg Arg Phe Thr Tyr Asp His Ala
        1300                1305                1310

Glu Leu Glu Arg Lys Ile Ala Cys Cys Ser Pro Pro Pro Asp Tyr Asn
        1315                1320                1325

Ser Val Val Leu Tyr Ser Thr Pro Pro Ile
    1330                1335

<210> SEQ ID NO 185
<211> LENGTH: 101
<212> TYPE: PRT
<213> ORGANISM: Artificial Sequence
<220> FEATURE:
<223> OTHER INFORMATION: Synthetic Ig2 domain of VEGFR-1 (VIG2)

<400> SEQUENCE: 185

Ser Asp Thr Gly Arg Pro Phe Val Glu Met Tyr Ser Glu Ile Pro Glu
 1               5                  10                  15

Ile Ile His Met Thr Glu Gly Arg Glu Leu Val Ile Pro Cys Arg Val
                20                  25                  30

Thr Ser Pro Asn Ile Thr Val Thr Leu Lys Lys Phe Pro Leu Asp Thr
            35                  40                  45

Leu Ile Pro Asp Gly Lys Arg Ile Ile Trp Asp Ser Arg Lys Gly Phe
        50                  55                  60

Ile Ile Ser Asn Ala Thr Tyr Lys Glu Ile Gly Leu Leu Thr Cys Glu
 65                 70                  75                  80

Ala Thr Val Asn Gly His Leu Tyr Lys Thr Asn Tyr Leu Thr His Arg
                85                  90                  95

Gln Thr Asn Thr Ile
            100

<210> SEQ ID NO 186
<211> LENGTH: 303
```

```
<212> TYPE: DNA
<213> ORGANISM: Artificial Sequence
<220> FEATURE:
<223> OTHER INFORMATION: Synthetic polynucleotide encoding VIG2

<400> SEQUENCE: 186
agtgatacag gtagacctttt cgtagagatg tacagtgaaa tccccgaaat tatacacatg      60
actgaaggaa gggagctcgt cattccctgc cgggttacgt cacctaacat cactgttact     120
ttaaaaaagt ttccacttga cactttgatc cctgatggaa aacgcataat ctgggacagt     180
agaaagggct tcatcatatc aaatgcaacg tacaaagaaa tagggcttct gacctgtgaa     240
gcaacagtca atgggcattt gtataagaca aactatctca cacatcgaca aaccaataca     300
atc                                                                   303

<210> SEQ ID NO 187
<211> LENGTH: 5
<212> TYPE: PRT
<213> ORGANISM: Artificial Sequence
<220> FEATURE:
<223> OTHER INFORMATION: Synthetic linker

<400> SEQUENCE: 187

Gly Gly Gly Gly Ser
 1               5

<210> SEQ ID NO 188
<211> LENGTH: 10
<212> TYPE: PRT
<213> ORGANISM: Artificial Sequence
<220> FEATURE:
<223> OTHER INFORMATION: Synthetic linker

<400> SEQUENCE: 188

Gly Gly Gly Gly Ser Gly Gly Gly Gly Ser
 1               5                  10

<210> SEQ ID NO 189
<211> LENGTH: 20
<212> TYPE: PRT
<213> ORGANISM: Artificial Sequence
<220> FEATURE:
<223> OTHER INFORMATION: Synthetic linker

<400> SEQUENCE: 189

Gly Gly Gly Gly Ser Gly Gly Gly Ser Gly Gly Gly Gly Ser Gly
 1               5                  10                  15

Gly Gly Gly Ser
            20

<210> SEQ ID NO 190
<211> LENGTH: 114
<212> TYPE: PRT
<213> ORGANISM: Artificial Sequence
<220> FEATURE:
<223> OTHER INFORMATION: Synthetic light chain variable region of anti
      c-Met antibody

<400> SEQUENCE: 190

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp Tyr Gln Gln Lys Pro Gly Lys
```

-continued

```
            35                  40                  45
Ala Pro Lys Met Leu Ile Ile Trp Ala Ser Thr Arg Val Ser Gly Val
        50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Ser Tyr Ser Arg Pro Tyr Thr Phe Gly Gln Gly Thr Lys Val Glu Ile
            100                 105                 110

Lys Arg
```